United States Patent [19]

Inouye et al.

[11] Patent Number: 4,666,836

[45] Date of Patent: May 19, 1987

[54] NOVEL CLONING VEHICLES FOR POLYPEPTIDE EXPRESSION IN MICROBIAL HOSTS

[75] Inventors: Masayori Inouye, Setauket, N.Y.; Kenzo Nakamura, Tokyo, Japan

[73] Assignee: The Research Foundation of State University of New York, Albany, N.Y.

[21] Appl. No.: 354,299

[22] Filed: Mar. 3, 1982

Related U.S. Application Data

[63] Continuation-in-part of Ser. No. 286,166, Jul. 23, 1981, abandoned, which is a continuation-in-part of Ser. No. 222,010, Jan. 2, 1981, abandoned.

[51] Int. Cl.$^4$ .................. C12P 21/00; C12N 15/00; C12N 1/20; C12N 1/00
[52] U.S. Cl. .................. 435/68; 435/172.3; 435/253; 435/317; 935/29; 935/41; 935/43
[58] Field of Search .................. 435/68, 70, 71, 172, 435/317, 253, 172.3; 935/41, 43, 29

[56] References Cited

U.S. PATENT DOCUMENTS 4,237,224 12/1980 Cohen et al. .
4,336,336 6/1982 Silhavy et al. .................. 435/172

FOREIGN PATENT DOCUMENTS 1929 5/1979 European Pat. Off. .

OTHER PUBLICATIONS

Hamming et al, Nucleic Acids Research, vol. 7, No. 4, pp. 1019-1033, (1979).
Nakamura et al, J. Bact., vol. 137, No. 1, pp. 595-604.
Goeddel et al., Nature, vol. 281, pp. 544-548, Oct. 1979.
Seeburg et al., Nature, vol. 276, pp. 795-798, Dec. 1978.
Villa-Komaroff et al., Proc. Nat. Acad. Sci. USA, vol. 75, pp. 3727-3731, Aug. 1978.
Tacon et al., Molec. Gen. Genet., vol. 177, pp. 427-438, 1980.
Charney et al., Nucleic Acids Research, vol. 5, pp. 4479-4494, Nov. 1978.
Hallewell et al., Gene, vol. 9, pp. 27-47, 1980.
Henning et al., Proc. Nat. Acad. Sci. USA, vol. 76, No. 9, pp. 4360-4364, Sep. 1979.
Sato et al., J. Bacteriol., vol. 139, No. 2, pp. 468-477, Aug. 1979.
Movva et al., Proc. Nat. Acad. Sci. USA, vol. 77, No. 7, pp. 3845-3849, Jul. 1980.
Talmadge et al., Gene, vol. 12, pp. 235-241, 1980.
Shimatake et al., Nature, vol. 292, pp. 128-132, Jul. 1981.

Primary Examiner—Alvin E. Tanenholtz
Attorney, Agent, or Firm—Gottlieb, Rackman & Reisman

[57] ABSTRACT

Methods and compositions are provided for expression of polypeptides in transformed bacterial hosts. A novel class of plasmid cloning vehicles includes a DNA sequence coding for the desired polypeptide linked in reading phase with one or more functional fragments derived from an outer membrane protein gene of a gram-negative bacterium, and also linked with an additional promoter sequence in certain cases. The methods utilize such plasmids to introduce genetic capability into microorganisms for the production of proteins, such as medically or commercially useful hormones, enzymes, immunogenic proteins, or intermediates therefor.

46 Claims, 27 Drawing Figures

FIG. 1

```
                                                                        TGGCTCTGCAGAGCA
                                                                        ACCGAGACGTCTCGT

-350                                   -300
ATCTGGCACACAAAGGTGACGTTGTAGTTATGGTTTCTGGTGCACTGGTACCGAGCGGCACTACTAACACCGCATCTGTTCACGTCCTGTAATATTGCTT
TAGACCGTGTGTTTCCACTGCAACATCAATACCAAAGACCACGTGACCATGGCTCGCCGTGATGATTGTGGCGTAGACAAGTGCAGGACATTATAACGAA

-250                                   -200
TTGTGAATTAATTTGTATATCGGCGCTTTTTTTATTTAATCGATAACCAGAAGCAATAAAAAATCAAATCGGATTTCACTATATAATCTCACTTTATCTA
AACACTTAATTAAACATATAGCCGCGAAAAAAATAAATTAGCTATTGGTCTTCGTTATTTTTTAGTTTAGCCTAAAGTGATATATTAGAGTGAAATAGAT

-150                                   -100
AGATGAATCCGATGGAAGCATCCTGTTTTCTCTCAATTTTTTTATCTAAAACCCAGCGTTCGATGCTTCTTTGAGCGAACGATCAAAAATAAGTGCCTTC
TCTACTTAGGCTACCTTCGTAGGACAAAAGAGAGTTAAAAAAATAGATTTTGGGTCGCAAGCTACGAAGAAACTCGCTTGCTAGTTTTTATTCACGGAAG

-1 +1                                      +50
        -50
CCATCAAAAAAATATTCTCAACATAAAAAACTTTGTGTAATACTTGTAAGGCTACATGGAGATTAACTCAATCTAGAGGGTATTAATAATGAAAGCTACT
GGTAGTTTTTTTATAAGAGTTGTATTTTTTGAAACACATTATGAACATTGCGATGTACCTCTAATTGAGTTAGATCTCCCATAATTATTACTTTCGATGA
                                                  mRNA Start                            MetLysAlaThr
                                                                                         1

+100                                       +150
AAACTGGTACTGGGCGCGGTAATCCTGGGTTGTACTCTGCTGGCAGGTTGCTCCAGCAACGCTAAAATCGATCAGCTGTCTTCTGACGTTCAGACTCTGA
TTTGACCATGACCCGCGCCATTAGGACCCAAGATGAGACGACCGTCCAACGAGGTCGTTGCGATTTTAGCTAGTCGACAGAAGACTGCAAGTCTGAGACT

LysLeuValLeuGlyAlaValIleLeuGlySerThrLeuLeuAlaGlyCysSerSerAsnAlaLysIleAspGlnLeuSerSerAspValGlnThrLeuA
              10                        20                        30

+200                                       +250
ACGCTAAAGTTGACCAGCTGAGCAACGACGTGAACGCAATGCGTTCCGACGTTCAGGCTGCTAAAGATGACGCAGCTCGTGCTAACCAGCGTCTGGACAA
TGCGATTTCAACTGGTCGACTCTGTGCTGCACTTGCGTTACGCAAGGCTGCAAGTCCGACGATTTCTACTGCGTCGAGCACGATTGGTCGCAGACCTGTT snAlaLysValAspGlnLeuSerAsnAspValAsnAlaMetArgSerAspValGlnAlaAlaLysAspAspAlaAlaArgAlaAsnGlnArgLeuAspAs
     40                        50                        60                        70

+300                                       +350
CATGGCTACTAAATACCGCAAGTAATAGTACCTGTGAAGTGAAAAATGGCGCACATTGTGCGACATTTTTTTGTCTGCCGTTTACCGCTACTGCGTCAC
GTACCGATGATTTATGGCGTTCATTATCATGGACACTTCACTTTTTACCGCGTGTAACACGCTGTAAAAAAAACAGACGGCAAATGGCGATGACGCAGTG nMetAlaThrLysTyrArgLys                                                     Stop
               78

+400
GCGTAACATATTCCCTTGCTCTGGTTCACCATTCTGCGCTGACTCTACTGAAGGCGCATTGCTGGCTGCGGGAGTTGCTCCACTGCTCACCGAAACCGG
CGCATTGTATAAGGGAACGAGACCAAGTGGTAAGACGCGACTGAGATGACTTCCGCGTAACGACCGACGCCCTCAACGAGGTGACGAGTGGCTTTGGCC
```

FIG. 2

5'-end:
```
       1                                        10                            20                               30                              40
      G-C-U-A-C-A-U-G-G-A-G-A-U-U-A-A-C-U-C-A-A-U-C-U-A-G-A-G-G-U-A-U-U-A-A-U-A-A-G-C-U
                                                                                  MET - LYS - ALA
                                                                                   1
       50                              60                             70                              80                             90
      A-C-U-A-A-A-C-U-G-G-U-A-C-U-G-G-C-C-G-G-G-U-A-A-U-C-C-U-G-G-G-U-A-C-U-G-G-C-A-G-G-U
      THR - LYS - LEU - VAL - LEU - GLY - ALA - VAL - ILE - LEU - GLY - SER - THR - LEU - LEU - ALA - GLY
            5                                      10                                     15                           20

100                             110                             120                            130                           140
      U-G-C-U-C-C-A-G-C-A-A-C-G-C-A-A-A-A-A-U-C-G-A-U-C-A-G-C-U-U-C-U-G-G-A-C-G-C-U-G
      CYS - SER - SER - ASN - ALA - LYS - ILE - ASP - GLN - LEU - SER - SER - ASP - VAL - GLN - THR - LEU
            25                                   30                                    35

150                             160                             170                            180                           190                       200
      A-A-C-G-C-U-A-A-A-A-G-U-U-G-A-C-C-A-A-C-C-A-G-A-C-G-A-A-C-G-A-A-C-G-C-G-U-U-C-C-G-A-C-
      ASN - ALA - LYS - VAL - ASP - GLN - LEU - SER - ASN - ASP - VAL - ASN - ALA - MET - ARG - SER - ASP
            40                                   45                                   50

210                             220                             230                            240                           250
      G-U-U-C-A-G-G-C-U-G-C-U-A-A-A-A-G-A-U-G-A-C-A-G-C-U-A-A-A-U-C-G-U-U-G-G-A-C-A-A-C-
      VAL - GLN - ALA - ALA - LYS - ASP - ASP - ALA - ALA - ARG - ALA - ASN - GLN - ARG - LEU - ASP - ASN
            55                                   60                                   65                                   70

260                             270                             280                            290                           300
      A-U-G-G-C-U-A-C-A-A-A-A-A-U-A-C-C-G-G-A-A-A-G-U-A-A-A-A-A-U-G-G-A-A-A-A-A-U-G-G-C-C-
      MET - ALA - THR - LYS - TYR - ARG - LYS
            75                       78

310                             320
      A-C-A-U-U-G-U-G-G-C-C-C-A-U-U-U-U-U-U-U-U-OH    :3'-end
```

NOVEL CLONING VEHICLES FOR POLYPEPTIDE EXPRESSION IN MICROBIAL HOSTS

This invention was made with Government support under Contract No. 5-R01-gm1904308 awarded by the National Institutes of Health. The Government has certain rights in this invention.

This is a continuation-in-part of our prior copending application, Ser. No. 286,166, filed July 23, 1981, which is a continuation-in-part of our prior copending application Ser. No. 222,010, filed Jan. 2, 1981 both abandoned.

TECHNICAL FIELD

This invention relates generally to the field of recombinant genetics, and specifically to a novel class of plasmid cloning vehicles with which exogenous genes may be expressed in transformed bacterial hosts.

As is well-known in the art, genetic information is encoded on double-stranded deoxyribonucleic acid ("DNA") molecules ("genes") according to the sequence in which the DNA coding strand presents the characteristic bases of its repeating nucleotide components. The four nitrogenous bases that characterize the two strands of DNA nucleotides are linked in complementary pairs by hydrogen bonds to form the double helix of DNA: adenine (A) is linked to thymine (T) and guanine (G) to cytosine (C). "Expression" of the encoded information involves a two-part process. According to the dictates of certain control regions in the gene, an enzyme ("RNA polymerase") may be caused to move along the DNA coding strand, synthesizing messenger ribonucleic acid ("mRNA") in a process called "transcription." The DNA coding strand typically includes signals, which can be recognized by RNA polymerase, for both initiation and termination of transcription. In a subsequent "translation" step, the cell's ribosomes, in conjunction with transfer-RNA, convert the RNA "message" into proteins or "polypeptides," which determine cell form and function. Included in the information transcribed by mRNA from DNA are signals for the initiation and termination of ribosomal translation, as well as signals specifying the identity and sequence of the amino acids which make up the polypeptide.

The DNA coding strand comprises long sequences of nucleotide triplets called "codons" in which the characteristic bases of the nucleotides in each triplet or codon encode specific bits of information. For example, three nucleotides read as ATG (adenine-thymine-guanine) result in an mRNA signal which is interpreted as "start translation," while termination codons TAG, TAA and TGA are interpreted as "stop translation." Between the initiation codon and the termination codon lies the so-called "structural gene," the codons of which define the amino acid sequence ultimately translated. That definition proceeds according to the well-established "genetic code" (e.g., Watson, J. D., *Molecular Biology Of The Gene*, 3rd ed. [New York: W. A. Benjamin, Inc., 1976]), which specifies the codons for the various amino acids. Since there are 64 possible codon sequences but only twenty known amino acids, the genetic code is degenerate in the sense that different codons may yield the same amino acid. However, the code is precise in that for each amino acid there is at least one codon, and in that each codon yields a single amino acid and no other. Thus, for example, all of the codons, TTT, TTC, TTA and TTG, when read as such, encode for serine and no other amino acid. It will be apparent that during translation the proper reading phase or reading frame must be maintained in order to obtain the proper amino acid sequence in the polypeptide ultimately produced.

The DNA sequence within the control region of a gene which mediates the initiation of transcription is termed the "promoter" of the gene, while the specific signal encoded in the DNA following the structural gene at which transcription ends is defined as the "transcription termination site." Although the mechanisms which underlie the initiation and termination of transcription are not completely understood, it is believed that the promoter provides the site at which RNA polymerase must bind in order to initiate transcription, and that the effectiveness or "strength" of a particular promoter or terminator signal is determined by the efficiency with which RNA polymerase can recognize and interact with these signals. This in turn depends in large part upon the particular base sequence of the DNA at or near these sites (see, e.g., Rosenberg, M., et al., *Ann. Rev. Genet.*, 1979 13, 319-353).

The control regions of some genes may also include DNA sequences which can be recognized by certain effector molecules, the action of which can positively or negatively influence the interaction between RNA polymerase and DNA and thereby further regulate gene expression at the level of transcription. The expression of genetic information by such genes may, for example, be inhibited in the absence of a given substance, and is therefore termed "inducible." On the other hand, there also exist many genes (such as the lipoprotein gene of the gram-negative bacterium *Escherichia coli* ["*E. coli*"]) whose control regions are not affected by effector molecules. The expression of genetic information by such genes is continuous during the lifetime of the cell, and is termed "constitutive." The control regions of such genes are generally comprised solely of a promoter signal and a terminator signal which immediately precede and follow, respectively, the DNA sequence to be transcribed.

The control regions cause mRNA synthesis to begin at a "transcription initiation site" located at or near the promoter, and to proceed until the transcription termination site is reached, producing an mRNA molecule of predetermined length with a base sequence complementary to the base sequence of the transcribed DNA. The DNA sequence between these two points defines not only the structural gene, the codons of which are ultimately translated for polypeptide expression, but also an "untranslated" region on either side of the structural gene.

Transcription therefore typically results in an mRNA molecule which carries a translatable RNA sequence, located between two untranslated regions. The untranslated region which precedes the structural sequence is known as the "5'-untranslated region," while the region which follows the structural signals is known as the "3'-untranslated region." As disclosed in detail hereinbelow, the DNA coding sequences for both of these untranslated regions, as well as the DNA coding sequences embodying the promoter signal and the terminator signal of certain genes, all of which may be referred to individually or collectively herein as "functional fragments" of those genes, may be effectively used in the creation of the novel cloning vehicles of the present invention.

As used herein, the term "cloning vehicle" defines a non-chromosomal double-stranded DNA molecule in "plasmid" form which can be replicated after being placed within a unicellular organism by a process called "transformation." An organism so transformed is called a "transformant." For present purposes, a "plasmid" is a circular non-chromosomal double-stranded DNA molecule derived from viruses or bacteria, the latter being termed "bacterial plasmids."

Advances in biochemistry in recent years have led to the construction of "recombinant" cloning vehicles in which, for example, plasmids are made to contain exogenous DNA. In particular instances a recombinant plasmid may include DNA that codes for polypeptides not ordinarily produced by the organism susceptible to transformation by the recombinant plasmid, and the exogenous DNA may in some cases comprise human genetic material. Typically, plasmids are cleaved to provide linear DNA having ligatable termini. These are bound to an exogenous gene having ligatable termini to provide a biologically functional moiety with a desired phenotypical property. The recombinant moiety is inserted into a micro-organism by transformation and transformants are isolated and cloned, with the object of obtaining large populations capable of expressing the new genetic information. Methods and means of forming recombinant cloning vehicles and transforming organisms with them have been widely reported in the literature, and generalized discussions of the subject appear in Cohen, S., *Scientific American* 233, 24–33 (July 1975), and in Gilbert, W., et al., *Scientific American* 242, 74–94 (April, 1980). These and other publications allude herein are incorporated by reference.

A variety of techniques are available for DNA recombination, according to which adjoining ends of separate DNA fragments are tailored in one way or another to facilitate ligation. The latter term refers to the formation of phosphodiester bonds between adjoining nucleotides, through the agency of a catalytic enzyme such as T4 DNA ligase. Thus, DNA fragments with "blunt" ends may be directly ligated. Alternatively, fragments containing complementary single strands at their adjoining ends are advantaged by hydrogen bonding which positions the respective ends for subsequent ligation. Such single strands, referred to as "cohesive termini," may be formed by the addition of nucleotides to blunt ends using terminal transferase, or sometimes simply by "chewing back" one strand of a blunt end with an enzyme such as λ-exonuclease. Most commonly, however, such single strands may be formed by restriction endonucleases (also called restriction enzymes), which cleave the phosphodiester bonds in and around unique sequences of nucleotides of about 4–6 base pairs in length. Many restriction endonucleases and their recognition sequences are known, the so-called Eco RI endonuclease being one of the most widely employed.

Restriction endonucleases which cleave double-stranded DNA at unique sequences (e.g., at rotationally symmetric "palindromes") may leave cohesive termini. Thus, a plasmid or other cloning vehicle may be cleaved, leaving termini each comprising half of the restriction endonuclease recognition site. A cleavage product of exogenous DNA obtained with the same restriction endonuclease will have ends complementary to those of the plasmid termini. Alternatively, synthetic DNA comprising cohesive termini may be provided for insertion into the cleaved vehicle. To discourage rejoinder of the vehicle's cohesive termini pending insertion of exogenous DNA, the termini can be digested with alkaline phosphatase, providing molecular selection for closure incorporating the exogenous fragment. Incorporation of a fragment in the proper orientation relative to other aspects of the vehicle may be enhanced when the fragment supplants vehicle DNA excised by two different restriction endonucleases, and when the fragment itself comprises termini respectively constituting half the recognition sequence of the same two different endonucleases.

As a result of wide-ranging work in recent years in recombinant DNA research, the prior art includes a number of successful and commercially viable schemes to express functional polypeptide products such as insulin, somatostatin and human and animal growth hormone, but these schemes generally utilize only one or two functional fragments of certain genes to control polypeptide expression.

BACKGROUND ART

The efforts of the prior art to express structural information for the production of eukaryotic cell proteins in transformed bacteria vary widely in their approach. One class of prior art cloning vehicles, which is represented by those described in European Patent Publication No. 1929 (published on May 16, 1979) and in Goeddel, D. V., et al., *Nature* 281, 544–548 (1979), is preferably constructed in accordance with a scheme in which the structural gene for the desired polypeptide (e.g., somatostatin) is inserted (together with a translation termination codon) at a restriction endonuclease recognition site located within the *E. coli* β-galactosidase structural gene, bringing the expression of the desired polypeptide under the control of the β-galactosidase or "lac" promoter. Since some of the codons for the β-galactosidase enzyme are thereby positioned to be translated in advance of the structural gene of the desired product, expression of this fused DNA sequence in an *E. coli* transformant is said to result in a precursor protein comprising a somatostatin (or other) polypeptide preceded by a superfluous protein fragment consisting of either a sequence of several amino acid residues derived from the β-galactosidase structural gene or virtually the entire β-galactosidase amino acid sequence, depending upon which insertion site is chosen.

Another effort involves use of the lac UV5 promoter in a bacteriophage vehicle, λ, or in a plasmid vehicle pBR322 (Charnay, P., et al., *Nucleic Acids Res.* 5, 4479–4494 [1978]). In both cases, each vector allows the fusion of a cloned gene to the lacZ gene in a different phase relative to the translation initiation codon of the lacZ gene. Used in combination, these vectors are said to allow translation of a cloned gene in any one of the three coding phases.

The fact that this prior art scheme contemplates expression of the conjugate precursor protein under the control of the lac promoter gives rise to certain disadvantages. The machinery for gene expresion associated with the control region of the β-galactosidase gene is not as efficient as the machinery for gene expression associated with certain other bacterial genes. Accordingly, the yield of the expression product is expected to range from approximately 100,000 molecules per host cell up to a maximum of about 200,000 molecules per host cell. Furthermore, the efficiency of this system may be further reduced because the mRNA molecule transcribed from the DNA of these prior art cloning vehicles is unnecessarily long (extending in some cases far "upstream" and in other cases far "downstream" of the desired polypeptide through the remainder of the β-galactosidase structural gene), and may lack certain features, called "secondary structures" or "stem-and-loop structures," which are believed to confer greater stability upon the mRNA molecule, thereby increasing its availability for ribosomal translation. Finally, the fused precursor-protein expression product accumulates inside the transformant cell, perhaps interfering with normal cellular activities and certainly requiring cell disruption in the harvesting process.

A second class of prior art cloning vehicles, represented by those described in Seeburg, P. H., et al., *Nature* 276, 795-798 (1978), involves the expression of similar "hybrid" proteins. In this scheme, the structural gene for the desired polypeptide is inserted within the structural gene for the β-lactamase (or penicillinase) enzyme of *E. coli*. Although this protein is normally synthesized with a short leader sequence (also called a "signal peptide"), which is located at the amino terminus of the protein and is thought to direct secretion of the protein across the cytoplasmic membrane, the expected fused precursor-protein expression product of such a recombinant vehicle (containing the DNA sequence for rat growth hormone) in an *E. coli* transformant was not actually detected outside the cell, despite a reasonable expectation that a β-lactamase-rat growth hormone conjugate would be secreted into the periplasmic space.

In any event, harvest of this product is expected to yield only approximately 24,000 molecules per host cell, and other workers using this scheme for expression of rat insulin have estimated an even smaller yield, on the order of 100 molecules per host cell (see VillaKomaroff, L., et al., *Proc. Natl. Acad. Sci. U.S.A.* 75, 3727-3731 [1978]). It is believed that the relatively modest recovery of the desired product which might be obtained with such cloning vehicles is due to the relative weakness of the *E. coli* β-lactamase promoter, under the control of which the fussion product is expressed, as compared with the promoters of certain other components of the *E. coli* genome.

A third class of prior art cloning vehicles is represented by those described in Tacon, W., et al., *Molec. gen. Genet.* 177, 427-428 (1980) and in Hallewell, R. A. and Emtage, S., *Gene* 9, 27-47 (1980), wherein the use of the *E. coli* tryptophan gene is described. In the former case, three plasmids are constructed from pBR322 which contain the *E. coli* tryptophan promoter-operator, as well as nucleotides specifying the leader sequence and first seven amino acids of the trpE gene. These plasmids have a Hind III cloning site situated downstream from the translation initiation codon (ATG) of the trpE gene, with the cloning site in each plasmid differing in its translation phase relative to the initiation codon. In the latter case, the tryptophan promoter-operator, the trpE gene and 15% of the trpD gene are used for the expression of foreign genes.

In summary, the prior art has failed to develop cloning vehicles which are suited for the efficient expression of prokaryotic and eukaryotic gene products in bacterial transformants, and which at the same time utilize functional fragments such as the 3'-untranslated region or the transcription termination site of any gene for expression of an exogenous DNA insert fragment. Furthermore, the prior art has failed to utilize more than one promoter in a single expression plasmid to control the production of the desired protein. It is therefore the principal object of the present invention to provide a new class of plasmid cloning vehicles incorporating not only the promoter and 5'-untranslated region, but also the 3'-untranslated region and the transcription termination site, derived from a particular class of bacterial genes, and incorporating a second promoter fragment as well.

DISCLOSURE OF INVENTION

Briefly, in accordance with the primary objective of this invention, a class of recombinant bacterial plasmid cloning vehicles for expression of exogenous genes in transformed bacterial hosts is provided, comprising a DNA insert fragment coding for the desired polypeptide, linked with one or more functional fragments derived from an outer membrane protein gene of any gram-negative bacterium. In a preferred embodiment, the exogenous DNA codes for mammalian hormones, enzymes or immunogenic proteins (or intermediates therefor), the functional fragments are derived from the lipoprotein gene of *E. coli*, and the desired polypeptide is expressed in *E. coli* transformants. In a more preferred embodiment of the present invention, the DNA sequence coding for the desired protein is linked with and is expressed in conjunction with four specific functional fragments associated with the *E. coli* lipoprotein gene, namely, the promoter, the 5'-untranslated region, the 3'-untranslated region and the transcription termination site of that gene.

Three alternative insertion sites for the exogenous DNA are provided, the selection of which can influence the ultimate location at which the expression product can be found and collected. Using one of these insertion sites, the desired polypeptide can thus be expressed with a leader sequence located at the amino terminal which comprises the signal peptide of the *E. coli* lipoprotein, such that the desired product may be secreted through the cytoplasmic membrane and the signal peptide removed in vivo by processes native to the transformant, yielding the exogenous gene product.

The expression plasmids may also include a second promoter, preferably the *E. coli* lac promoter, which is inserted immediately after the lipoprotein promoter so that the exogenous DNA is expressed only in the presence of a lactose inducer. However, when induced, the DNA coding for the desired polypeptide is transcribed from both promoters, thereby increasing the yield of the desired product. Accordingly, both constitutive and inducible gene expression may be achieved using the cloning vehicles of the present invention.

BRIEF DESCRIPTION OF DRAWINGS

The structure and function of the recombinant bacterial plasmids of the present invention, with which gene products such as human insulin may be expressed in bacterial transformants, is illustrated in the following specification, when taken in conjunction with the accompanying drawings wherein:

FIG. 1 is a schematic illustration of the 814 base pair DNA sequence encompassing the *E. coli* lipoprotein gene, in which the transcription initiation and termination sites are indicated by arrows (Δ), and in which the 78 amino acid sequence of the prolipoprotein deduced from the DNA sequence is also shown, written below the corresponding codons of the DNA coding strand;

FIG. 2 shows the complete 322-nucleotide sequence of the lipoprotein mRNA of *E. coli*, in which the amino acid sequence of the prolipoprotein deduced from the mRNA sequence is also indicated, written below the corresponding codons of the nucleotide sequence;

BEST MODE OF CARRYING OUT THE INVENTION

1. Summary Of Preliminary Research

Figure 3:
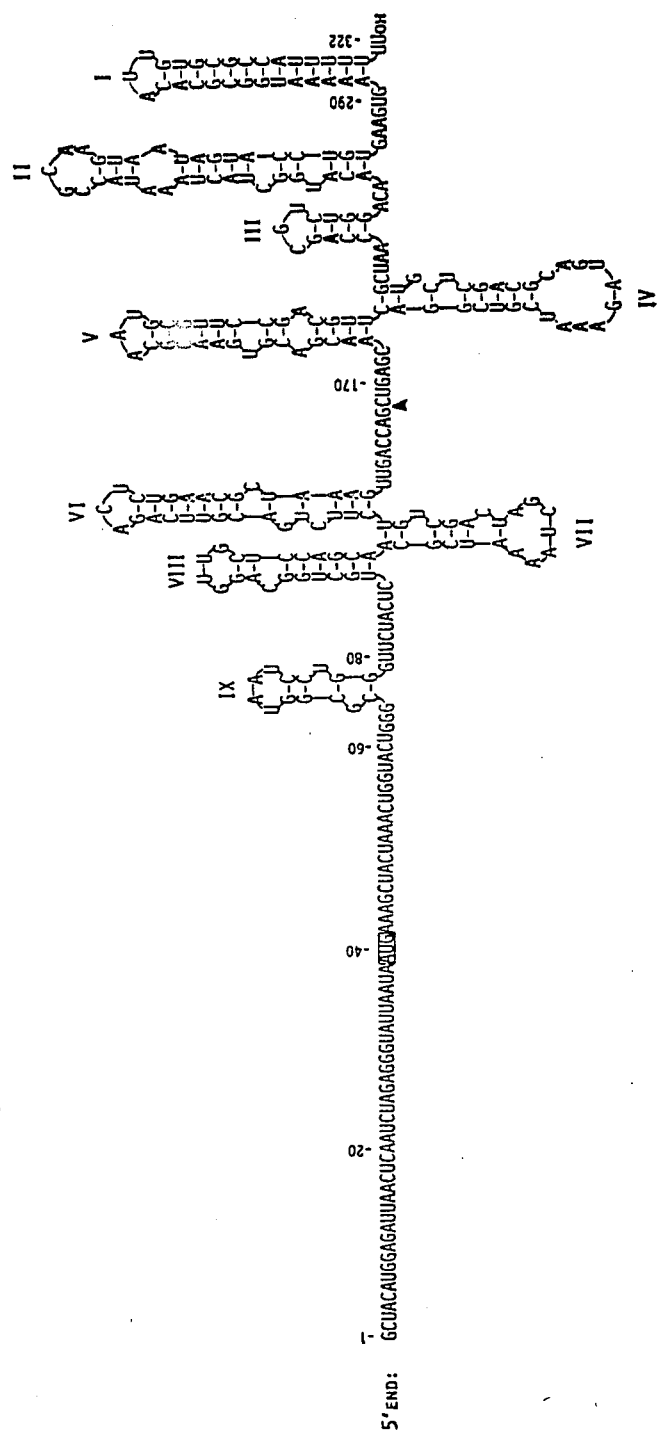
FIG. 3 illustrates the proposed secondary structure of *E. coli* lipoprotein mRNA, in which the translation initiation codon is boxed.

Recent investigation has shown that as a class, the major outer membrane proteins of gram-negative bacteria are present in rather large quantities in each bacterial cell. For example, it has been found that the *E. coli* lipoprotein, which is one of the most extensively investigated membrane proteins, is also the most abundant protein in the cell in terms of numbers of molecules, there being approximately 700,000–750,000 lipoprotein molecules per cell. Since it has also been shown that there is only one structural gene for the lipoprotein of *E. coli*, extremely efficient machinery for lipoprotein gene expression, at the levels of both transcription and translation, is indicated. It is believed that the lipoprotein gene may be expressed at least ten times more efficiently than genes for ribosomal proteins. The presence of comparable quantities of other major outer membrane proteins in *E. coli*, such as the ompA protein, and the presence of comparable quantities of the major outer membrane proteins in other gram-negative bacteria, such as the lipoprotein of *Serratia marcescens*, indicate that these systems may also have very efficient machinery for gene expression. Thus, while the discussion herein may refer in large part to the lipoprotein system in *E. coli*, it is to be understood that this invention extends to recombinant cloning vehicles which utilize the machinery for gene expression associated with all of the outer membrane protein genes of all gram-negative bacteria.

Although the mechanisms which are responsible for the highly efficient expression of the *E. coli* lipoprotein gene are not yet completely understood, it is believed that several factors must contribute to the abundance of lipoprotein molecules in a bacterial cell. As shown in FIG. 1, the DNA nucleotide sequence of the lipoprotein gene of *E. coli* has recently been determined, an analysis of which has revealed many unique properties associated with the expression of this gene.

In particular, it has been found that in comparison with other known promoter sequences of *E. coli* genes, the lipoprotein promoter region shows a most striking feature, namely, an extremely high A-T content, which is believed likely to be essential for highly efficient transcription of the lipoprotein gene. The segment of 261 base pairs ("bp") preceding the transcription initiation site (from position −261 through position −1 as shown in FIG. 1) has a very high A-T content of 70%, in contrast with 53% for the transcribed region (or mRNA region) of 322 base pairs (positions +1 to +322), 44% for a segment of 126 bp after the transcription termination site (positions +323 to +449), and 49% for the average A-T content of the *E. coli* chromosome. The A-T content of the segment from position −45 to position −1, within which the nucleotide sequence of the lipoprotein ("lpp") promoter appears to reside, is especially high (80%), and appears to be the highest among the *E. coli* promoter regions thus far sequenced. The A-T richness of the promoter sequence is considered to destabilize the helix structure of the DNA and thereby facilitate the RNA polymerase-mediated strand unwinding necessary for the initiation of transcription.

Apart from its A-T content, the lpp promoter also appears to contain a heptanucleotide sequence at positions −15 through −9 (only eight base pairs distal to the transcription initiation site) which is homologous to the generalized "Pribnow box" as well as a dodecanucleotide sequence at positions −38 through −27 which is homologous to the generalized "RNA polymerase recognition site." The homology of these sequences is striking, in that the Pribnow box sequence of the lpp promoter has only one base mismatching with the generalized sequence, while the recognition site sequence shows a mismatch of only 5 out of 12 bases of the generalized sequence. The importance of the specific base sequences at these sites for efficient transcription is well-documented, in that mutants with enhanced promoter efficiency show increased homology of these regions with the generalized sequences.

Further analysis of the DNA sequence of FIG. 1 has revealed that besides having an extremely "strong" promoter, the lipoprotein gene also has an oligo-T transcription termination signal, located between positions +316 and +322, which is at least as efficient as all other *E. coli* transcription termination sites that have been studied. It is believed that this factor contributes to the overall efficiency of transcription by hastening the rate of mRNA production, and by limiting the size of the mRNA molecule which is transcribed from the DNA.

As shown in FIG. 2, the complete nucleotide sequence of the *E. coli* lipoprotein mRNA has also been determined, revealing that the mRNA has several unique features in its structure which appear to be important for efficient translation of the mRNA transcript. The mRNA consists of 322 nucleotides, 38 of which are in the 5'-untranslated region and 50 of which are in the 3'-untranslated region, leaving 234 nucleotides in the translated region which code for the lipoprotein precursor, or prolipoprotein. The mRNA sequence of FIG. 2 is complementary to the DNA sequence of FIG. 1, with the exception of the nucleotide at position 313 which is shown as C in FIG. 2 as determined by RNA sequencing, rather than A as determined by the DNA sequencing shown in FIG. 1. The reason for this difference is not known at present.

The lipoprotein mRNA has been shown to be unusually stable, and it has been proposed that this stability is probably attributable to the formation of extensive secondary structures within the molecule. As shown in FIG. 3, the mRNA can form nine stable "hairpin" stem-and-loop structures (designated by Roman numerals I–IX), the most stable of which (I) is in the 3'-untranslated region. These secondary structures may be responsible for the longer functional half-life which has been observed for the lipoprotein mRNA in comparison with other *E. coli* mRNAs, and may thereby increase the availability of this molecule for ribosomal translation.

Furthermore, although 68% of the total nucleotides in the mRNA molecule are involved in the formation of the hairpin structures shown in FIG. 3, it should be noted that in the first 64 nucleotides from the 5' end there are no stable hairpin structures, whereas between the 65th nucleotide and the 3' end, 85% of the nucleotides are involved in the formation of hairpin structures. This is significant because in the 5'-untranslated region (positions +1 to +38) there appear to be two extensive inverted repeat sequences of nucleotides which are thought to prevent the formation of secondary structures in this region, allowing the ribosome-binding site in this segment to be fully exposed to ribosomes, thereby facilitating the initiation of translation. Moreover, the rate of initiation of translation is probably further facilitated by the presence of two possible ribosome binding sites in this region of the molecule.

Finally, the presence of all three translation termination codons in the 3'-untranslated region of the mRNA (UAA, positions +273 to +275, UAG, positions +276 to +278, and UGA, positions +285 to +287 [see FIG. 2]), all three of which are in the same reading frame as the translatable or "coding" region of the mRNA, provides a unique "back-up" sequence of tandem terminators which probably contributes to the overall efficiency of translation by assuring proper termination of translation in a "fail-safe" manner.

The cumulative effect of these as well as other unique features of the lipoprotein mRNA is believed to result in very efficient translation of this genetic information in *E. coli* cells.

Apart from the efficiency of its expression, another important aspect of the lipoprotein of *E. coli* is that it is a "secretory" protein, i.e., it is produced from a precursor, which is then secreted across the cytoplasmic membrane and processed to the lipoprotein. Thus, translation of the lipoprotein mRNA transcript actually yields this precursor, called the prolipoprotein, which has a peptide extension or signal peptide at its amino terminus, consisting of 20 amino acid residues whose sequence has been determined, followed by the known 58 amino acid sequence of the lipoprotein. While the mechanisms involved in the secretion process are not yet well understood, the signal peptide is considered to direct the translocation in vivo of the prolipoprotein across the cytoplasmic membrane, in the process of which the peptide extension itself is removed, yielding mature lipoprotein.

It is believed that analogous elaboration processes are involved in the production of the major outer membrane proteins of all gram-negative bacteria. For example, an analysis and comparison of the DNA sequence of the *Serratia marcescens* ("*S. marcescens*") lipoprotein gene with that of the *E. coli* lpp gene has revealed striking homologies in the promoter region (84%) and in the 5'-untranslated region (95%). Moreover, the A-T content in the promoter region of the *S. marcescens* lipoprotein gene is extremely high (78%), as found in the case of the *E. coli* lipoprotein gene (80%). Furthermore, although the DNA sequence coding for the peptide extension of the prolipoprotein of *S. marcescens* differs somewhat from that of *E. coli*, the resultant alterations in the amino acid sequence do not change the basic properties of the signal peptide as proposed for the *E. coli* prolipoprotein and for other bacterial secretory proteins. In addition, the lipoprotein mRNA of *S. marcescens*, as deduced from the DNA sequence, seems capable of forming seven stable hairpin stem-and-loop structures. The existence of the lipoprotein in many different genera of gram-negative bacteria has now been confirmed, and it has been found that the *E. coli* lipoprotein mRNA hybridizes with DNAs from at least the following seven bacterial species (besides *S. marcescens*) in the family Enterobacteriaceae: *Shigella dysenteriae, Salmonella typhimurium, Citrobacter freundii, Klebsiella aerogenes, Enterobacter aerogenes, Edwardsiella tarda*, and *Erwinia amylovora*, thereby confirming a degree of homology of the lipoprotein gene between *E. coli* and other gram-negative bacteria. The extension of the present invention to recombinant plasmid cloning vehicles utilizing analogous and highly efficient machinery for gene expression derived from any gram-negative bacterium is believed justified by all of these as well as other findings.

The unique characteristics of the biosynthesis and assembly of the outer membrane proteins of gram-negative bacteria, as discussed above, make the lipoprotein genes and other major outer membrane protein genes of these organisms extremely attractive vehicles with which to control the expression of exogenous DNA insert fragments in bacterial transformants. In this application, the structure and function of several such cloning vehicles is described.

2. Strategy For Constitutive Gene Expression

Figure 4:
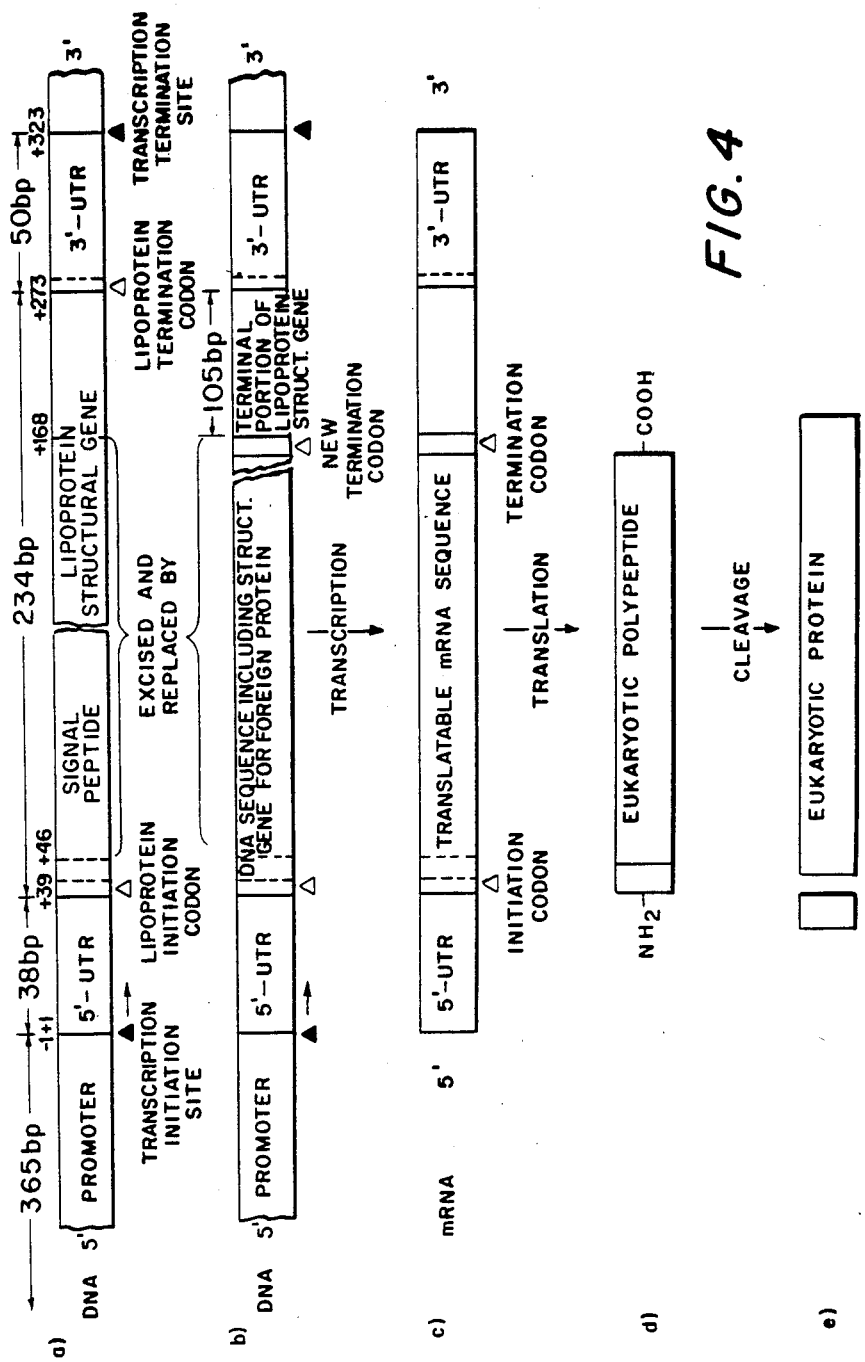
FIG. 4 is a schematic outline of the process by which eukaryotic protein or other desired polypeptide may be expressed using the cloning vehicles of the present invention, in which the transcription initiation and termination sites are indicated by arrows (Δ) and the translation initiation and termination sites are indicated by arrows (Δ)

It will be apparent from the foregoing discussion that a majority of the features which appear to be responsible for the efficient transcription and translation of the lipoprotein gene of *E. coli* reside in the functional fragments of the gene, namely, the promoter, the 5'-untranslated region, the 3'-untranslated region, and the transcription termination site, all of which are located either "upstream" or "downstream" of the lpp structural gene, as shown in FIG. 4, line a. Hence, by inserting a structural gene for a eukaryotic protein or other desired polypeptide in an expression plasmid containing various combinations of the foregoing functional fragments, and by transforming a bacterial host with such a plasmid, the transcription and subsequent translation of the structural gene can be made to take place under the control of those functional fragments.

For reasons which will be evident to those skilled in the art, it is particularly desirable and advantageous to utilize all of the foregoing functional fragments together in tandem in a single expression plasmid. By fusing the structural gene for the desired polypeptide at its 5' end to a DNA sequence comprising both the promoter and the 5'-untranslated region of the *E. coli* lpp gene (most preferably, this DNA sequence also includes the entire 260 bp A-T rich DNA segment preceding the transcription initiation site), highly efficient transcription is achieved by utilizing one of the strongest bacterial promoters, and highly efficient translation is achieved by utilizing a DNA sequence which can code for features which facilitate the initiation of translation, including the most effective ribosome binding site. Moreover, by fusing the structural gene at its 3' end to a DNA sequence comprising the 3'-untranslated region and the transcription termination signal of the *E. coli* lpp gene, the efficiency of transcription is believed to be further enhanced, avoiding transcriptional "read-through" (the synthesis of an unnecessarily long 3'-untranslated region in the mRNA) and more importantly, facilitating the rate of mRNA production. The stability of the mRNA molecule is also augmented by the formation of secondary structure in the 3'-untranslated region.

As described in detail hereinbelow, the secretory nature of the lipoprotein can be utilized to control yet another aspect of the expression of a eukaryotic protein or other desired polypeptide, namely, the location at which the expression product can be expected to be found. Depending upon the site within the lpp gene chosen for insertion of the exogenous DNA, the expression product can be expected to accumulate either within the cytoplasm of the transformant cell, within the periplasmic space, or in the cell's outer membrane.

FIG. 4 schematically illustrates a process wherein a transformant organism expresses a natural eukaryotic protein in accordance with the foregoing scheme. In the particular embodiment illustrated in FIG. 4, the structural gene for the eukaryotic protein is inserted within the signal peptide of the lpp gene, several base pairs after the translation initiation codon and downstream of certain functional fragments (namely, the promoter and the 5'-untranslated region) normally associated with the lip gene. As will be seen by comparing line a with line b in FIG. 4, the orientation of these functional fragments is identical to the natural orientation of these elements in the lipoprotein gene, while the exogenous DNA insert fragment supplants most of the signal peptide as well as a portion of the structural region of the lipoprotein gene.

As shown in FIG. 4, line b, the foreign gene is linked at its 3' end to an extra translation termination codon, which is in turn fused to the remainder of the lipoprotein structural gene. This is linked still further downstream in the normal manner to the 3'-untranslated region of the lpp gene, which ends with the transcription termination site. As can be seen by again comparing line a with line b in FIG. 4, the functional fragments which follow the DNA insert fragment are essentially identical to those which are present normally in the lipoprotein gene.

The 3'-untranslated region derived from the lpp gene codes for an mRNA sequence capable of forming the stem-and-loop structure designated by the numeral I in FIG. 3, which, as discussed previously, is the most stable secondary structure in the lipoprotein mRNA. However, the recombinant DNA sequence depicted schematically in FIG. 4, line b, also includes a terminal portion of the lipoprotein structural gene consisting of 105 base pairs starting with position +168 (this position is designated by the arrow ($\Delta$) in 3). This region is chosen so that the stability of the mRNA transcript can be further enhanced by including four additional stem-and-loop structures (designated by the numerals II, III, IV and V in FIG. 3), without unduly increasing the size of the mRNA molecule produced. However, as set forth below, this region is not ultimately translated.

Transcription of the recombinant DNA sequence illustrated in FIG. 4, line b, yields an mRNA sequence which is illustrated schematically in FIG. 4, line c. It will be seen that this sequence contains the 5'-untranslated region and the 3'-untranslated region, bottom of which are normally associated with the production of the lipoprotein. However, the mRNA also incorporates a region coding for the eukaryotic protein, preceded by a region which codes for a short segment of the signal peptide of the prolipoprotein, and followed by another region which codes for a segment of the lipoprotein. The latter region ultimately will not be translated, however, due to the insertion of a termination codon (designated by an arrow ($\Delta$) in FIG. 4, lines b and c) at the 3' of the eukaryotic structural gene. Following translation, a polypeptide is produced comprising several extraneous amino acid residues, followed by the amino acid sequence of the desired eukaryotic protein (see FIG. 4, line d). This conjugate expression product can be expected to accumulate within the cytoplasm of the cell, because secretion can not occur in the absence of a complete signal peptide. However, for certain proteins, the expression product can be purified from the cytoplasm in a known manner, and the superfluous protein fragment may then be separated and removed from the natural protein product by known techniques (see FIG. 4, line e), yielding the desired polypeptide which may then be stored for future use.

Alternatively, the DNA sequence coding for the extraneous amino acids can be excised from the expression plasmid in a known manner prior to transformation of the bacterial host, such that the expression product corresponds exactly with the desired foreign protein and may be purified by known techniques.

In an alternative embodiment of the foregoing scheme, the same functional fragments are used, but the DNA sequence coding for the desired polypeptide is inserted further downstream, following the last codon of the signal peptide (i.e., at or near the signal peptide cleavage site). It will be apparent to those skilled in the art that in this embodiment, the orientation of the functional fragments is once again identical to the natural orientation of these elements in the lipoprotein gene, allowing full advantage to be taken of the efficiencies of transcription and translation associated therewith, including the enhanced stability of the mRNA transcript attributable to the incorporation of four additional stem-and-loop structures, as described hereinabove.

The transcription and ultimate translation of such a recombinant DNA sequence proceeds in a manner analogous to that described hereinabove and illustrated in FIG. 4, except that following translation, a polypeptide is produced comprising a signal peptide corresponding to the signal peptide of the prolipoprotein, followed by the amino acid sequence of the desired eukaryotic protein. This precursor product can then be secreted across the cytoplasmic membrane under the control of the signal peptide, in the process of which the peptide extension itself may be recognized and removed by enzymatic action natural to the *E. coli* transformant cell, yielding a product consisting of the natural eukaryotic protein, perhaps with several extraneous amino acid residues at the amino terminus which can be removed as discussed hereinabove. This product accumulates initially in the periplasmic space, and may ultimately pass through the cell's outer membrane and into the culture medium provided that certain *E. coli* transformant strains are used, as set forth in more detail hereinbelow.

Using this approach, the accumulation of a large amount of the expression product inside the cell is less likely to interfere with cell growth, because the eukaryotic protein is linked with a signal peptide which is natural to the cell. Furthermore, the presence of the signal peptide may protect the foreign protein from possible degradative action inside the cell, which could otherwise lower the protein yield and could also cause contamination of the foreign protein by heterogenous degradative products, resulting in purification difficulties.

In yet another alternative embodiment of the foregoing scheme, the same functional fragments are again used, but the DNA sequence coding for the desired polypeptide is inserted still further downstream, for example, as illustrated herein, following the codon for the eighth amino acid residue after the signal peptide cleavage site. It will be apparent to those skilled in the art that in this embodiment, the orientation of the functional fragments is once again identical to the natural orientation of these elements in the lipoprotein gene, allowing full advantage to be taken of the efficiencies of transcription and translation associated therewith, including the enhanced stability of the mRNA transcript attributable to the incorporation of four additional stem-and-loop structures, as described hereinabove.

The transcription and ultimate translation of such a recombinant DNA sequence proceeds in a manner analogous to that described hereinabove and illustrated in FIG. 4, except that following translation, a polypeptide is produced comprising a signal peptide of 20 amino acid residues, corresponding to the signal peptide of the prolipoprotein, followed by eight amino acid residues corresponding to the first eight amino acid residues of the mature lipoprotein, followed by the amino acid sequence of the desired eukaryotic protein. As with the embodiment previously described, this precursor product may be translocated naturally across the cytoplasmic membrane, in the process of which the signal peptide can be recognized and removed. However, the product may not accumulate in the periplasmic space; instead, the eight amino acids corresponding to the lipoprotein can be recognized, and the expression product may then be processed further and inserted into the outer membrane of the cell in a manner analogous to the normal insertion of the lipoprotein into the outer membrane. If as expected, only the first eight amino acid residues of the expression product corresponding to the lipoprotein are actually bound into the outer membrane, then the remainder of the expression product, consisting of the amino acid sequence of the eukaryotic protein or other desired polypeptide, will protrude from the outer membrane, such that, for certain proteins, the membrane may be isolated and the desired protein purified from the membrane easily.

It will therefore be evident to those skilled in the art that by constructing a plasmid cloning vehicle according to the present invention with one or another of the three insertion sites described above, and by using such a plasmid to express an exogenous gene product, the location of that product can be predicted with a reasonable degree of certainty, and the appropriate methods for isolating and purifying that product will thereby be suggested. The choice of insertion site will often be dictated by the identity and structure of the desired polypeptide itself, especially if the method of purification most appropriate for that product is known.

In order to facilitate still further the expression of a wide variety of exogenous DNA fragments using the cloning vehicles of the present invention, a short polynucleotide sequence containing the recognition sites for the Eco RI, Hind III and Bam HI restriction enzymes can be incorporated at the insertion site in each expression plasmid. This allows additional flexibility, in that six different types of restriction fragments can be inserted into each plasmid according to the straightforward and well-known techniques described herein above. Thus, DNA insert fragments tailored to have any one of the following pairs of cohesive termini can be readily used with the present invention: Eco RI-Eco RI, Hind III-Hind III, Bam HI-Bam HI, Eco RI-Hind III, Eco RI-Bam HI and Hind III-Bam HI.

It is to be understood that virtually any structural gene coding for a desired polypeptide, including mammalian and human hormones, enzymes and immunogenic proteins (or intermediates therefor), may be expressed using the recombinant plasmids of the present invention. Examples of such proteins include A-chain insulin, B-chain insulin, proinsulin, growth hormone, somatostatin, interferon and trypanosome antigen, but the invention is not confined to these exemplary products.

3. Strategy For Inducible Gene Expression

As mentioned hereinabove, the expression of genetic information is termed inducible if transcription cannot be initiated in the absence of a certain molecule. Inducible gene expression is exemplified in nature by the *E. coli lac* promoter-operator, which controls the production of $\beta$-galactosidase, an important enzyme in lactose digestion. Normally, the expression of this gene is "switched off" by the presence of a lactose repressor, which binds to the lac promoter-operator, preventing interaction between RNA polymerase and the promoter sequence and thereby inhibiting transcription (and subsequent translation) of the $\beta$-galactosidase structural gene. In the presence of lactose, however, the repressor molecule is removed from the DNA and the gene is "switched on," allowing transcription to proceed until a sufficient quantity of the $\beta$-galactosidase enzyme is produced to digest the lactose, after which the repressor again "switches off" the gene.

The constitutive lpp gene cloning vehicles described hereinabove can be made inducible by inserting the lac promoter downstream of the lpp promoter, but upstream of the exogenous DNA insert fragment. In this configuration, transcription of the foreign DNA from either promoter is blocked by the repressor molecule and cannot proceed in the absence of a substance, termed a "lactose inducer," which for present purposes is a molecule that reacts with and alters the lactose repressor molecule such that the repressor molecule can no longer bind to the lac promoter-operator. When induced with lactose or with a synthetic inducer, IPTG, however, the foreign DNA can be transcribed from both the lpp and lac promoters independently, allowing approximately five times higher gene expression than would occur using the lac promoter alone.

It is to be understood that all of the desirable features described hereinabove in connection with the constitutive lpp gene expression plasmids may be incorporated with equal advantage in the inducible lpp gene expression plasmids of the present invention. These include the efficiencies of transcription and translation usually associated with the four specified functional fragments of the lpp gene, the enhanced stability of the mRNA transcript attributable to the incorporation of the four additional stem-and-loop structures associated with the mRNA transcript of the terminal portion of the lipoprotein structural gene, the provision of three different insertion sites for the foreign DNA to control the location at which the expression product can be expected to be found, and the incorporation of Eco RI, Hind III and Bam HI restriction enzyme recognition sequences at the exogenous DNA insertion site in each plasmid to facilitate the expression of a wide variety of DNA insert fragments.

While the discussion herein may refer in large part to the creation of inducible expression plasmids by incorporating therein a second promoter fragment which is itself inducible, it is to be understood that this invention extends to recombinant plasmid cloning vehicles which utilize a second promoter, whether or not inducible, in tandem with the machinery for gene expression associated with an outer membrane protein gene of a gram-negative bacterium.

4. The Transformant

In the preferred embodiment of the present invention, the constitutive recombinant cloning vehicles incorporating the gene for the desired eukaryotic protein or other polypeptide are used to transform special *E. coli* strains as hosts for cloning and for subsequent production of the protein. The host cell strains used will be chosen to have a "deletion mutant" in the lpp gene, so that the host cells cannot produce the lipoprotein. The use of a deletion mutant strain as the transformant is thought to stimulate the production of a large amount of the foreign protein, since the entire capacity of the host cells to produce the lipoprotein is thereby channelled towards production of the foreign protein. Furthermore, secretion of the foreign protein across the cytoplasmic membrane is facilitated in lpp-defective host cells, since the secretion sites in the membrane which are intended to be used for lipoprotein secretion are instead available for secretion of the foreign protein.

The use of the lpp-defective cells is especially beneficial when the gene coding for the foreign protein is inserted at or near the lipoprotein signal peptide cleavage site. This is because such cells are known to be "leaky", i.e., proteins secreted across the cytoplasmic membrane of such cells ultimately "leak" out into the culture medium through the outer membrane of the cell. This is believed to be desirable not only because release of the desired foreign protein into the culture medium may in some cases allow easier isolation and purification of the foreign protein than would be possible if the foreign protein remained inside the cell, but also because the foreign protein would otherwise accumulate in the periplasmic space, perhaps leading to undesirable interference with normal cellular activities or cell growth. Secretion of the desired eukaryotic gene product outside the cell may also avoid degradation of that product into smaller fragments by proteolitic enzymes which are normally present within the cell.

For the inducible cloning vehicles, it is also preferable to use special *E. coli* strains as transformants, specifically, those which can overproduce the lactose repressor molecule. In the wild-type *E. coli* cell, only about 10 copies of the lactose repressor molecule are maintained in the cell at any one time, which is just enough to repress (i.e., inhibit transcription from) the one lac promoter-operator normally contained in the cell. This is insufficient, however, to block the expression of the exogenous DNA cloned in an inducible lpp gene expression plasmid of the present invention, since 10 to 20 copies of the cloning vehicle, each containing an active lac promoter, may exist in each cell at a given time. Therefore, much larger amounts of the lactose repressor are required, and for this purpose, the strain used for transformation is preferably a special *E. coli* strain JA221F' lacIq lac+ pro+, which carries the mutant lacIq gene. The lacIq gene is a mutant of lacI, the "normal" gene coding for the lactose repressor. The mutant gene overproduces the lactose repressor, providing about 100-150 molecules/cell at any given time. The lacIq gene is carried on a plasmid F-prime in this *E. coli* strain.

5. Experimental

The strategy and techniques described hereinabove applied experimentally to construct a group of recombinant bacterial plasmid cloning vehicles according to the present invention. Two types or "families" of vehicles were constructed, one for constitutive gene expression (labelled the "pIN-I" type), and the other for inducible gene expression (the "pIN-II" type).

Figure 5:
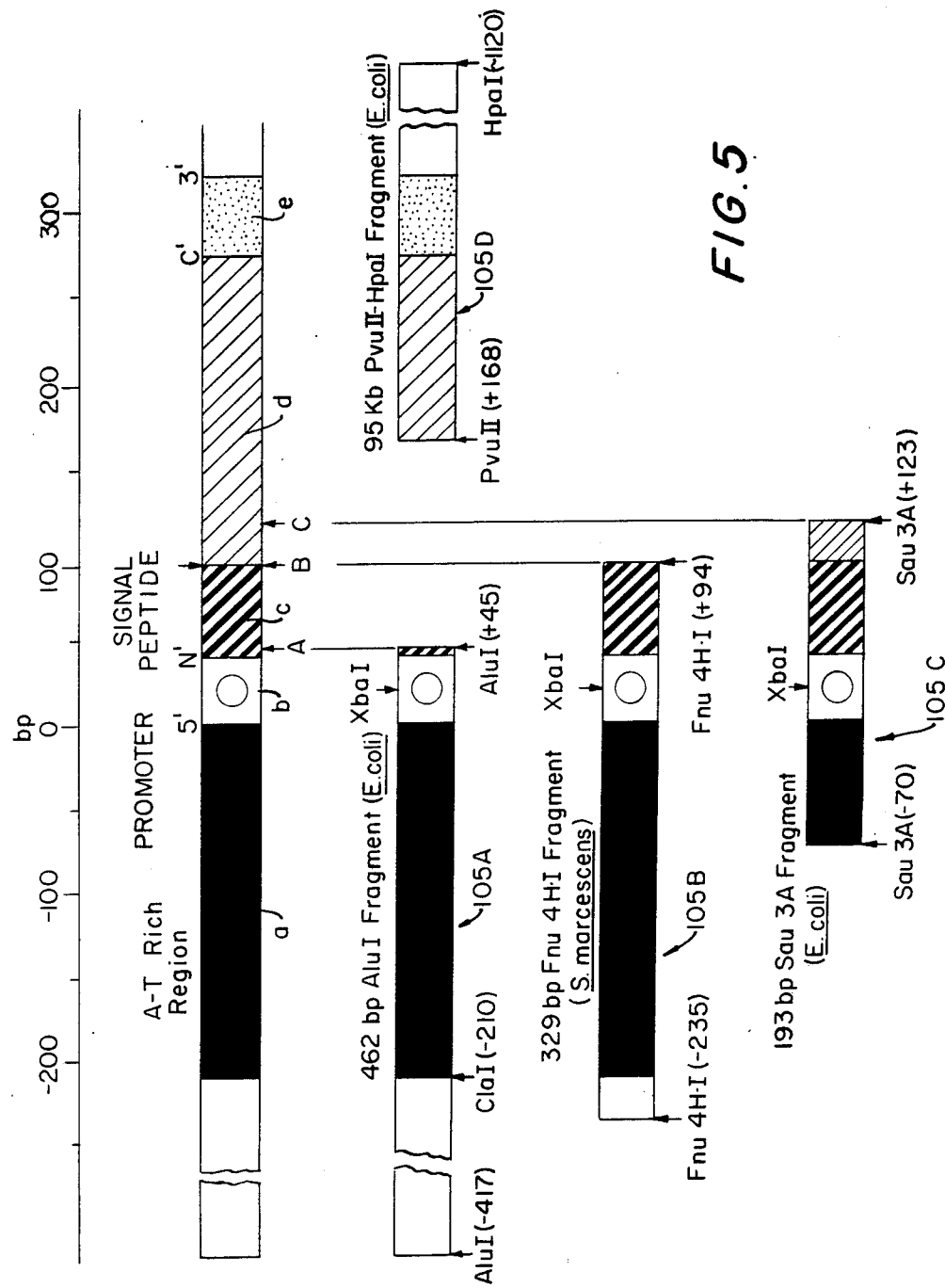
FIGS. 5–27 together comprise a schematic illustration of the preferred method for construction of the recombinant plasmid cloning vehicles of the present invention, in which the relative positions of various restriction endonuclease cleavage sites are shown, and in which Amp$^r$ and Tc$^r$, respectively, denote genes for ampicillin and tetracycline resistance.

In the remainder of this application, the insertion site located within the DNA sequence coding for the prolipoprotein signal peptide will be designated the "A" site, while the insertion site located immediately after the last codon of the signal peptide will be labelled the "B" site, and the insertion site located after the codon for the eighth amino acid residue of the mature lipoprotein will be referred to as the "C" site (see FIG. 5). For each site, three plasmids were prepared (one corresponding to each of the three possible reading frames), yielding a total of nine expression plasmids in each family which were labelled A-1, A-2, A-3, B-1, B-2, B-3, and C-1, C-2, C-3.

The restriction enzymes used herein were obtained from New England Biolabs and Bethesda Research Laboratories. T4 DNA ligase was obtained from Bethesda Research Laboratories, and S1 Nuclease was obtained from Miles Laboratories.

A. Construction Of A Site Plasmids (pIN-I)

FIGS. 6-15 schematically depict the manner in which recombinant plasmids incorporating the A insertion site were constructed, and may be referred to in connection with the following more particularized discussion.

1. Construction Of Plasmid pKEN111

The first step in the construction of the A site lpp cloning vehicles was to construct a plasmid to serve as a source of lpp gene components in subsequent steps of the procedure. The plasmid chosen to receive the *E. coli* lpp gene for this purpose was pSC101, a small (molecular wt. approximately 5.8 megadaltons) plasmid carrying a gene conferring resistance to the antibiotic tetracycline (Tc) (Cohen, S. N., et al., *J. Bacteriol.* 132: 734-737 [1977]). As shown at 100 FIG. 6, pSC101 includes a cleavage site for the restriction endonuclease Eco RI located at the 5' end of the tetracycline resistance gene. The plasm pSC101 was obtained from Dr. E. Ohtsubo at the Department of Microbiology, State University of New York at Stony Brook.

As shown schematically at in 101 in FIG. 6, 2 micrograms of plasmid pSC101 DNA were digested to completion with two units of the restriction endonuclease Eco RI in 50 microliters of a reaction mixture comprising 100 mM Tris:HCl (pH 7.5), 75 mM NaCl, 6 mM MgCl$_2$, 6 mM β-mercaptoethanol and 100 micrograms/ml bovine serum albumin (hereinafter "BSA") (this reaction mixture will hereinafter be referred to as an "Eco RI buffer") at 37° C. for 60 minutes. To prevent self-ligation of the Eco R pSC101 DNA, bacterial alkaline phosphatase (hereinafter "BAP") was added (0.1 units of Worthington BAPF), and incubation was continued for 60 minutes at 37° C. The reaction was terminated by phenol extraction, and the linearized DNAs were recovered by ethanol precipitation.

Figure 6:
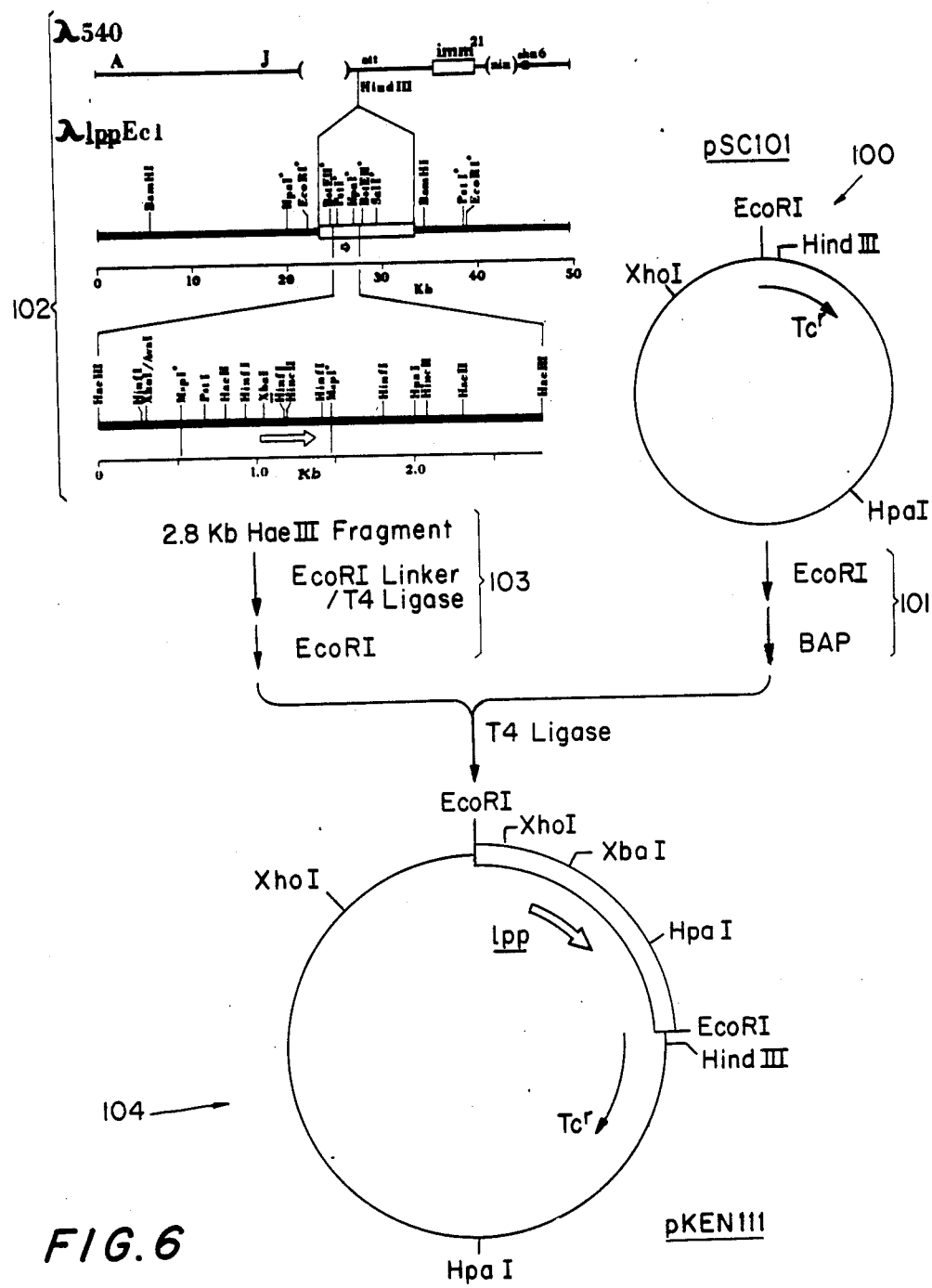

A 2.8 kilobase ("Kb") DNA fragment containing the E. coli lpp gene was separately derived, as shown at 102 FIG. 6, from a hybrid λ phage carrying the E. coli lpp gene (designated λlppEc-1. The lpp gene had previously been cloned into a λ phage vector, λ540 (Murray and Murray, J. Mol. Biol. 98: 551–564 [1975]), as follows: Total DNA (200 micrograms) isolated from an E. coli K-12 strain merodiploid for the lpp gene (JE5519/F506 [Movva, N. R., et al., J. Bacteriol. 133: 81–84 (1978)]) was digested with 200 units of the restriction enzyme Hind III. DNA fragments were separated on a preparative agarose gel, and fractions of DNA fragments of approximately 10 Kb which showed positive hybridization with 5'-$^{32}$P-lipoprotein mRNA were collected, using the Southern hybridization technique (J. Mol. Biol. 98: 503–517). A mixture of 10 Kb Hind III fragments (enriched approximately twenty-fold) and Hind III-cleaved λ540 vector DNA was reacted with T4 DNA ligase. Ligated DNA was used to transfect E. coli K802, NRRL B-15016 (obtained from Dr. F. R. Blattner at the Laboratory of Genetics, University of Wisconsin-Madison). This strain is available to the public from the permanent collection of the Northern Regional Research Laboratory, U.S. Department of Agriculture, Peoria, Ill., U.S.A. Recombinant phages carrying the lpp gene were screened by the plaque hybridization technique of Benton and Davis (Science 196: 180–182 [1977]) using 5'-$^{32}$P-lipoprotein mRNA. One of the plaques examined which gave positive hybridization was found to carry a fully functional lpp gene, and was designated λlppEc-1.

Two hundred micrograms of λlppEc-1 DNA were then digested completely with 200 units of the restriction enzyme Hae III in 500 microliters of a reaction mixture containing 6 mM Tris:HCl (pH 7.5), 6 mM MgCl$_2$, 6 mM NaCl, 6 mM βmercaptoethanol and 100 micrograms/ml BSA (the foregoing reaction mixture will hereinafter be referred to as a "Hae III buffer") at 37° C. for 2 hours, and the 2.8 Kb Hae III fragment carrying the E. coli lpp gene was purified by fractionation on a 5% polyacrylamide gel according to the following procedure: The reaction mixture was first extracted with phenol, and the DNA fragments were then precipitated with 2.5 volumes of ethanol, dried under vacuum, dissolved in 200 microliters of a buffer comprising 5% glycerol, 20 mM EDTA, 0.05% bromophenol blue and 0.05% xylen cyanol (this mixture will hereinafter be referred to as a "gel buffer") and thereafter fractionated on a 5% polyacrylamide gel. The DNA band which had migrated to a 2.8 Kb position was excised from the gel, and the DNA fragments were eluted from the gel by electrophoresis. Ethidium bromide dye, used to locate the DNA band in the gel, was removed from the DNA fragments by phenol extraction. The DNA fragments were precipitated with 2.5 volumes of ethanol, centrifuged, dissolved in 200 microliters of 0.3 M Na-acetate, re-precipitated with 0.5 ml of ethanol and dried again under vacuum. Approximately 10 micrograms of a purified 2.8 Kb Hae III fragment were recovered.

In order to clone the 2.8 Kb Hae III fragment into pSC101, synthetic "Eco RI linker" molecules were attached to the termini of the 2.8 Kb Hae III fragment, as shown schematically at 103 in FIG. 6. The Eco RI linker (5'GGAATTCC3'; obtained from Collaborative Research) was phosphorylated by T4 polynucleotide kinase (obtained from P.L. Biochemicals) with ATP in 50 microliters of a reaction mixture containing 3 moles of the linker, 66 mM Tris:HCl (pH 7.5), 10 mM MgCl$_2$, 10 mM β-mercaptoethanol, 60 μM ATP and 10 units of T4 polynucleotide kinase. After the mixture was incubated at 37° C. for 30 minutes, it was heated at 60° C. for 10 minutes, and cooled to 37° C. Five microliters of 0.1 M β-mercaptoethanol and 10 units of T4 polynucleotide kinase were added to the mixture, and the reaction was continued at 37° C. for 30 minutes. The reaction was terminated by freezing the mixture in a dry ice-ethanol bath.

The 2.8 Kb Hae III fragment (2 micrograms) was mixed with 150 pmoles of phosphorylated Eco RI linker and was treated with 4 units of T4 DNA ligase in 12.5 microliters of a reaction mixture containing 66 mM Tris:HCl (pH 7.5), 10 mM MgCl$_2$, 10 mM dithiothreitol (the foregoing reaction mixture will hereinafter be referred to as a "ligase buffer") and 0.6 mM ATP at 12.5° C. for 15 hours. The reaction was terminated by diluting the mixture twenty-fold with Eco RI buffer and by heating the mixture at 60° C. for 10 minutes. Thirty units of the restriction enzyme Eco RI were added, and the mixture was incubated at 37° C. for one hour to create Eco RI cohesive termini. The reaction was terminated by heating at 60° C. for 10 minutes.

The mixture thus obtained was added to 2 micrograms of the previously-linearized plasmid pSC101 DNA, and phenol extraction was performed. After extraction with ether, the DNAs were precipitated with ethanol, dried under vacuum, and dissolved in 100 microliters of ligase buffer. The mixture was heated at 37° C. for 5 minutes, and the Eco RI cohesive termini were annealed by incubating at 4° C. for 16 hours and then at 0° C. for one hour. After adding ATP (0.4 mM final) and 1 unit of T4 DNA ligase, the mixture was incubated at 12.5° C. for 7 hours.

One-fourth of the ligation mixture was thereafter used to transform E. coli lpp deletion mutant strain JE5527, NRRL B-15012 (F-, man, lpp-2, pps, thi, his, rpsL, gyrA, recA1 [Hirota, Y., et al., Proc. Natl. Acad. Sci. U.S.A. 74: 1417–1420 (1977)], obtained from Dr. Y. Hirota, National Institute of Genetics, Mishima, Japan). This strain is available to the public from the permanent collection of the Northern Regional Research Laboratory, U.S. Department of Agriculture, Peoria, Ill., U.S.A. Transformation was carried out as described in Cohen, S. N., et al., Proc. Natl. Acad. Sci. U.S.A. 69: 2110–2114 (1972), and tetracycline-resistant transformants were grown overnight on Whatman 3 MM filter papers, placed on the surface of an L broth plate containing 10 micrograms/ml of tetracycline, and screened for lpp clones by colony hybridization (Gergen, J.P., et al., Nucleic Acids Res. 7: 2115–2136 [1977]). A 0.95 Kb Msp I fragment of λlppEc-1 containing the lpp gene was nick-translated with [α-$^{32}$P]dATP and [α-$^{32}$P]dCTP, as described in Maniatis, T., et al., Proc. Natl. Acad. Sci. U.S.A. 72: 1184–1188 (1975), and was used as a $^{32}$P-probe. One of the transformants which gave positive hybridization was shown to contain the plasmid with the structure illustrated at 104 in FIG. 6, and this plasmid was designated pKEN111. This plasmid is obtainable from E. coli CC620/pKEN111, NRRL B-15011, which is available to the public from the permanent collection of the Northern Regional Research Laboratory, U.S. Department of Agriculture, Peoria, Ill., U.S.A. The plasmid can be obtained from NRRL B-15011 by conventional means.

2. Construction Of Plasmid pKEN008

Figure 7:
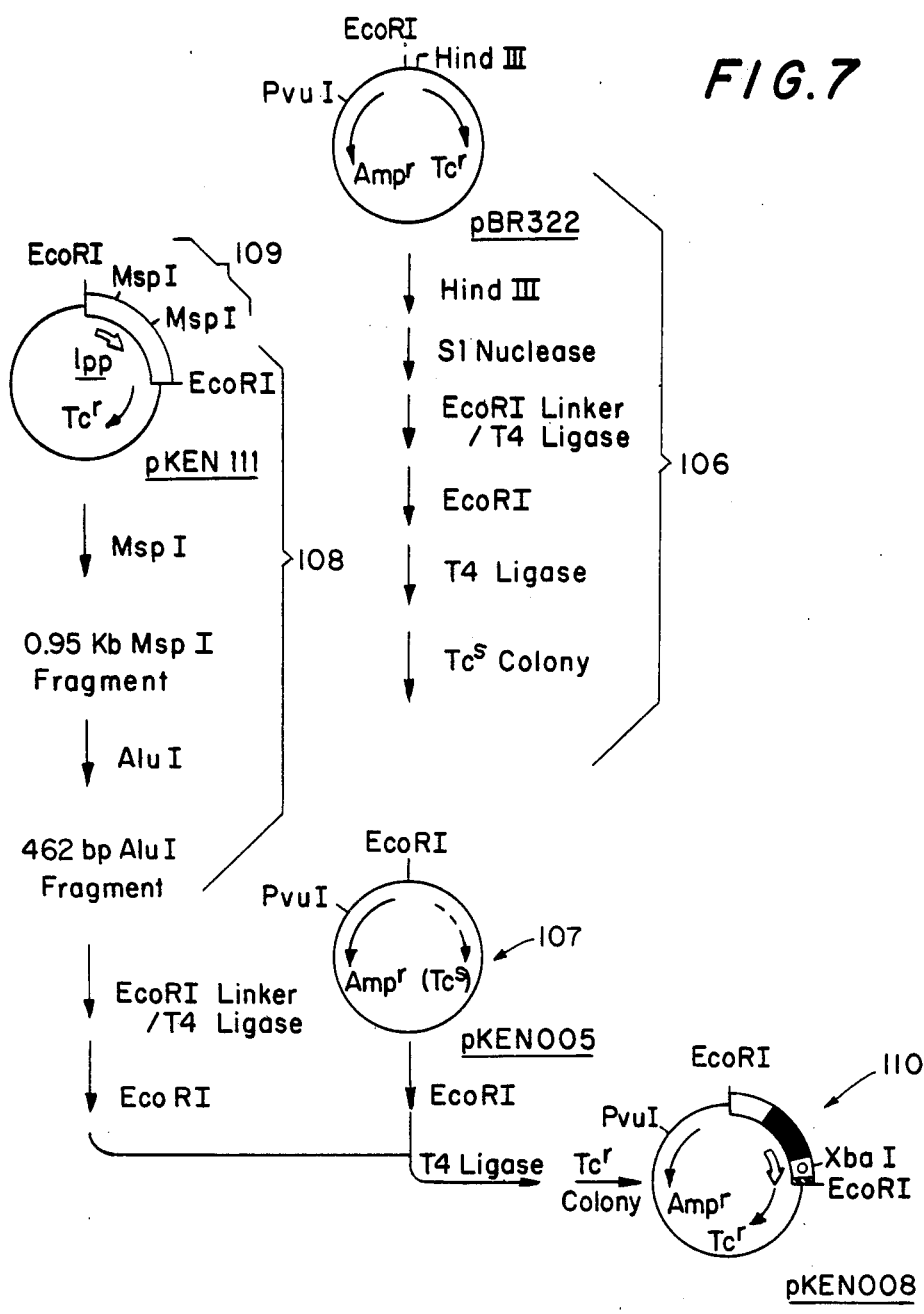

The parental plasmid chosen for construction of the lpp gene expression plasmids of the present invention was pBR322 (molecular wt. approximately 2.6 megadaltons), carrying genes conferring resistance to the antibiotics ampicillin (Amp) and tetracycline (Tc) (Bolivar, F., et al., *Gene* 2: 95–113 [1977]). As shown in FIG. 7, pBR322 includes an Eco RI cleavage site located at the 5' end of the tetracycline resistance gene, as well as a Hind III cleavage site located within the promoter of the tetracycline resistance gene and a Pvu I cleavage site located within the ampicillin resistance gene. The plasmid pBR322 was obtained from Dr. N. Arnheim of the Department of Biochemistry, State University of New York at Stony Brook, and is commercially available. from Bethesda Research Laboratories.

FIG. 5 illustrates schematically the various components of the lpp gene, each of which is identified by a symbol or shading. Specifically, the shaded segment indicated by the letter "a" identifies the A-T rich region of approximately 260 base pairs preceding the transcription initiation site and containing the lpp promoter. The 5'-untranslated region is identified by the segment containing the circular device and marked with the letter "b". The signal peptide region of the prolipoprotein is identified by the diagonally hatched and shaded segment "c". The structural region of the lpp gene is identified by the diagonally hatched segment labelled with the letter "d", while the speckled segment "e" identifies the 3'-untranslated region and the transcription termination site. These symbols and shading are used in a like manner to identify the same functional fragments of the lpp gene in FIGS. 7–11, 15, 17–18, 21–23, 26 and 27.

FIG. 7 illustrates the strategy used for inserting a fragment carrying the promoter and the 5'-untranslated region of the lpp gene into pBR322. The fragment chosen for this purpose was a 462 bp Alu I fragment of pKEN111 which, as shown schematically at 105A in FIG. 5, contains not only the promoter sequence and the 5'-untranslated region (positions −45 to −1 and +1 to +39, respectively) of the lpp gene, but also the entire extremely A-T rich segment preceding the promoter sequence.

In order to clone the 462 bp Alu I fragment containing the lpp promoter region in pBR322, the DNA fragment lying between the Eco RI and Hind III cleavage sites of pBR322 (containing the promoter of the tetracycline resistance gene) was first deleted, as shown schematically at 106 in FIG. 7, using the following procedure 11 micrograms of pBR322 plasmid DNA were digested with 11 units of Hind III restriction endonuclease in 200 microliters of a reaction mixture comprising 10 mM Tris:HCl (pH 7.5), 10 mM MgCl$_2$, 60 mM NaCl, 6 mM β-mercaptoethanol and 100 micrograms/ml BSA (this reaction mixture will hereinafter be referred to as a "Hind III buffer") at 37° C. for one hour. After digestion was completed, phenol extraction was performed, and DNAs were recovered by ethanol precipitation.

To remove the Hind III cohesive termini, the DNA was treated with 1.5 microliters of S1 Nuclease (Miles Laboratories) in a final volume of 300 microliters of a buffer containing 30 mM Na-acetate (pH 4.25), 0.3 M NaCl and 4 mM ZnSO$_4$ (hereinafter referred to as an "S1 buffer") at 20° C. for one hour. The reaction was terminated by adding 30 microliters 500 mM Tris:HCl (pH 8.0) and 30 microliters 250 mM EDTA, following which phenol extraction was performed. To remove phenol, the mixture was extracted with ether and dialyzed against 0.01×SSC (SSC =0.15 M NaCl+0.015 M Na-citrate) at 4° C. overnight, and the DNAs were recovered by ethanol precipitation.

Phosphorylated Eco RI linker (200 pmoles) was then added and the mixture was treated with 4 units of T4 DNA ligase in 12.5 microliters of ligase buffer containing 0.6 mM ATP at 12.5° C. for 16 hours. Eco RI cohesive termini were created by addition of 30 units of Eco RI restriction enzyme in 75 microliters of Eco RI buffer at 37° C. for 2 hours. The reaction was terminated by phenol extraction and the DNAs were recovered by ethanol precipitation.

Eco RI cohesive termini were ligated and the plasmid was thereby re-circularized by treatment with 0.3 units of T4 DNA ligase in 20 microliters of ligase buffer containing 0.4 mM ATP at 12.5° C. for 7 hours. A 0.5 microgram aliquot of the ligated DNA was used to transform *E. coli* strain JE5519, NRRL B-15013 (F-, aroD, man, argE, lac, gal, rpsL, gyrA, recAl; obtained from Dr. Y. Hirota, National Institute of Genetics, Mishima, Japan). This strain is available to the public from the permanent collection of the Northern Regional Research Laboratory, U.S. Department of Agriculture, Peoria, Ill., U.S.A. Ten of the ampicillin-resistant, tetracycline-sensitive transformants were grown overnight in one ml of L broth containing 50 micrograms/ml of ampicillin. Plasmid DNAs were isolated from 0.5 ml of the cultures by the rapid alkaline-denaturation method described by Birnboim, H. C. and Doly, *J. Nucleic Acids Res.* 7: 1513 (1979), and analyzed by restriction enzyme map. One of the plasmids had the structure shown at 107 in FIG. 7, and was designated pKEN005.

As shown schematically at 108 in FIG. 7, the 462 bp Alu I fragment containing the lpp promoter was derived as follows: 100 micrograms of pKEN111 plasmid DNA were digested with Msp I restriction enzyme in 600 microliters of a buffer containing 10 mM Tris:HCl (pH 7.5), 10 mM MgCl$_2$, 6 mM KCl, 1 mM dithiothreitol, and 100 micrograms/ml BSA (this mixture will hereinafter be referred to as an "Hpa I buffer") at 37° C. for 3 hours. (Although pKEN111 contains numerous Msp I cleavage sites, only the two of interest are illustrated at 109 in FIG. 7.) Following extraction with phenol, the DNA fragments were precipitated with 2.5 volumes of ethanol, dried under vacuum, dissolved in 100 microliters of gel buffer, and fractionated on a 5% polyacrylamide gel. Approximately 6 micrograms of a purified 0.95 Kb Msp I fragment were recovered after elution of the separated DNA fragments from the gel. The purified 0.95 Kb Msp I fragment was subsequently digested with Alu I restriction endonuclease in 400 microliters of Hind III buffer at 37° C. for 2 hours, yielding a 462 bp Alu I fragment which was purified by gel electrophoresis.

One microgram of the 462 bp Alu I fragment was then mixed with 150 pmoles of phosphorylated Eco RI linker and treated with 4 units of T4 DNA ligase in 10 microliters of ligase buffer containing 0.6 mM ATP at 12.5° C. for 16 hours. The ligated DNA was digested with 40 units of Eco RI restriction enzyme in 100 microliters of Eco RI buffer at 37° C. for one hour to create Eco RI cohesive termini. The digestion was terminated by heating the mixture at 60° C. for 10 minutes, and 0.6 micrograms of Eco RI-digested pKEN005 plasmid DNA were added to the mixture and phenol extraction was performed. The DNAs were recovered by ethanol precipitation, and the Eco RI cohesive termini were joined by treating with 0.4 units of T4 DNA ligase in 20 microliters of ligase buffer containing 0.4 mM ATP at 12.5° C. for 7 hours. Ligated DNAs were used to transform *E. Coli* strain JE5519, NRRL B-15013, and transformants were selected for tetracycline resistance on an L broth plate containing 12.5 micrograms/ml of tetracycline. Analysis of the plasmid DNAs isolated from the tetracycline-resistant transformants by the rapid alkalinedenaturation method showed insertion of the 462 bp Alu I fragment at the Eco RI site of pKEN005 as depicted at 110 in FIG. 7, and one of the plasmids thus obtained was designated pKEN008.

3. Construction Of Plasmid pKEN010

Figure 8:
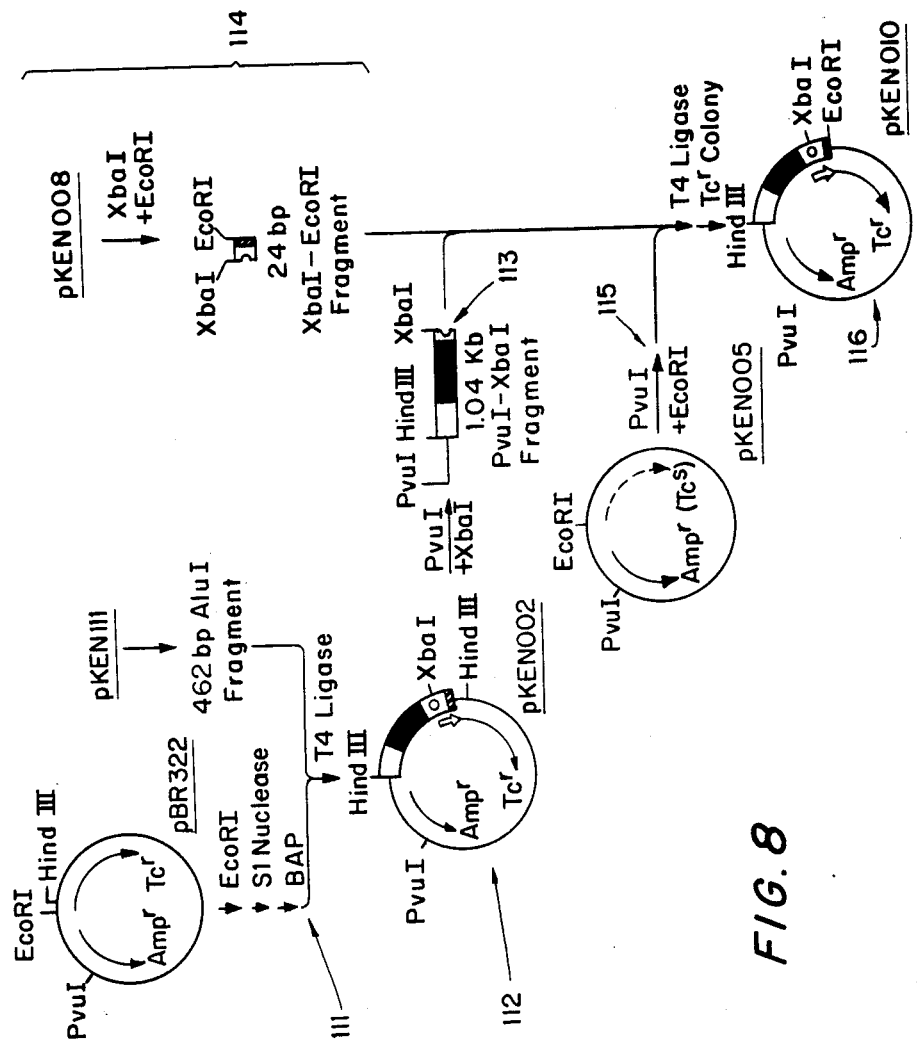

The next step in the construction of the A site lpp gene cloning vehicles was to eliminate one of the two Eco RI cleavage sites of pKEN008. This was necessary in order to insure that the only insertion point available for the exogenous gene chosen for cloning would be immediately downstream of the 462 bp Alu I fragment (now an Eco RI fragment) containing the lpp gene promoter and 5'-untranslated region. FIG. 8 illustrates schematically the strategy for removing the Eco RI site distal to the lpp gene promoter.

In order to accomplish this result, the following procedure was used: 4 micrograms of Eco RI-digested pBR322 plasmid DNA were treated first with S1 Nuclease to remove the Eco RI cohesive termini, and then with BAP to prevent self-ligation. As shown schematically at 111 in FIG. 8, the DNAs were then mixed with 0.76 micrograms of the purified 462 bp Alu I fragment (derived from pKEN111 as described above in connection with FIG. 7), and blunt-end ligated with 2.4 units of T4 DNA ligase in 10 microliters of ligase buffer containing 0.6 mM ATP at 12.5° C. for 16 hours. One-half of the ligated DNA was used to transform *E. coli* strain JE5519, NRRL B-15013, and one of the transformants was shown to contain the plasmid with the structure illustrated at 112 in FIG. 8. This plasmid was designated pKEN002, and after digestion of 25 micrograms of pKEN002 plasmid DNA with Pvu I and Xba I restriction enzymes in 500 microliters of a buffer comprising 6 mM Tris:HCl (pH 7.9), 6 mM MgCl$_2$, 150 mM NaCl, 6 mM β-mercaptoethanol and 100 micrograms/ml BSA (the foregoing mixture will hereinafter be referred to as a "Bam HI buffer") at 37° C. for one hour, a 1.04 Kb Pvu I-Xba I DNA fragment (illustrated at 113 in FIG. 8) was purified by gel electrophoresis.

As shown schematically at 114 in FIG. 8, a 24 bp Xba I-Eco RI DNA fragment was derived from pKEN008 as follows: 25 micrograms of pKEN008 plasmid DNA was digested with Eco RI restriction enzyme, and a 470 bp Eco RI fragment was purified by gel electrophoresis. One microgram of the 470 bp Eco RI fragment was then digested with Xba I restriction enzyme, and was mixed with one microgram of the 1.04 Kb Pvu I-Xba I DNA fragment obtained previously, as well as with 0.75 micrograms of pKEN005 plasmid DNA previously digested with Pvu I and Eco RI restriction enzymes (as shown at 115 in FIG. 8). The DNA mixture was treated with 0.8 units of T4 DNA ligase in 50 microliters of ligase buffer containing 0.4 mM ATP at 12.5° C. for 7 hours. One-half of the ligated DNA was used to transform *E. coli* strain JE5519, NRRL B-15013, and transformants were selected for tetracycline resistance. Analysis of the plasmid DNAs obtained from 0.5 ml cultures of tetracycline-resistant transformants by the rapid alkaline-denaturation method, indicated that one of the plasmids had the structure shown at 116 in FIG. 8. This plasmid was designated pKEN010.

4. Construction Of Plasmid pKEN018

Figure 9:
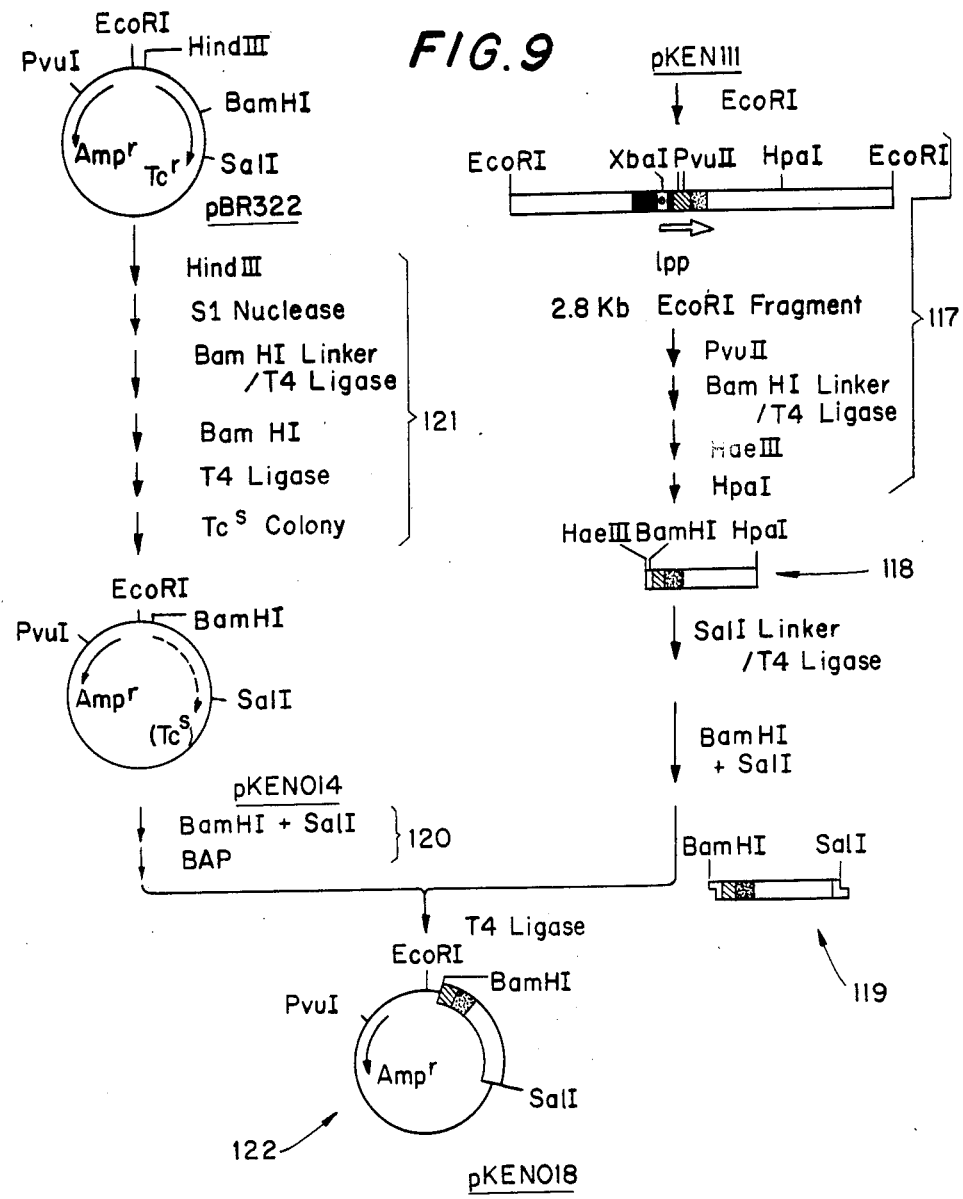

FIG. 9 illustrates the strategy used for cloning a DNA fragment carrying the 3'-untranslated region and the transcription termination site of the lpp gene. The fragment chosen for this purpose was a 0.95 Kb Pvu II-Hpa I fragment of pKEN111, shown schematically at 105D in FIG. 5. Since the Pvu II restriction enzyme cleaves the lpp gene sequence between positions +167 and +168, this fragment contains approximately the latter half of the lpp gene (see FIGS. 1 and 5). In order to insert this fragment into the cloning vehicle in the same orientation as the promoter fragment, Bam HI linker and Sal I linker were attached to the Pvu II and Hpa I cleavage sites, respectively.

As shown schematically at 117 in FIG. 9, a 2.8 Kb Eco RI fragment was obtained from pKEN111 plasmid DNA by digestion with Eco RI restriction enzyme and fractionation on a polyacrylamide gel, and 10 micrograms of this purified fragment were digested completely with Pvu II restriction endonuclease in 500 microliters of Hae III buffer at 37° C. for one hour. The reaction was terminated by phenol extraction, and the mixture was extracted with ether. The DNA fragments were precipitated with 2.5 volumes of ethanol, centrifuged, re-dissolved in 200 microliters of 0.3 M Na-acetate and re-precipitated with 0.5 ml of ethanol. Five micrograms of the Pvu II-digested 2.8 Kb Eco RI fragment were mixed with 390 pmoles of phosphorylated Bam HI linker and blunt-end ligated with 6 units of T4 DNA ligase in 25 microliters of ligase buffer containing 0.6 mM ATP at 12.5° C. for 16 hours. The reaction mixture was diluted to 150 microliters with Hae III buffer and heated at 60° C. for 10 minutes to inactivate the T4 DNA ligase. After the addition of 60 units of Hae III restriction enzyme, the mixture was incubated at 37° C. for one hour.

Since the Bam HI linker used here (obtained from Collaborative Research and phosphorylated in the same manner as described previously in connection with the Eco RI linker) has the base sequence 5'CCGGATCCGG3', the recognition sequence for the restriction enzyme Hae III

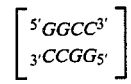

was created at the junction of any two linker fragments. Thus, the use of Hae III restriction enzyme as set forth above to digest the Bam HI linker-ligated Pvu II fragments (which fragments do not contain any internal Hae III cleavage sites) effected the removal of superfluous multiple Bam HI linker fragments joined to the Pvu II terminus, leaving only one such linker fragment directly joined to that terminus. This procedure greatly simplified the purification of the DNA fragment containing the 3' end of the lpp gene, as described below.

After inactivation of the Hae III enzyme by heating the reaction mixture at 60° C. for 10 minutes, the DNA fragments were digested completely with Hpa I restriction enzyme in 400 microliters of Hpa I buffer at 37° C. for 2 hours. The reaction mixture was extracted with phenol and the DNA fragments were precipitated with ethanol, dried under vacuum, dissolved in 100 microliters of gel buffer and fractionated on a 5% polyacrylamide gel. The DNA band which had migrated to a 0.95 Kb position was excised from the gel, and the DNA fragments were eluted from the gel by electrophoresis. After removal of ethidium bromide dye by phenol extraction, the DNA fragments were precipitated with 2.5 volumes of ethanol, centrifuged, dissolved in 200 microliters of 0.3M Na-acetate, re-precipitated with 0.5 ml of ethanol and again dried under vacuum. Approximately one microgram of a purified 0.95 Kb Hae III-Hpa I fragment (illustrated at 118 in FIG. 9) was recovered.

One hundred and twenty pmoles of phosphorylated Sal I linker (5'GGTCGACC3'; obtained from Collaborative Research and phosphorylated according to the same procedure as described hereinabove) were mixed with 0.75 micrograms of the purified 0.95 Kb Hae III-Hpa I fragment, and blunt-end ligated with 3.5 units of T4 DNA ligase in 25 microliters of ligase buffer containing 0.6 mM ATP at 12.5° C. for 16 hours. The reaction mixture was diluted with sufficient Bam HI buffer to make a final volume of 300 microliters and was then heated at 60° C. for 10 minutes. Sufficient amounts of Bam HI and Sal I restriction enzymes were added and the mixture was incubated at 37° C. for 2 hours to create cohesive termini by cleaving the Bam HI and Sal I linkers attached to the Pvu II and Hpa I termini, respectively, resulting in a 0.95 Kb Bam HI-Sal I fragment (illustrated at 119 in FIG. 9). The restriction endonuclease digestion was terminated by heating at 60° C. for 10 minutes.

At this stage, half the volume of the mixture (150 microliters), containing approximately 0.38 micrograms of the 0.95 Kb Bam HI-Sal I fragment, was mixed with one microgram of pKEN014 plasmid DNA, which had previously been digested with Bam HI and Sal I restriction enzymes and treated with BAP (as shown schematically at 120 in FIG. 9). Plasmid pKEN014 had been previously derived from pBR322 by deleting a 346 bp Hind III-Bam HI fragment (containing most of the tetracycline resistance gene) from pBR322. This fragment was removed in order to keep the size of the expression plasmids to a minimum (approximately 5 Kb). The deletion of this fragment was accomplished, as shown schematically at 121 in FIG. 9, by Hind III digestion, followed by S1 Nuclease treatment for one hour at 20° C., Bam HI linker attachment, Bam HI complete digestion, re-circularization by T4 DNA ligase, and selection of tetracycline-sensitive transformants.

The mixture of linearized pKEN014 plasmid DNA and 0.95 Kb Bam HI-Sal I fragments was extracted with phenol, and the DNAs were precipitated with 2.5 volumes of ethanol, centrifuged and dissolved in 200 microliters of 0.3M Na-acetate. The DNAs were re-precipitated with 0.5 ml of ethanol, centrifuged and dried under vacuum. Cohesive termini of the DNA fragments were annealed with 0.4 units of T4 DNA ligase in 60 microliters of ligase buffer containing 0.4 mM ATP at 12.5° C. for 7 hours. Twelve microliters of the ligated mixture were then used to transform E. coli strain JE5519, NRRL B-15013, and twelve of the ampicillin-resistant transformants were grown overnight in one ml of L broth containing 50 micrograms/ml of ampicillin. Plasmid DNAs were isolated from 0.5 ml of the cultures by the rapid alkaline-denaturation method and analyzed by agarose gel electrophoresis. Five of the plasmid DNAs were found to carry the 0.95 Kb Bam HI-Sal I fragment, and one of these plasmids was designated pKEN018. DNA sequencing of the plasmid DNA indicated the structure shown at 122 in FIG. 9, and specifically showed that the Bam HI linker was attached at the Pvu II site within the lpp gene at the correct position.

5. Construction Of Plasmid pKEN021

The next step in the construction of the A site lpp gene cloning vehicles was to combine the lpp promoter fragment with the transcription terminator fragment in the same orientation. This step was carried out by replacing a 630 bp Pvu I-Eco RI fragment of pKEN018 with a 1.1 Kb Pvu I-Eco RI fragment of pKEN010, as illustrated schematically in FIG. 10.

In order to accomplish this result, 20 micrograms of pKEN010 plasmid DNA were digested to completion (as shown at 123 in FIG. 10) with Pvu I restriction endonuclease in 100 microliters of Bam HI buffer at 37° C. for 1.5 hours. After inactivating the Pvu I enzyme by heating the reaction mixture at 60° C. for 10 minutes, 52 microliters of water, 40 microliters of 0.5M Tris:HCl (pH 7.5), 4 microliters of 0.1M MgCl$_2$ and 40 units of Eco RI restriction enzyme were added. The reaction mixture was incubated at 37° C. for one hour and the digestion was terminated by phenol extraction. The DNA fragments were precipitated with 2.5 volumes of ethanol, dried under vacuum, dissolved in 100 microliters of gel buffer, and fractionated on a 5% polyacrylamide gel. Four micrograms of a purified 1.1 Kb Pvu I-Eco RI fragment were obtained after elution of the separated DNA fragments from the gel.

Figure 10:
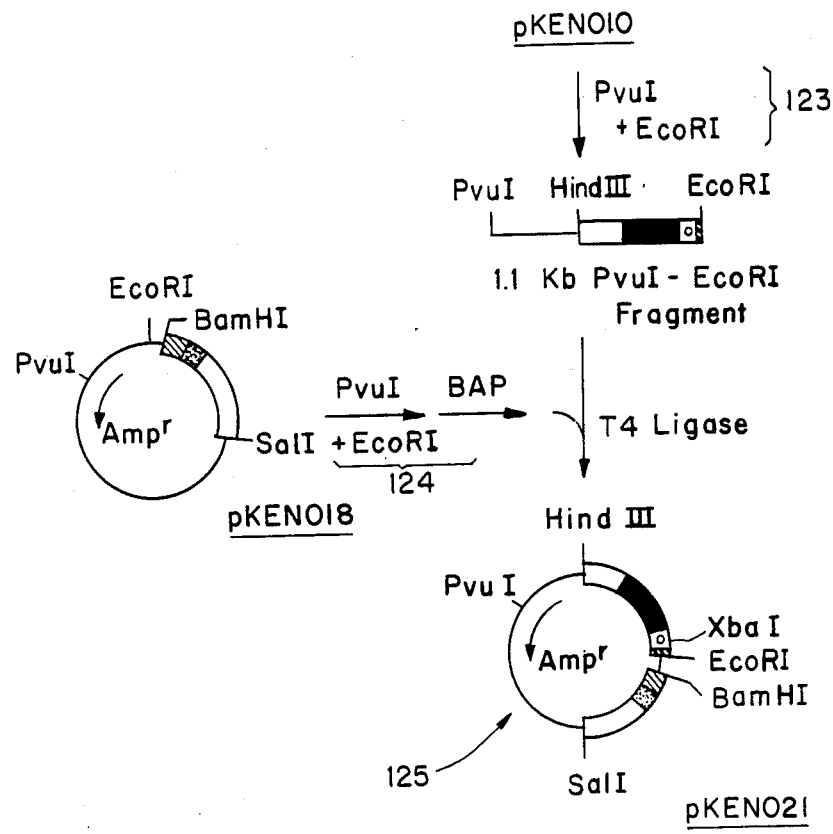

The purified fragment (0.75 micrograms) was then mixed with 0.6 micrograms of pKEN018 plasmid DNA which had previously been double-digested with Pvu I and Eco RI restriction enzymes and then treated with BAP (as shown at 124 in FIG. 10). The Pvu I and the Eco RI cohesive termini were ligated by treating with 0.4 units of T4 DNA ligase in 50 microliters of ligase buffer containing 0.4 mM ATP at 12.5° C. for 7 hours. Twenty-five microliters of the ligated mixture were used to transform E. coli strain JE5519, NRRL B-15013, and transformants were selected for ampicillin resistance. Plasmid DNAs were isolated from ampicillin-resistant transformants and analyzed by agarose gel electrophoresis. Restriction enzyme mapping indicated that one of the plasmids had the structure shown at 125 in FIG. 10, and this plasmid was designated pKEN021.

6. Construction Of Plasmid pKEN037

Figure 11:
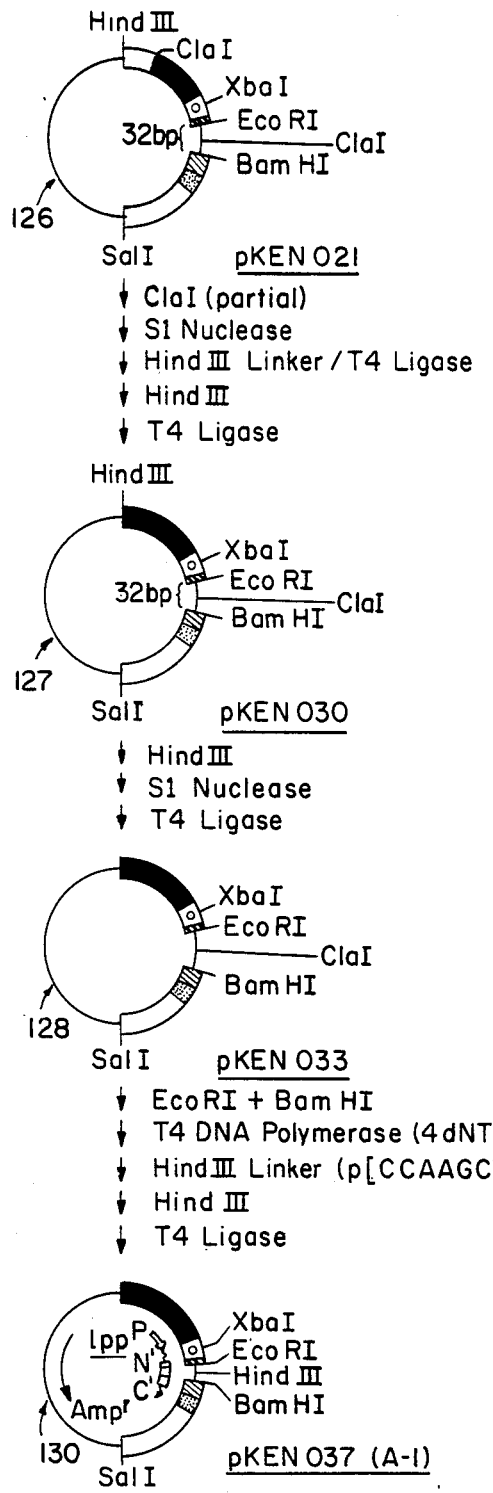

FIG. 11 illustrates the final step in the construction of the first A site lpp gene expression plasmid. As shown at 126 in FIG. 11, pKEN021 carries both the lpp promoter fragment and the lpp transcription terminator fragment, separated by a 32 bp fragment derived from pBR322. By deleting the latter fragment and inserting a DNA sequence coding for a desired polypeptide, a functional moiety for expression of the desired polypeptide is provided. However, since there are Eco RI and Bam HI cleavage sites at the ends of the 32 bp fragment, the structure of plasmid pKEN021 allows only for the insertion of exogenous DNA insert fragments having Eco RI-Eco RI, Bam HI-Bam HI, or Eco RI-Bam HI cohesive termini. Therefore, in order to expand the class of exogenous genes which can be inserted to include those tailored with other combinations of cohesive termini, the DNA sequence in this region was modified to add a Hind III cleavage site between the existing Eco RI and Bam HI sites.

To accomplish this result, it was first desirable to reduce the size of the plasmid by eliminating the 200 bp Hind III-Cla I fragment in pKEN021, using the following procedure: five micrograms of pKEN021 plasmid DNA were partially digested with one unit of Cla I restriction enzyme in 100 microliters of a reaction mixture comprising 10 mM Tris:HCl (pH 8.0), 10 mM MgCl$_2$ and 100 micrograms/ml BSA at 37° C. for one hour. After phenol extraction and ethanol precipitation, Cla I cohesive termini were removed by treating with 600 units of S1 Nuclease in 200 microliters of S1 buffer at 20° C. for one hour. The reaction was terminated by adding 20 microliters of 0.5M Tris:HCl (pH 8.0) and 20 microliters of 0.25M EDTA. The mixture was extracted with phenol and dialyzed for four hours against 0.01 X SSC. The DNAs were precipitated with 2.5 volumes of ethanol, centrifuged and resuspended in 100 microliters of 0.3M Na-acetate. The DNAs were re-precipitated with 250 microliters of ethanol, centrifuged, and dried under vacuum.

One microgram of the S1-treated DNA was then mixed with 70 pmoles of phosphorylated Hind III linker (5'CCAAGCTTGG3'; obtained from Collaborative Research and phosphorylated according to the same procedure as described hereinabove) and blunt-end ligated with 4 units of T4 DNA ligase in 20 microliters of ligase buffer containing 0.6 mM ATP at 12.5° C. for 16 hours. The mixture was then diluted to 100 microliters with Hind III buffer and heated at 60° C. for 10 minutes. Twenty units of Hind III restriction endonuclease were added, and the mixture was incubated at 37° C. for one hour to remove superfluous linker molecules and to create Hind III cohesive termini. The reaction mixture was then extracted with phenol, and the DNAs were precipitated with ethanol. Plasmid DNAs (0.5 micrograms) were re-circularized by treating with 0.8 units of T4 DNA ligase in 15 microliters of ligase buffer containing 0.4 mM ATP at 12.5° C. for 7 hours. Eight microliters of the ligated mixture were used to transform E. coli strain JA221, NRRL B-15014 (recA$^-$hr$^-$, hm+, αtrpE5, thr, leu, thi, lacY$^-$; obtained from Dr. J. Carbon, Dept. of Biological Sciences, University of California, Santa Barbara). This strain is available to the public from the permanent collection of the Northern Regional Research Laboratory, U.S. Department of Agriculture, Peoria, Ill., U.S.A. Among the plasmid DNAs which were purified from the ampicillin-resistant transformants was one that had the structure shown at 127 in FIG. 11, and this plasmid was designated pKEN030.

In order to eliminate the Hind III cleavage site of pKEN030, 2.5 micrograms of pKEN030 plasmid DNA were digested with 5 units of Hind III restriction enzyme in 50 microliters of Hind III buffer at 37° C. for one hour. After phenol extraction and ethanol precipitation, the Hind III cohesive termini were removed by treating with 400 units of S1 nuclease in 200 microliters of S1 buffer at 20° C. for one hour. Following recovery of the DNA, 0.75 micrograms of the S1-treated plasmid DNAs were re-circularized by treating with 2 units of T4 DNA ligase in 10 microliters of ligase buffer containing 0.6 mM ATP at 12.5° C. for 16 hours. Three microliters of the ligated mixture were then used to transform E. coli strain JA221, NRRL B-15014, and one of the plasmids isolated from the ampicillin-resistant transformants was found to have the structure shown at 128 in FIG. 11. This plasmid, designated pKEN033, contained no Hind III cleavage sites.

Figure 12:
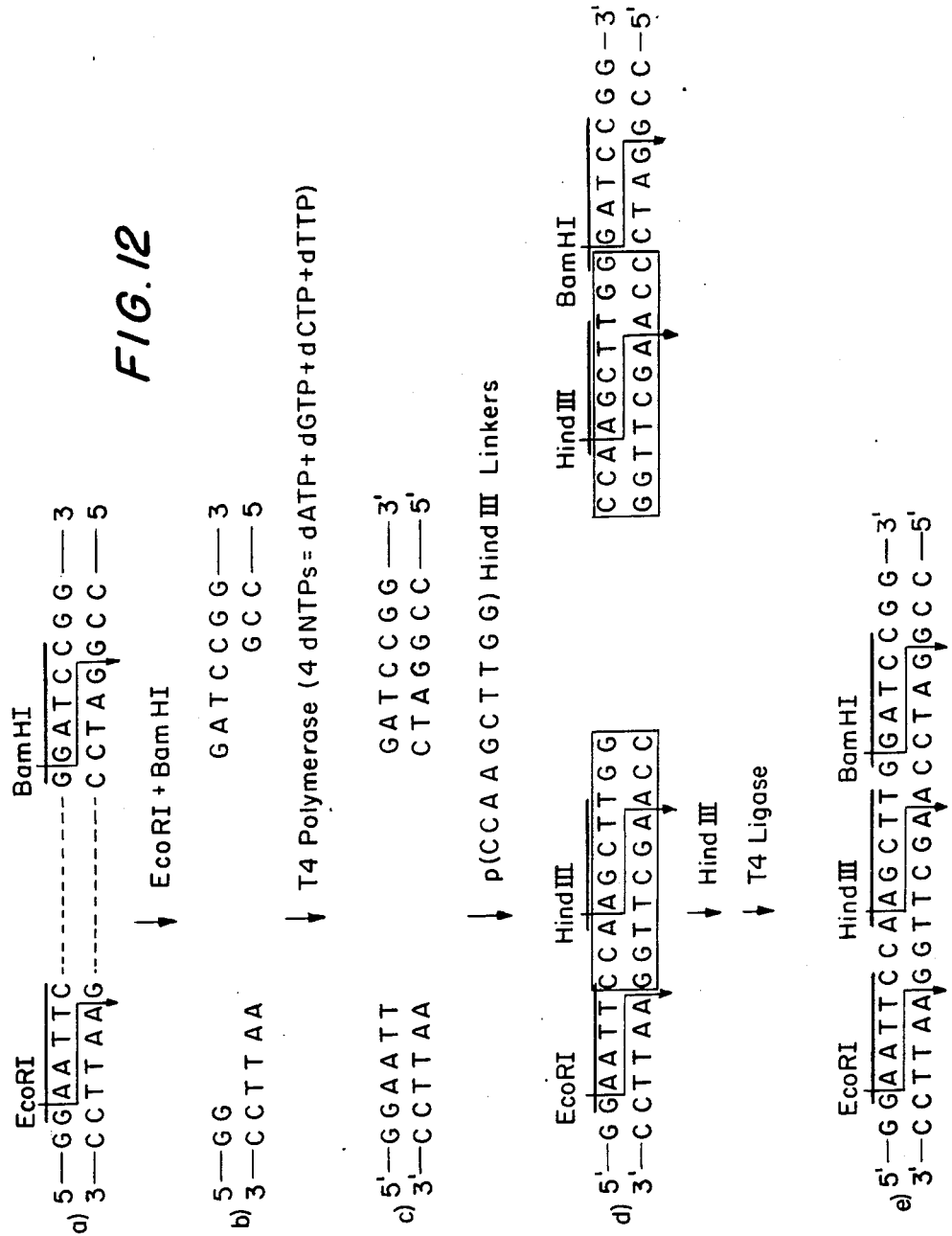

As shown schematically at 129 in FIG. 11, and in more detail in FIG. 12, the DNA sequence of plasmid pKEN033 was modified to create a Hind III cleavage site between the Eco RI and Bam HI sites, as follows: 5 micrograms of pKEN033 plasmid DNA (having the DNA sequence of interest shown in FIG. 12, line a) were digested with 10 units of Bam HI restriction endonuclease in 50 microliters of Bam HI buffer at 37° C. for one hour. After inactivation of the Bam HI enzyme by heating the reaction mixture at 60° C. for 10 minutes, the linearized DNA fragments were further digested with 10 units of Eco RI enzyme in 100 microliters of Eco RI buffer at 37° C. for one hour (see FIG. 12, line b). After phenol extraction and ethanol precipitation, the DNAs (3.6 micrograms) were treated with three units of T4 DNA polymerase (obtained from Bethesda Research Laboratories) in 20 microliters of a reaction mixture containing 50 mM Tris:HCl (pH 8.0), 100 mM KCl, 6 mM MgCl$_2$, and 6 mM dithiothreitol (this reaction mixture will hereinafter be referred to as a "polymerase buffer") in the presence of 0.1 mM each of dATP, dGTP, dCTP and dTTP at 12.5° C. for 45 minutes. By this procedure, the Bam HI and the Eco RI "sticky ends" were filled in completely, as shown in FIG. 12, line c.

After recovery of the DNAs, 300 pmoles of phosphorylated Hind III linker were added, followed by bluntend ligation with 4 units of T4 DNA ligase in 15 microliters of ligase buffer containing 0.6 mM ATP at 12.5° C. for 16 hours. The mixture was then diluted to 100 microliters with Hind III buffer, and digested with 100 units of Hind III restriction enzyme. The mixture was incubated at 37° C. for one hour to remove superfluous linker molecules and to create Hind III cohesive termini (see FIG. 12, line d), which were later joined (thereby re-circularizing the plasmid DNAs) by treating 0.8 micrograms of the DNA with 0.4 units of T4 DNA ligase in 20 microliters of ligase buffer containing 0.4 mM ATP at 12.5° C. for 7 hours. Following transformation of E. coli strain JA221, NRRL B-15014, with a portion of the ligated mixture, plasmid DNAs were isolated from the ampicillin-resistant colonies, and one of them had the structure indicated at 130 in FIG. 11 and was designated pKEN037. Analysis of the DNA nucleotide sequence of pKEN037 revealed the DNA sequence depicted in FIG. 12, line e, in which one G-C pair was deleted between the Hind III and Bam HI cleavage sites (for reasons which are presently unknown), and confirmed that pKEN037 was the constitutive A-1 cloning vehicle of the present invention.

7. Construction Of Plasmids pKEN039 and pKEN040

Figure 13:
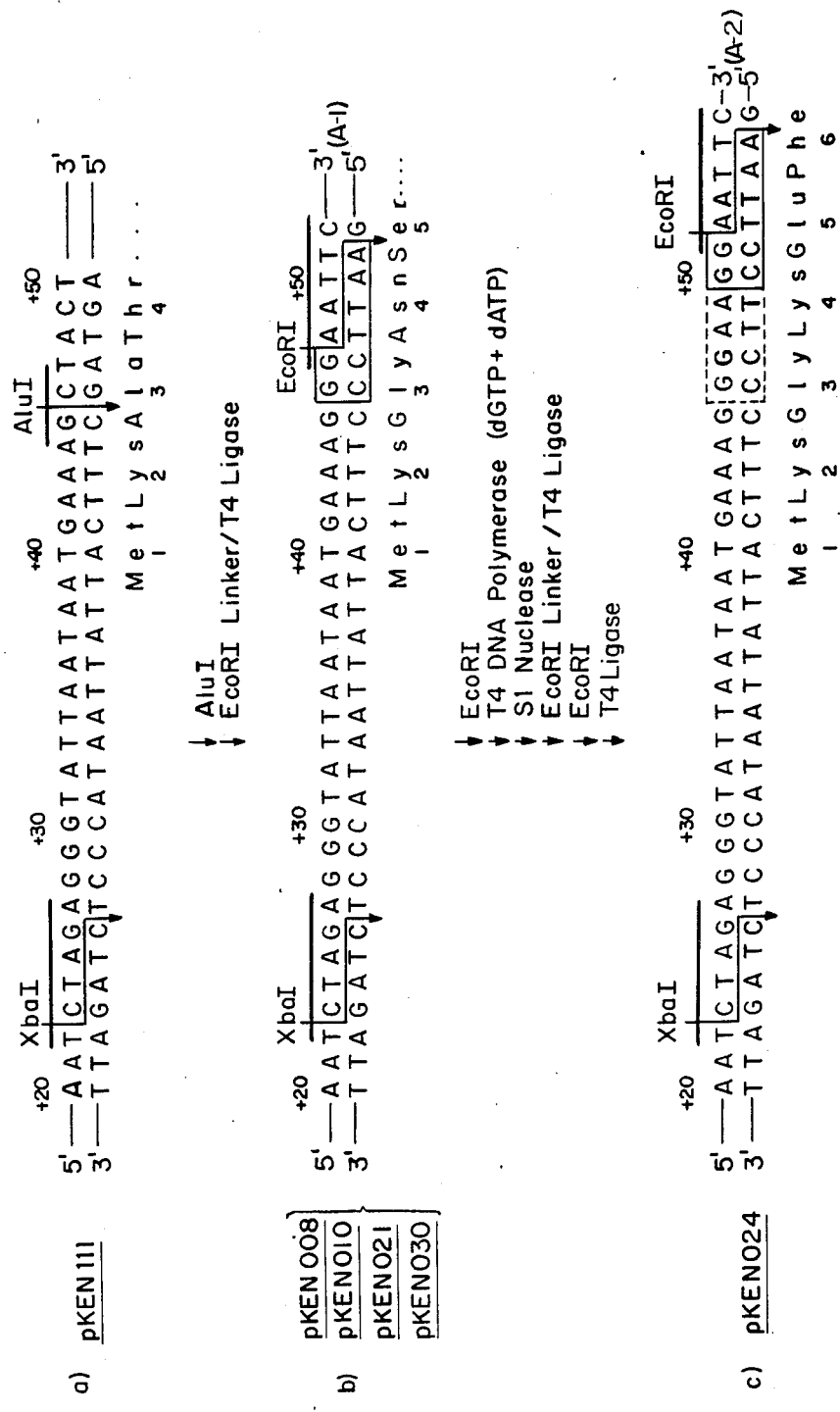
Figure 14:
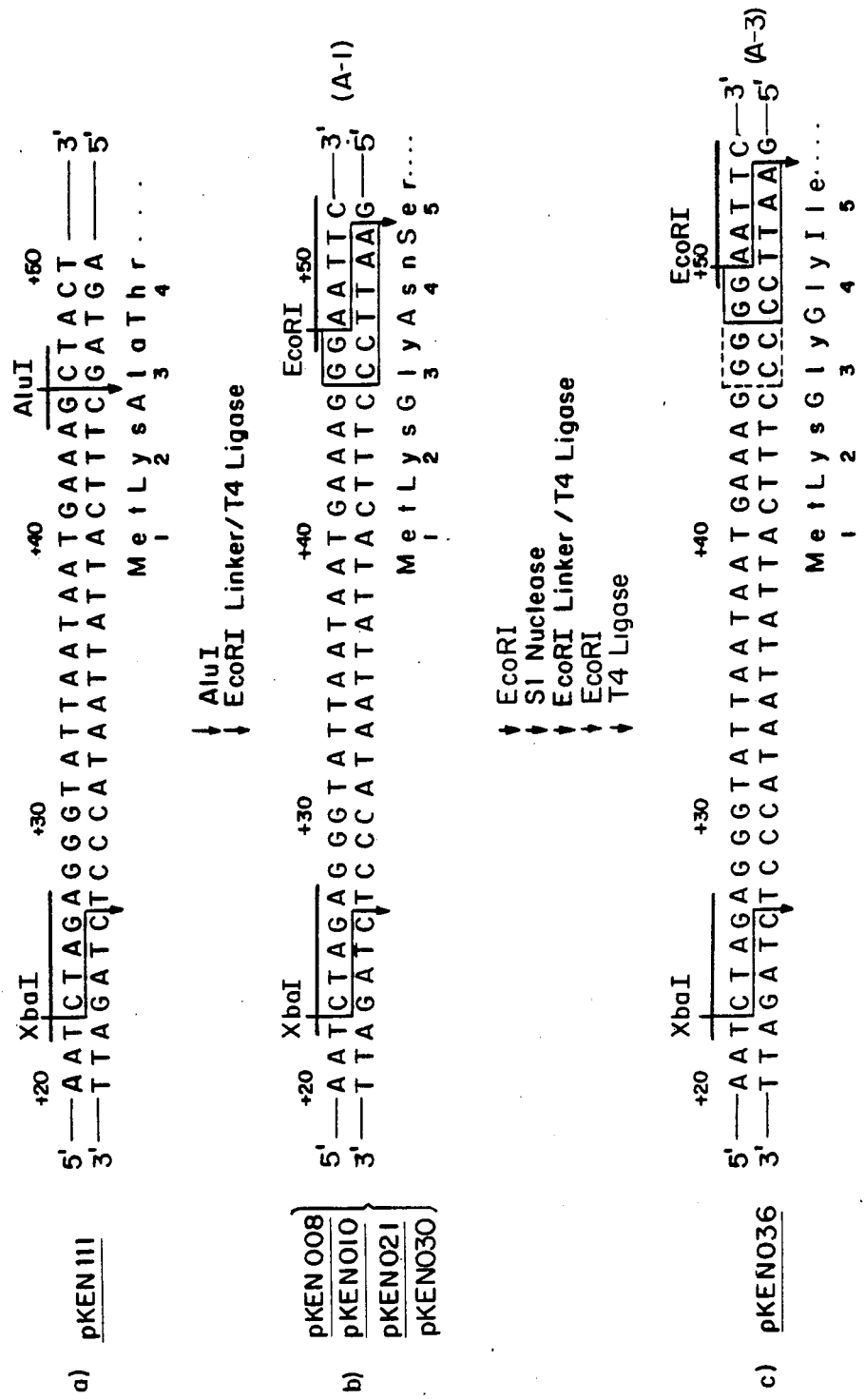

In order to accommodate DNA insert fragments with reading frames differing from that of pKEN037, the A-2 and A-3 lpp gene cloning vehicles were constructed by adjusting the reading frame of pKEN030 at the Eco RI cleavage site. FIG. 13, line a, and FIG. 14, line a, both illustrate the DNA sequence surrounding the translation initiation site of the prolipoprotein in pKEN111. As shown, this sequence includes an Alu I cleavage site between positions +45 and +46. In creating plasmid pKEN008, an Eco RI linker was attached to the Alu I terminus, resulting in the DNA sequence shown in FIG. 13, line b, and in FIG. 14, line b, in plasmids pKEN008, pKEN010, pKEN021 and pKEN030, and creating an Eco RI cleavage site between positions +47 and +48. The DNA sequence of pKEN030 was modified at the Eco RI site, as shown in FIG. 13, line c, and in FIG. 14, line c, to shift its reading frame by one base and by two bases, respectively.

To accomplish this result in the first case to produce a plasmid with the A-2 reading frame, 5 micrograms of pKEN030 plasmid DNA were digested completely with Eco RI restriction enzyme in 100 microliters of Eco RI buffer at 37° C. for 60 minutes. After phenol extraction and ethanol precipitation, the DNAs were treated with 3 units of T4 DNA polymerase in 30 microliters of polymerase buffer in the presence of 0.1 mM dGTP and 0.1 mM dATP at 12.5° C. for 45 minutes. The reaction was terminated by adding EDTA to a final concentration of 25 mM, followed by phenol extraction. By this procedure, half of the 4-base Eco RI "sticky end" was filled in with two A residues. The remaining two single-strand A residues were removed by treating with S1 Nuclease in 200 microliters of S1 buffer at 20° C. for one hour. The reaction was terminated by adding 20 microliters of 0.5M Tris:HCl (pH 8.0) and 20 microliters of 0.25M EDTA. The mixture was extracted with phenol and dialyzed overnight against 0.01 × SSC. The DNAs were precipitated with 2.5 volumes of ethanol, centrifuged and re-suspended in 100 microliters of 0.3M Naacetate. The DNAs were re-precipitated with 250 microliters of ethanol, centrifuged, and dried under vacuum.

In order to restore the Eco RI cleavage site, one microgram of the S1-treated DNA was first mixed with 70 pmoles of phosphorylated Eco RI linker and blunt-end ligated with 3.2 units of T4 DNA ligase in 11 microliters of ligase buffer containing 0.6 mM ATP at 12.5° C. for 16 hours. The mixture was then diluted to 50 microliters with Eco RI buffer and heated at 60° C. for 10 minutes. Twenty units of Eco RI restriction endonuclease were added, and the mixture was incubated at 37° C. for one hour to remove superfluous linker molecules and to create Eco RI cohesive termini. The reaction mixture was then extracted with phenol, and the DNAs were precipitated with ethanol. Plasmid DNAs (0.5 micrograms) were re-circularized by treating with 0.8 units of T4 DNA ligase in 15 microliters of ligase buffer containing 0.4 mM ATP at 12.5° C. for 7 hours. Eight microliters of the ligated mixture were used to transform E. coli strain JA221, NRRL B-15014. Plasmid DNAs were purified from 3 ampicillin-resistant transformants, which had been grown overnight in one hundred ml of L broth containing 50 micrograms/ml of ampicillin, and the DNA sequences at their Eco RI cleavage sites were determined. One of them was found to have the sequence shown in FIG. 13, line c, and was designated pKEN024 (A-2).

To construct a plasmid with the A-3 reading frame, 5 micrograms of pKEN030 plasmid DNA were digested completely with Eco RI restriction enzyme in 100 microliters of Eco RI buffer at 37° C. for 60 minutes. After phenol extraction and ethanol precipitation, the Eco RI "sticky ends" were removed by treating the DNA (4.4 micrograms) with 500 units of S1 Nuclease in 150 microliters of S1 buffer at 20° C. for one hour. The reaction was terminated by adding 15 microliters of 0.5M Tris:HCl (pH 8.0) and 15 microliters of 0.25M EDTA. The mixture was extracted with phenol and dialyzed for four hours against 0.01 × SSC. The DNAs were precipitated with 2.5 volumes of ethanol, centrifuged and re-suspended in 100 microliters in 0.3 Na-acetate. The DNAs were re-precipitated with 250 microliters of ethanol, centrifuged, and dried under vacuum.

In order to restore the Eco RI cleavage site, one microgram of the S1-treated DNA was first mixed with 240 pmoles of phosphorylated Eco RI linker and blunt-end ligated with 4 units of T4 DNA ligase in 15 microliters of ligase buffer containing 0.6 mM ATP at 12.5° C. for 16 hours. The mixture was then diluted to 250 with Eco RI buffer and heated at 60° C. for 10 minutes. One hundred units of Eco RI restric were added, and the mixture was incubated at 37° C. for one hour to remove superfluous linker molecules. an to create Eco RI cohesive termini. The reaction mixture was then extracted with phenol, and the DNAs were precipitated with ethanol. Plasmid DNAs (0.3 micrograms) were re-circularized by treating with 0.8 units of T4 DNA ligase in 15 microliters of ligase buffer containing 0.4 mM ATP at 12.5 ° C. for 7 hours. Eight microliters of the ligated mixture were used to transform E. coli strain JA221, NRRL B-15014. Plasmid DNAs were purified from 3 ampicillin-resistant transformants, which had been grown overnight in one hundred ml of L broth containing 50 micrograms/ml of ampicillin, and the DNA sequences at their Eco RI cleavage sites were determined. One of them was found to have the sequence shown in FIG. 14, line c, and was designed pKEN036 (A-3).

Figure 15:
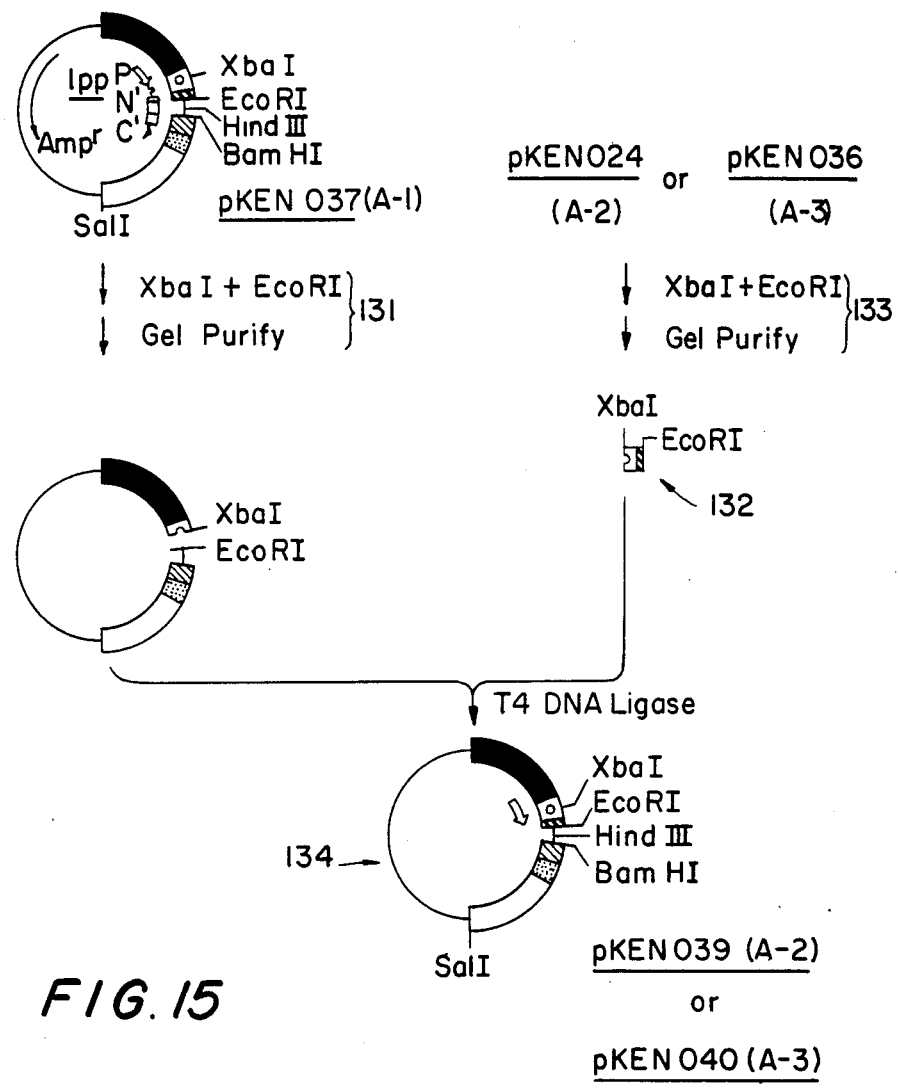

To change the translational reading frame of pKEN037 (A-1) into the two other reading frames (A-2 and A-3), the smaller Xba I-Eco RI fragment of pKEN037 was replaced with the smaller Xba I-Eco RI fragments from pKEN024 (A-2) or pKEN036 (A-3), as shown schematically in FIG. 15, using the following procedure: 3 micrograms of pKEN037 were first digested (as shown at 131 in FIG. 15) with 6 units of Xba I restriction enzyme in 50 microliters of Bam HI buffer at 37° C. for one hour, and after inactivation of the Xba I enzyme, the linearized DNA fragments were further digested with 6 units of Eco RI restriction enzyme in 100 microliters of Eco RI buffer at 37° C. for one hour. The larger Xba I-Eco RI fragment was separated from the smaller fragment by agarose gel electrophoresis: the DNA fragments in the agarose gel were stained with ethidium bromide (one microgram/ml), and the band corresponding to the larger fragment was cut out. The DNA fragments in this band were eluted from the gel after freezing. Ethidium bromide was removed from the DNA fragments by phenol extraction, and the DNAs were recovered by ethanol precipitation.

The dried DNA fragments were dissolved in 20 microliters of water, and one microliter aliquots of this pKEN037 DNA fragment mixture were combined with 0.1 micrograms of each of the smaller Xba I-Eco RI restriction fragments (illustrated at 132 in FIG. 15) previously obtained from pKEN024 or pKEN036 by double-digestion of each plasmid with Xba I and Eco RI restriction enzymes followed by gel purification (as shown at 133 in FIG. 15). The "sticky ends" of the Xba I-Eco RI fragments were joined by treatment with 0.2 units of T4 DNA ligase in 20 microliters of ligase buffer containing 0.4 mM ATP at 12.5° C. for 7 hours, following which a portion of the ligated mixture was used to transform E. coli strain JA221, NRRL B-15014. Among the ampicillin-resistant transformants, plasmid DNAs having the A-2 and A-3 reading frames were obtained, and these were designated pKEN039 and pKEN040, respectively, each having the structure shown at 134 in FIG. 15.

It will be appreciated that the foregoing was the experimental procedure used to construct plasmids pKEN039 (A-2) and pKEN040 (A-3) in the first instance. However, it will be understood by those skilled in the art that an alternative method exists with which to construct those plasmids. Specifically, the DNA sequence in the vicinity of the Eco RI cleavage site of plasmid pKEN037 (A-1) can itself be modified according to the scheme illustrated in FIG. 13, lines b and c, or the scheme shown in FIG. 14, lines b and c, to yield directly the structure of plasmids pKEN039 (A-2) or pKEN040 (A-3), respectively.

B. Construction Of B Site Plasmids (pIN-I)

FIGS. 16–21 schematically illustrate the manner in which recombinant plasmids incorporating the B insertion site were constructed, and may be referred to in connection with the following more particularized discussion.

1. Construction Of Plasmid pKEN221

The first step in the construction of the B site expression plasmids was to construct a plasmid to serve as a source of lpp gene fragments having a restriction enzyme cleavage site at or near the signal peptide cleavage site. The gene chosen codes for the lipoprotein of *S. marcescens*, and has a Fnu4H-I restriction endonuclease recognition sequence at the 3' end of the signal peptide. The plasmid chosen to receive the *S. marcescens* lpp gene was pBR322.

Figure 16:
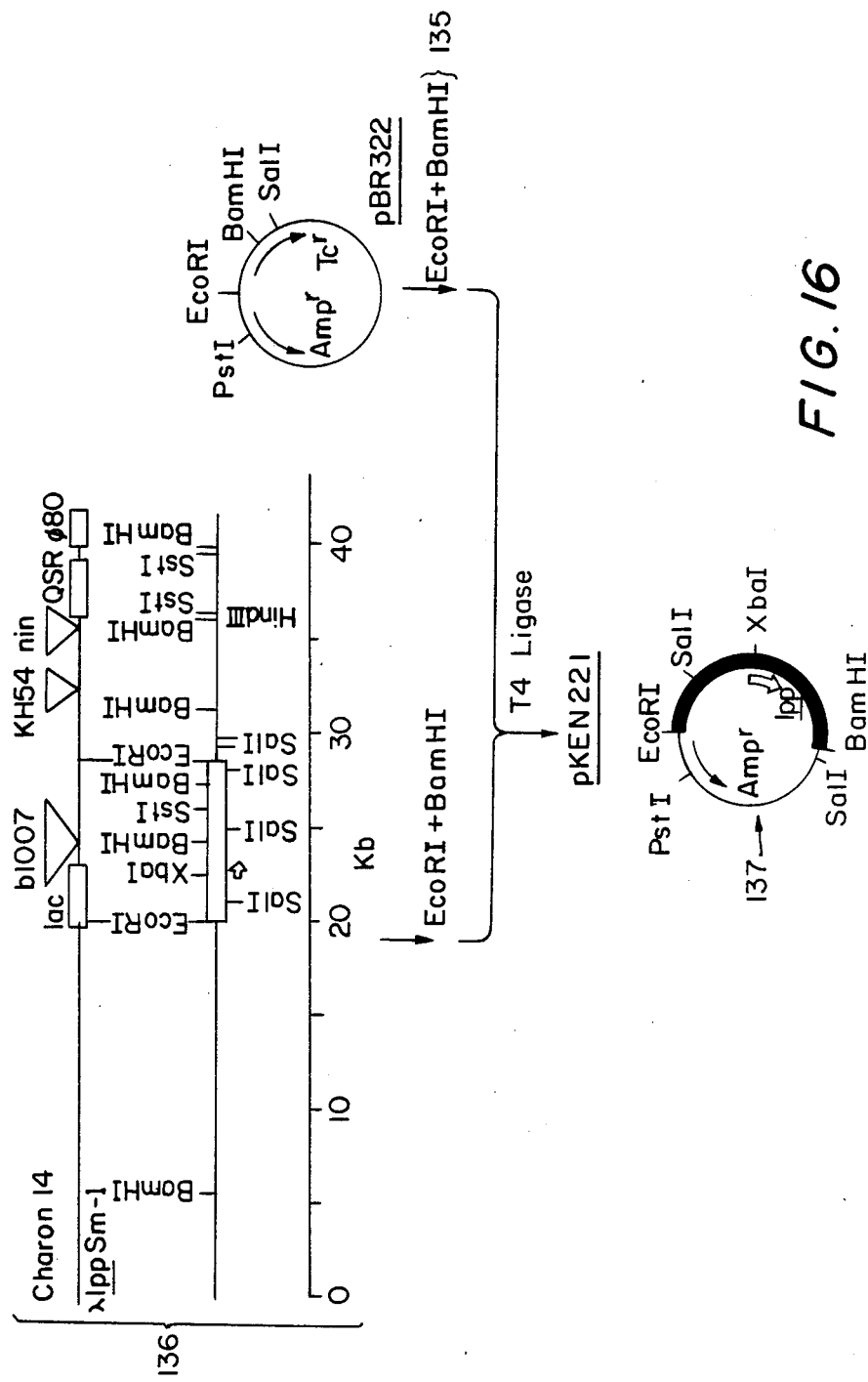

As shown schematically at 135 in FIG. 16, 2 micrograms of plasmid pBR322 DNA were digested to completion with two units of the restriction endonuclease Bam HI in 50 microliters of Bam HI buffer at 37° C. for 60 minutes. After inactivation of Bam HI enzyme by heating at 60° C. for 10 minutes, 2 units of Eco RI and 100 microliters of Eco RI buffer were added. The mixture was further incubated at 37° C. for 60 minutes, and the reaction was then terminated by phenol extraction, after which the linearized DNA fragments were recovered by ethanol precipitation.

An 8.5 Kb DNA fragment containing the *S. marcescens* lpp gene was separately derived, as shown at 136 in FIG. 16, from a hybrid λ phage carrying the *S. marcescens* lpp gene (designated λlppSm-1) The lpp gene had previously been clone into a λ phage vector, Charon 14 (Blattner, F., et al., *Science* 196: 161-169 [1977]), as follows: Total DNA (200 micrograms) isolated from *S. marcescens* was digested with 200 units of the restriction enzyme Eco RI. DNA fragments were separated on a preparative agarose gel, and fractions of DNA fragments of approximately 8.5 Kb which showed positive hybridization with 5'$^{32}$p-lipoprotein mRNA were collected, using the Southern hybridization technique. A mixture of 8.5 Kb Eco RI fragments (enriched approximately twenty-fold) and Eco RI-cleaved Charon 14 vector DNA was reacted with T4 DNA ligase. Ligated DNA was used to transfect *E. coli* K802, NRRL B-15016. Recombinant phages carrying the lpp gene were screened by the plaque hybridization technique of Benton and Davis using 5'-$^{32}$P-lipoprotein mRNA. One of the plaques examined which gave positive hybridization was designate λlppSm-1.

Two micrograms of λlppSm-1 DNA were then digested completely with the restriction enzymes Bam HI and Eco RI, in the same manner as described immediately above with respect to linearization of pBR322, and 0.5 micrograms of the λlppSm-1 DNA fragments were combined with 0.5 micrograms of the previously-linearized plasmid pBR322 DNA in 40 microliters of ligase buffer. The mixture was heated at 37° C. for 5 minutes, and the Eco RI and Bam HI cohesive term were annealed by incubating at 4° C. for 16 hours and then at 0° C. for 1 hour. After adding ATP (0.4 mM final) and 0.4 of T4 DNA ligase, the mixture was incubated at 12.5° C. for 7 hours.

One-fourth the ligation mixture was thereafter used to transform *E. coli* lpp deletion mutant strain JE5527, NRRL B-15012. Transformation was carried out as described in Cohen, S. N., et al., *Proc. Natl. Acad. Sci. U.S.A.* 69: 2110–2114 (1972), and ampicillin-resistant transformants were grown overnight on Whatman 3MM filter papers, placed on the surface of an L broth plate containing 50 micrograms/ml of ampicillin, and screened for lpp clones by colony hybridization. A 0.95 Kb Msp I fragment of λlppEc-1 containing the lpp gene was nick-translated with [α-$^{32}$P]dATP and [α-$^{32}$P]dCTP, as described in Maniatis, T., et al., Proc. Natl. Acad. Sci. U.S.A. 72: 1184–1188 (1975), and was used as a $^{32}$P-probe. One of the transformants which gave positive hybridization was shown to contain the plasmid with the structure illustrated at 137 in FIG. 16, and this plasmid was designated pKEN221.

2. Construction Of Plasmid pKEN009

Figure 17:
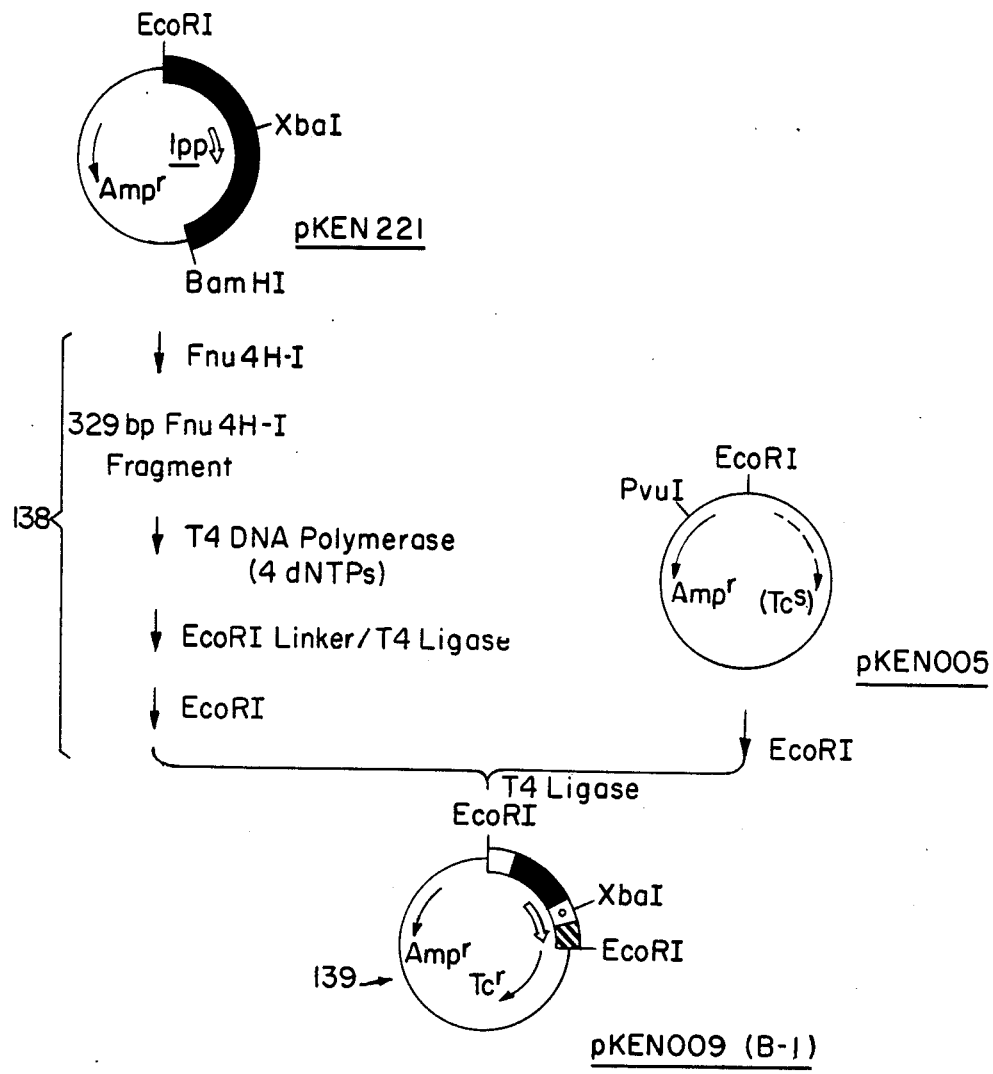

In order to construct the B site cloning vehicles, a 329 bp Fnu4H-I fragment containing the lpp promoter and 5'-untranslated region, as well as the signal peptide region of the *S. marcescens* lpp gene (this fragment is shown schematically at 105B in FIG. 5) was first cloned into pKEN005, as illustrated at 138 in FIG. 17, as follows: 80 micrograms of pKEN221 plasmid DNA were digested to completion with 100 units of the restriction endonuclease Fnu4H-I (New England Biolabs) in 400 microliters of Hae III buffer, and a 324 bp Fnu4H-I fragment was purified by acrylamide gel electrophoresis.

Since digestion with Fnu4H-I restriction enzyme results in the production of fragments with "sticky ends" at both termini, these sticky ends were modified by filling in with T4 DNA polymerase to create blunt ends. Two micrograms of the purified 324 bp Fnu4H-I fragment were treated with 3 units of T4 DNA polymerase in 20 microliters of polymerase buffer in the presence of 0.1 mM each of dATP, dGTP, dCTP and dTTP at 12.5° C. for 45 minutes. After phenol extraction and ethanol precipitation, the DNA fragments were mixed with 400 pmole of phosphorylated Eco RI linker and treated with 4 units of T4 DNA ligase in 20 microliters of ligase buffer containing 0.6 mM ATP at 12.5° C. for 16 hours. The mixture was diluted to 300 microliters with Eco RI buffer and digested with 150 units of Eco RI restriction enzyme to create Eco RI cohesive termini.

One microgram of the Eco RI-digested fragments was then mixed with 0.5 micrograms of Eco RI-digested pKEN005 plasmid DNA, and treated with 0.4 units of T4 DNA ligase in 40 microliters of ligase buffer containing 0.6 mM ATP at 12.5° C. for 16 hours. Twenty microliters of the ligated mixture was used to transform *E. coli* strain JE5519, NRRL B-15013. Upon restriction enzyme analysis of the plasmid DNAs obtained from tetracycline-resistant transformants by the rapid alkaline denaturation method, one of the plasmids was found to carry a 334 bp Eco RI fragment derived from the 329 bp Fnu4H-I fragment, and this plasmid (depicted schematically at 139 in FIG. 17) was designated pKEN009. DNA nucleotide sequence analysis of the pKEN009 plasmid DNA showed that the Eco RI site in pKEN009 lies at the B insertion site and corresponds with the B-1 reading frame. This plasmid had the DNA sequence illustrated in FIG. 19, line b, and in FIG. 20, line b. For reasons which are not understood at present, it was found that three base pairs had been inserted in the region of position +90 (resulting in the addition of one extra amino acid residue at this position) and that an extra G-C pair had been inserted at position +99. The surprising cumulative effect of these changes was to convert the amino acid sequence in the region of the signal peptide cleavage site from that of the *S. marcescens* lpp gene to that of the *E. coli* lpp gene.

3. Construction Of Plasmids pKEN017, pKEN026 and pKEN027

Figure 18:
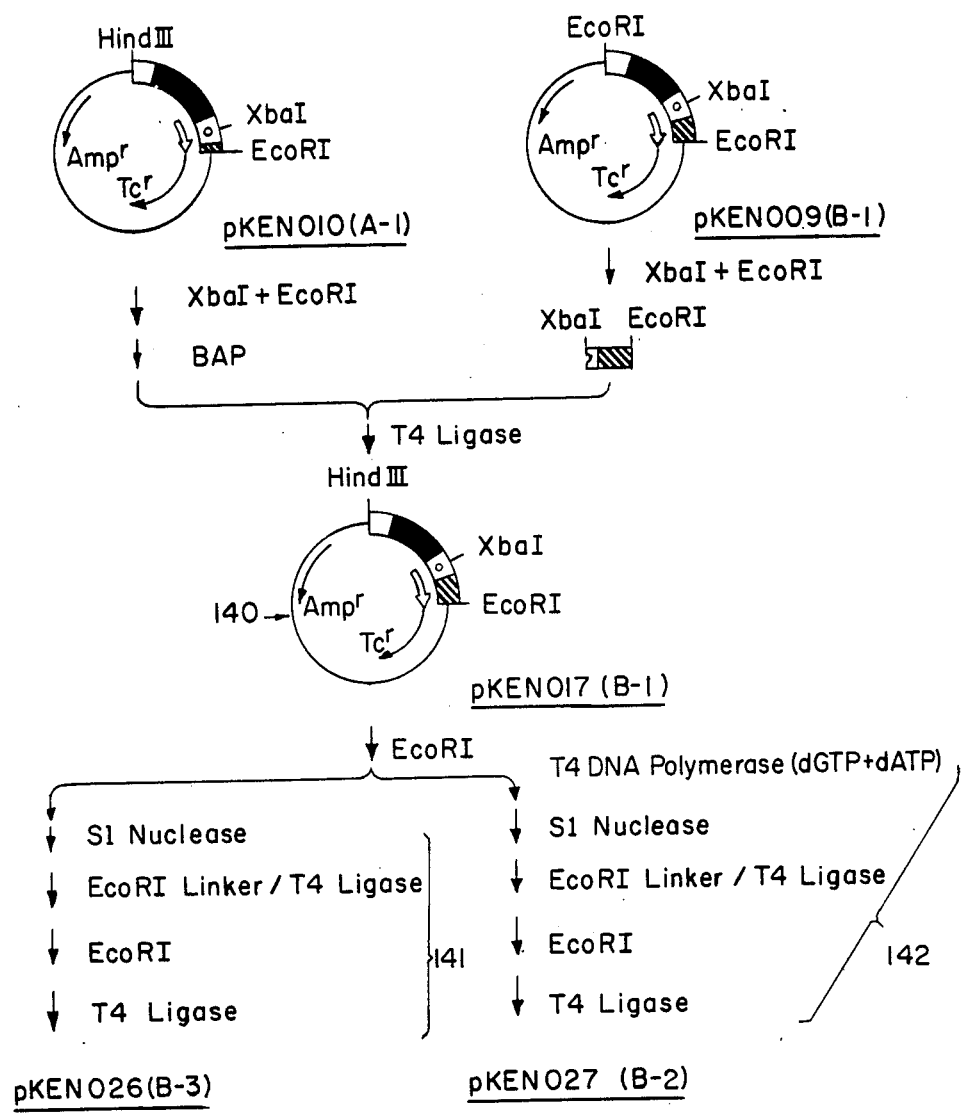

In order to construct B site expression plasmids corresponding to the B-2 and B-3 reading frames, it was first necessary to eliminate one of the two Eco RI cleavage sites of pKEN009. FIG. 18 depicts schematically the strategy for removing the Eco RI site located upstream of the lpp promoter. This procedure involved transferring an 80 bp Xba I-Eco RI fragment (containing the signal peptide and a portion of the region of the 5'-untranslated region of the *S. marcensens* lpp gene) from pKEN009 into the Xba I-Eco RI sites of pKEN010.

In order to accomplish this result, 5 micrograms of pKEN010 plasmid DNA were first digested with 5 units of Xba I restriction endonuclease in 50 microliters of Bam HI buffer, followed by digestion with 5 units of Eco RI restriction enzyme in 100 microliters of Eco RI buffer. The linearized DNA was then treated with 5 microliters of BAP in 100 microliters of 10 mM Tris:HCl (pH 8.0) and 0.1 mM EDTA at 37° C. for 30 minutes. Plasmid DNAs were extracted with phenol and precipitated with ethanol, and 0.5 micrograms of the DNA were mixed with 0.2 micrograms of an 80 bp Xba I-Eco RI fragment, which had previously been obtained by digestion of 50 micrograms of pKEN009 plasmid DNA by Eco RI and Xba I restriction enzymes, followed by polyacrylamide gel electrophoresis. The DNA mixture was treated with 0.4 units of T4 DNA ligase in 40 microliters of ligase buffer containing 0.4 mM ATP at 12.5° C. for 16 hours. Twenty microliters of the ligated mixture were used to transform *E. coli* strain JE5519, NRRL B-15013. Upon restriction enzyme analysis of the plasmid DNAs obtained from ampicillin-resistant transformants by the rapid alkaline denaturation method, one plasmid was found to contain the desired 80 bp Xba I-Eco RI fragment carrying the signal peptide region of the *S. marcescens* lpp gene in the B-1 reading frame, as shown at 140 in FIG. 18, and that plasmid was designated pKEN017.

Figure 19:
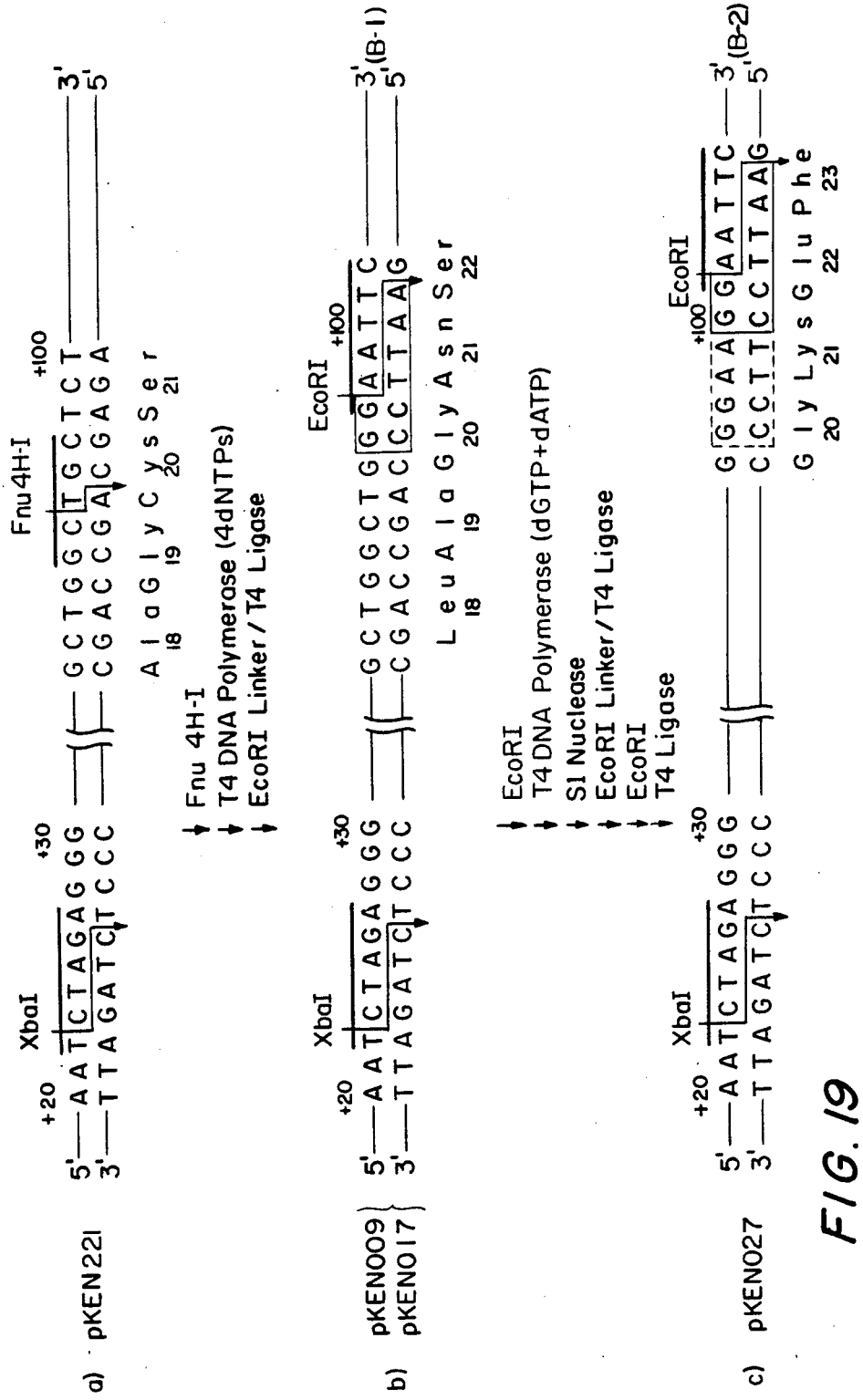
Figure 20:
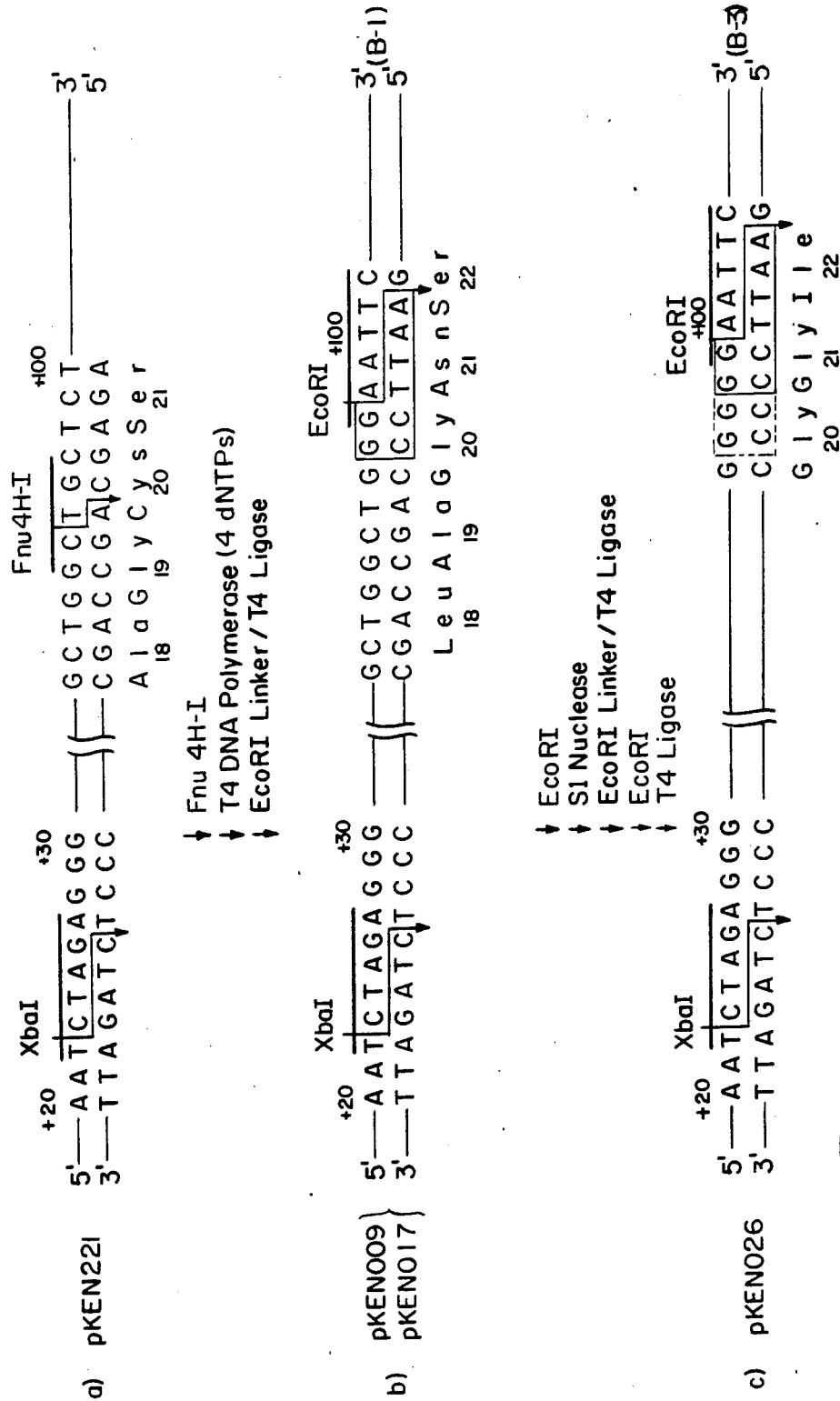

The reading frame at the B insertion site in pKEN017 was then modified to yield plasmids corresponding to the B-2 and B-3 reading frames, according to the methods previously described for changing the A-1 reading frame into the A-2 or A-3 reading frames, respectively. These procedures are illustrated schematically at 141 and 142 in FIG. 18, and the corresponding modifications of the DNA sequence around the Eco RI cleavage site are shown in FIGS. 19 and 20. It will be understood that the same procedures used to derive plasmids pKEN024 (A-2) and pKEN036 (A-3) from plasmid pKEN030 (A-1), described hereinabove in connection with FIGS. 13 and 14, can be used to derive plasmids pKEN026 (B-3) and pKEN027 (B-2) from plasmid pKEN017 (B-1).

4. Construction Of Plasmids pKEN041, pKEN047 and pKEN048

Figure 21:
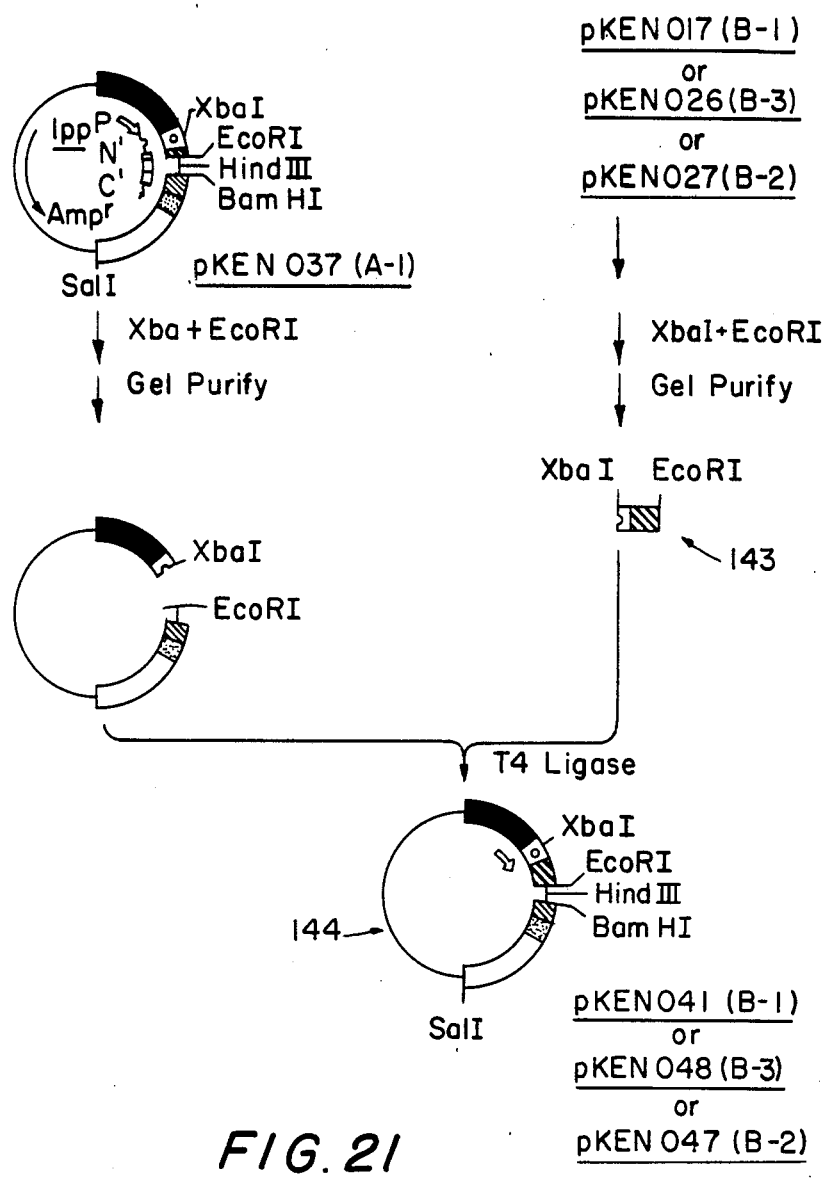

FIG. 21 illustrates schematically the last step in the construction of the B site cloning vehicles, which was to replace the Xba I-Eco RI A site fragment of pKEN037 with each of the three different Xba I-Eco RI B site fragments of pKEN017, pKEN026 and pKEN027. This was necessary in order to provide the B site plasmids with the same sequence of Eco RI, Hind III and Bam HI restriction enzyme recognition sequences at the exogenous DNA insertion site as contained in the A site plasmids. As shown schematically at 143 in FIG. 21, each of the three B site fragments derived from pKEN017, pKEN026 and pKEN027 contains the DNA sequence including the signal peptide obtained from the Fnu4H-I fragment of the *S. marcescens* lpp gene.

In order to accomplish this result, the same procedure was used to obtain the larger Xba I-Eco RI fragment of plasmid pKEN037 as was described hereinabove in connection with FIG. 15. One microliter aliquots of the aqueous pKEN037 DNA fragment mixture were each combined with a different Xba I-Eco RI smaller fragment (about 0.1 micrograms of each) previously obtained from pKEN017, pKEN026 and pKEN027, respectively, by doubledigestion with Xba I and Eco RI restriction enzymes followed by gel purification. Each DNA mixture was treated with 0.2 units of T4 DNA ligase in 20 microliters of ligase buffer containing 0.4 mM ATP at 12.5° C. for 16 hours. Ten microliters of each of the ligated mixtures were used to transform *E. coli* strain JA221, NRRL B-15014. Among the ampicillin-resistant transformants, plasmid DNAs having the B-1, B-2 and B-3 reading frames were purified, and these were designated pKEN041, pKEN047 and pKEN048, respectively, each having the structure shown at 144 in FIG. 21.

C. Construction Of C Site Plasmids (pIN-I)

FIGS. 22–26 schematically illustrate the manner in which recombinant plasmids incorporating the C insertion site were constructed, and may be referred to in connection with the following more particularized discussion.

1. Construction Of Plasmid pKEN006

Figure 22:
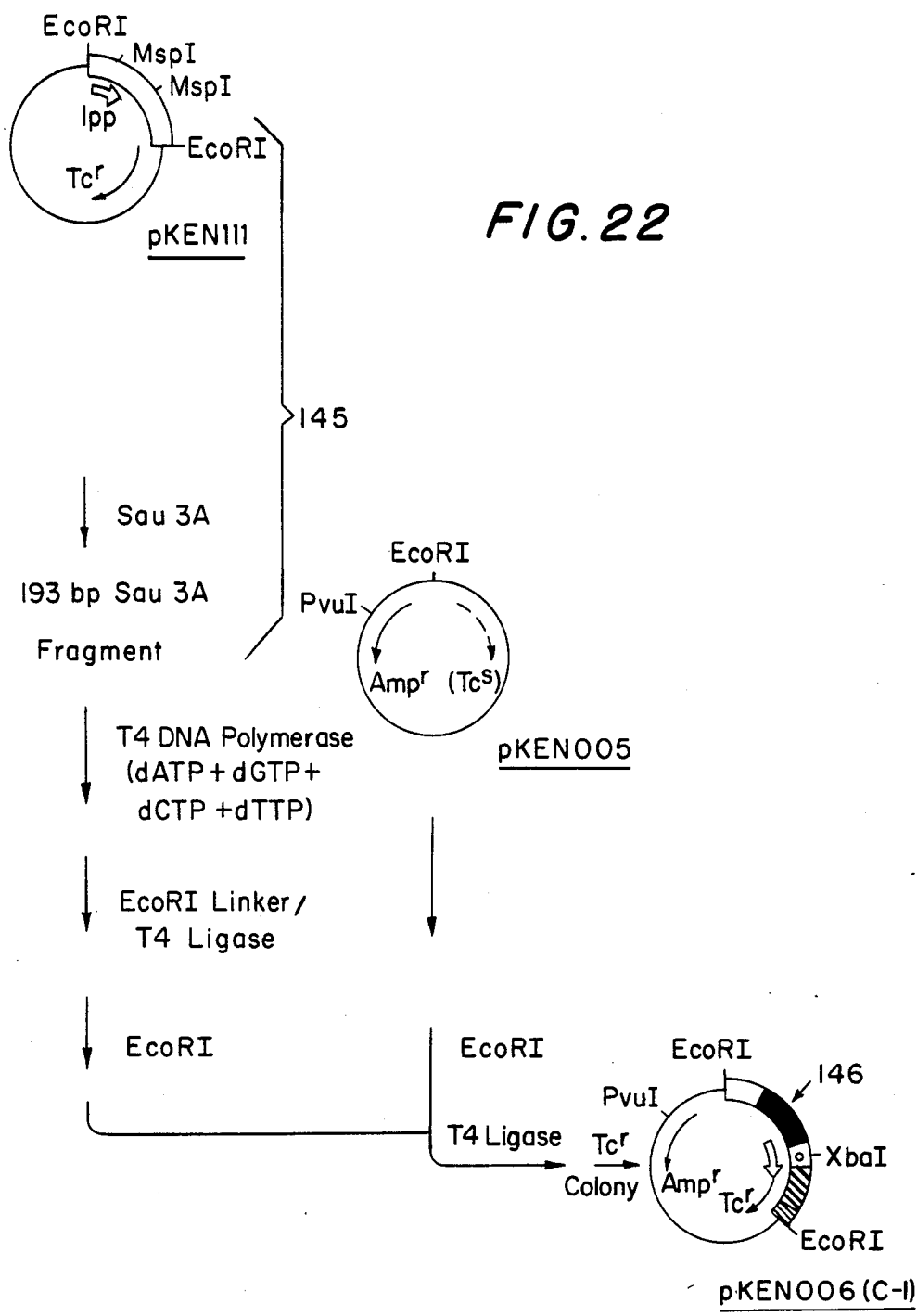

In order to construct the C site cloning vehicles, a 193 bp Sau 3A fragment containing the lpp promoter and 5'-untranslated region, as well as the signal peptide region and the first eight structural codons of the *E. coli* lpp gene (this fragment is shown schematically at 105C in FIG. 5) was first cloned into pKEN005, as illustrated at 145 in FIG. 22, as follows: 200 micrograms of pKEN111 plasmid DNA, which can be obtained by conventional means from *E. coli* CC620/pKEN111, NRRL B-15011, were digested to completion with 200 units of Sau 3A restriction endonuclease in 400 microliters of a reaction mixture comprising 10 mM Tris:HCl (pH 7.5), 10 mM MgCl$_2$, 60 mM NaCl, and 100 micrograms/ml BSA at 37° C. for one hour. After digestion was completed, phenol extraction was performed, the DNAs were recovered by ethanol precipitation, and a 193 bp Sau 3A fragment was purified by acrylamide gel electrophoresis.

Since digestion with Sau 3A restriction enzyme results in the production of fragments with "sticky ends" at both termini, these sticky ends were modified by filling in with T4 DNA polymerase to create blunt ends.

Two micrograms of the purified 193 bp Sau 3A fragment were treated with 3 units of T4 DNA polymerase in 20 microliters of polymerase buffer in the presence of 0.1 mM each of dATP, dGTP, dCTP and dTTP at 12.5° C. for 45 minutes. After phenol extraction and ethanol precipitation, the DNA fragments were mixed with 400 pmoles of phosphorylated Eco RI linker and treated with 4 units of T4 DNA ligase in 20 microliters of ligase buffer containing 0.6 mM ATP at 12.5° C. for 16 hours. The mixture was diluted to 300 microliters with Eco RI buffer and digested with 150 units of Eco RI restriction enzyme to create Eco RI cohesive termini.

One microgram of the Eco RI-digested fragments was then mixed with 0.5 micrograms of Eco RI-digested pKEN005 plasmid DNA, and treated with 0.4 units of T4 DNA ligase in 40 microliters of ligase buffer containing 0.6 mM ATP at 12.5° C. for 16 hours. Twenty microliters of the ligated mixture were used to transform *E. coli* strain JE5519, NRRL B-15013. Upon restriction enzyme analysis of the plasmid DNAs obtained from tetracycline-resistant transformants by the rapid alkaline denaturation method, one of the plasmids was found to carry an Eco RI fragment derived from the 193 bp Sau 3A fragment, and this plasmid (depicted schematically at 146 in FIG. 22) was designated pKEN006. DNA nucleotide sequence analysis of the pKEN006 plasmid DNA showed that the Eco RI site in pKEN006 lies at the C insertion site and corresponds with the C-1 reading frame.

2. Construction Of Plasmids pKEN007, pKEN019 and pKEN046

Figure 23:
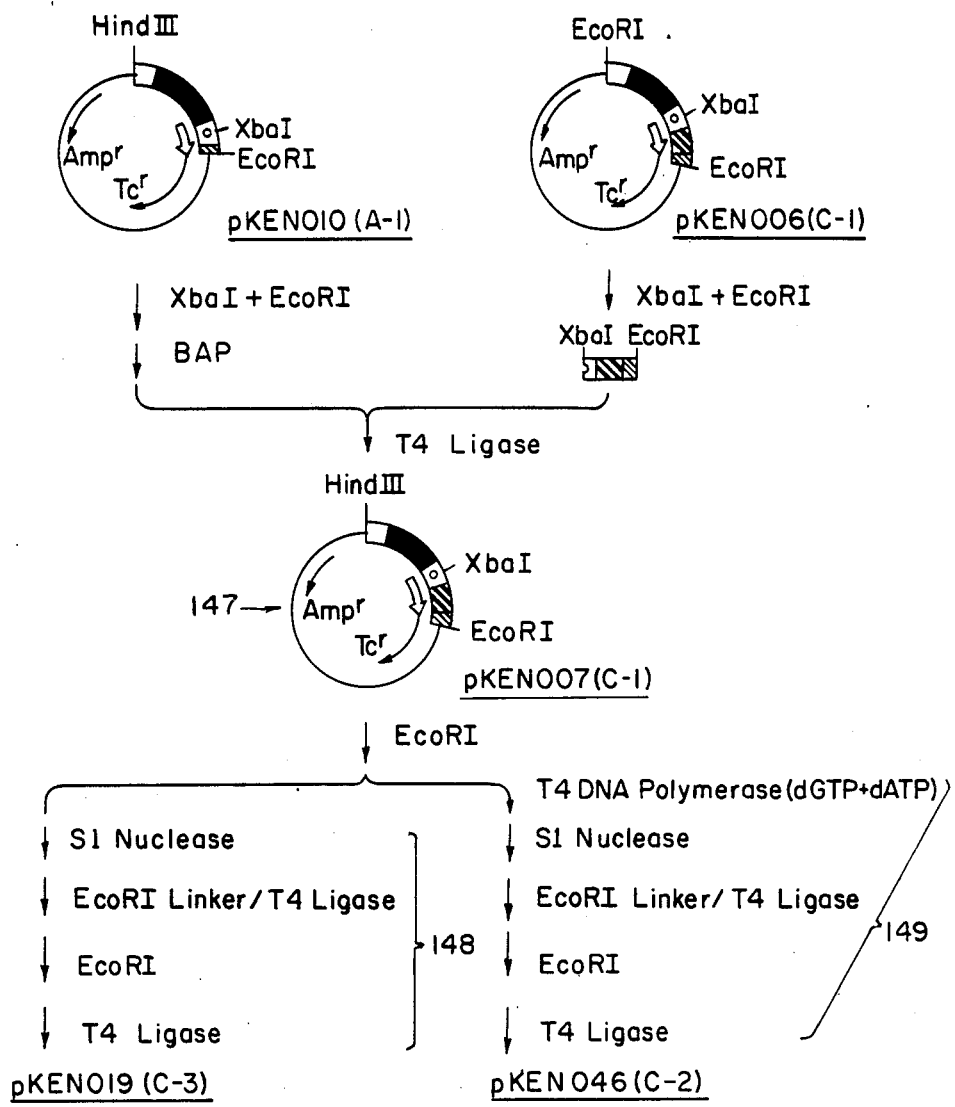

In order to construct C site expression plasmids corresponding to the C-2 and C-3 reading frames, it was first necessary to eliminate one of the two Eco RI cleavage sites of pKEN006. FIG. 23 depicts schematically the strategy for removing the Eco RI site located upstream of the lpp promoter. This procedure involved transferring a 106 bp Xba I-Eco RI fragment (containing the signal peptide, a portion of the 5'-untranslated region and a portion of the structural sequence of the *E. coli* lpp gene) from pKEN006 into the Xba I-Eco RI sites of pKEN010.

In order to accomplish this result, 5 micrograms of pKEN010 plasmid DNA were first digested with 5 units of Xba I restriction endonuclease in 50 microliters of Bam HI buffer, followed by digestion with 5 units of Eco RI restriction enzyme in 100 microliters of Eco RI buffer. The linearized DNA was then treated with 5 microliters of BAP in 100 microliters of 10 mM Tris:HCl (pH 8.0) and 0.1 mM EDTA at 37° C. for 30 minutes. Plasmid DNAs were extracted with phenol and precipitated with ethanol, and 0.5 micrograms of the DNA were mixed with 0.2 micrograms of a 106 bp Xba I-Eco RI fragment, which had previously been obtained by digestion of 50 micrograms of pKEN006 plasmid DNA by Eco RI and Xba I restriction enzymes, followed by polyacrylamide gel electrophoresis. The DNA mixture was treated with 0.4 units of T4 DNA ligase in 40 microliters of ligase buffer containing 0.4 mM ATP at 12.5° C. for 7 hours. Twenty microliters of the ligated mixture were used to transform *E. coli* strain JE5519, NRRL B-15013. Upon restriction enzyme analysis of the plasmid DNAs obtained from ampicillin-resistant transformants by the rapid alkaline denaturation method, one plasmid was found to contain the desired 106 bp Xba I-Eco RI fragment carrying the signal peptide region of the *E. coli* lpp gene in the C-1 reading frame, as shown at 147 in FIG. 23, and that plasmid was designated pKEN007.

Figure 24:
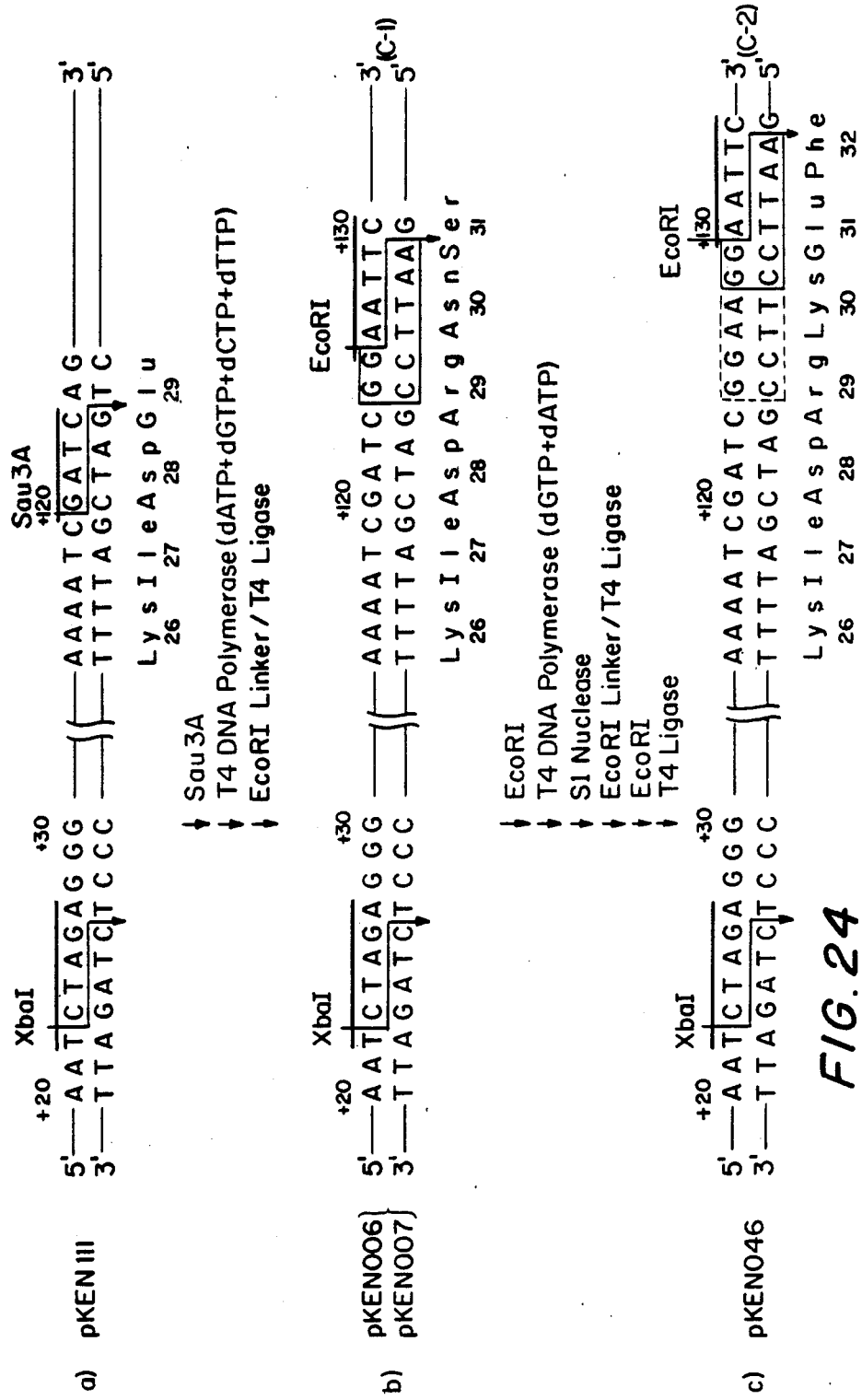
Figure 25:

The reading frame at the C insertion site in pKEN007 was then modified to yield plasmids corresponding to the C-2 and C-3 reading frames, according to the methods previously described for changing the A-1 reading frame into the A-2 or A-3 reading frames, respectively. These procedures are illustrated schematically at 148 and 149 in FIG. 23, and the corresponding modifications of the DNA sequence around the Eco RI cleavage site are shown in FIGS. 24 and 25. It will be understood that the same procedures used to derive plasmids pKEN024 (A-2) and pKEN036 (A-3) from plasmid pKEN030 (A-1), described hereinabove in connection with FIGS. 13 and 14, can be used to derive plasmids pKEN046 (C-2) and pKEN019 (C-3) from plasmid pKEN007 (C-1).

3. Construction Of Plasmids pKEN042, pKEN043 and pKEN044

Figure 26:
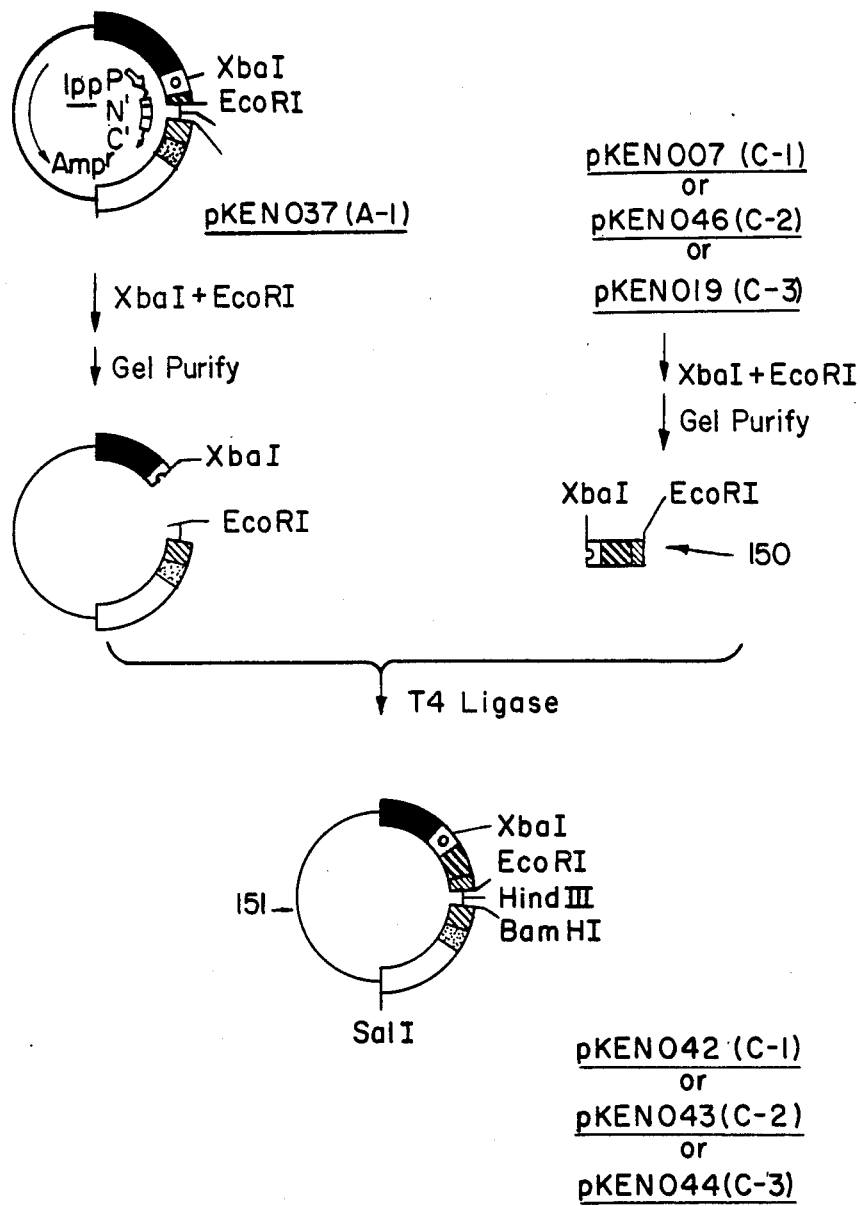

The last step in the construction of the C site expression plasmids was to substitute each of the three different Xba I-Eco RI C site fragments of pKEN007, pKEN046 and pKEN019 for the Xba I-Eco RI A site fragment of pKEN037, as illustrated in FIG. 26. This was done so that the C site plasmids would contain the same sequence of Eco RI, Hind III and Bam HI restriction enzyme recognition sequences at the exogenous DNA insertion site as contained in the A site and B site plasmids. As shown schematically at 150 in FIG. 26, each of the three C site fragments derived from pKEN007, pKEN046 and pKEN019 contains the DNA sequence including the signal peptide obtained from the Sau 3A fragment of the *E. coli* lpp gene.

In order to accomplish this result, the same procedure was used to obtain the larger Xba I-Eco RI fragment of pKEN037 as was described hereinabove in connection with FIG. 15. One microliter aliquots of the aqueous pKEN037 DNA fragment mixture were each combined with a different Xba I-Eco RI smaller fragment (about 0.1 micrograms of each) previously obtained from pKEN007, pKEN046 and pKEN019, respectively, by double digestion with Xba I and Eco RI restriction enzymes followed by gel purification. Each DNA mixture was treated with 0.2 units of T4 DNA ligase in 20 microliters of ligase buffer containing 0.4 mM ATP at 12.5° C. for 16 hours. Ten microliters of each of the ligated mixtures were used to transform *E. coli* strain JA221, NRRL B-15014. Among the ampicillin-resistant transformants, plasmid DNAs having the C-1, C-2 and C-3 reading frames were purified, and these were designated pKEN042, pKEN043 and pKEN044, respectively, each having the structure shown at 151 in FIG. 26.

D. Construction Of Inducible Expression (pIN-II) Plasmids

Figure 27:
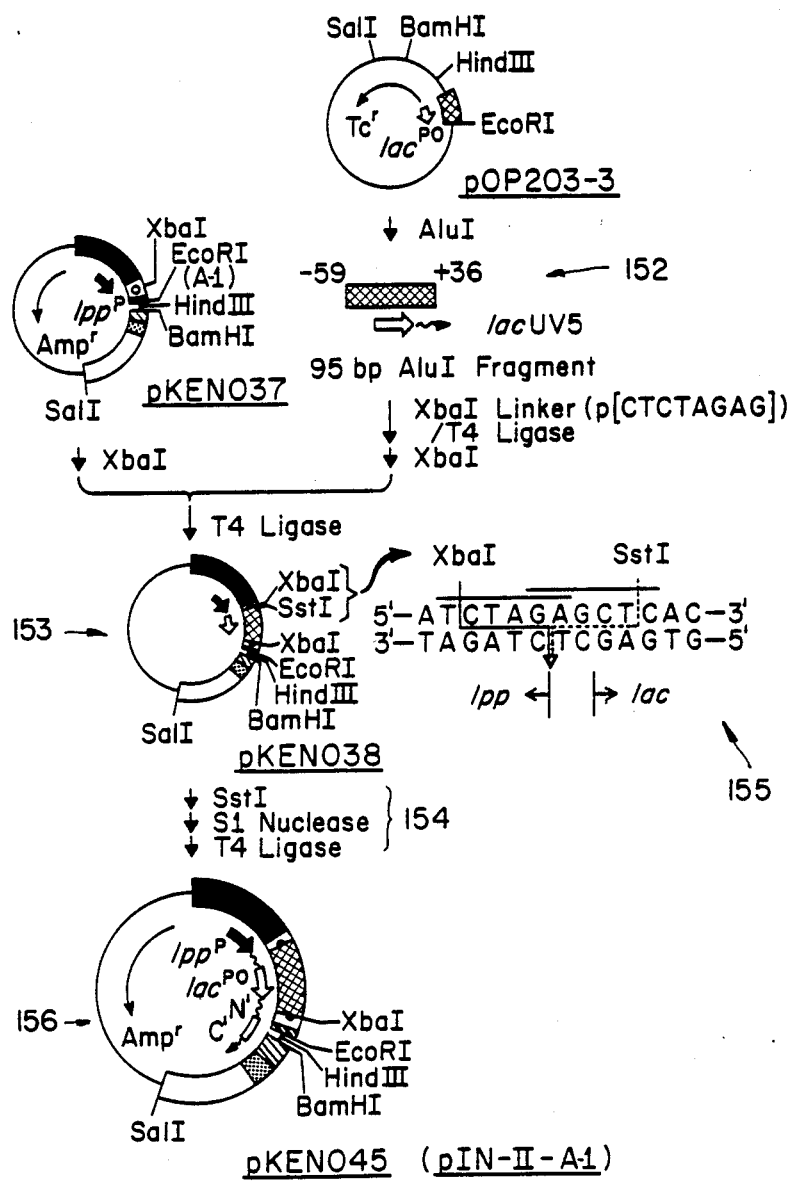

FIG. 27 schematically depicts the manner in which an inducible plasmid cloning vehicle incorporating the A insertion site in the A-1 reading frame (and corresponding to the constitutive plasmid pKEN037) was constructed. The lac UV5 promoter-operator was derived from plasmid pOP203-3 (obtained from Dr. F. Fuller, Dept. of Biochemistry and Molecular Biology, Harvard University). The lac UV5 promoter-operator is obtainable from *E. coli* 4288recA/pKM006, NRRL B-15017 or NRRL B-15236, which are available to the public from the permanent collection of the Northern Regional Research Laboratory, U.S. Department of Agriculture, Peoria, Ill., U.S.A. The lac UV5 promoter-operator is carried on a 95 bp Xba I fragment of plasmid pKM006. The plasmid can be obtained from NRRL B-15017or from NRRL B-15236 by conventional means, and the 95 bp Xba I fragment can thereafter be isolated using known techniques.

The lac UV5 promoter-operator was inserted at the Xba I cleavage site of pKEN037 (within the 5'-untranslated region of the lpp gene) according to the following procedure: 200 micrograms of pOP203-3 plasmid DNA were digested to completion with 200 units of Alu I restriction enzyme in 400 microliters of Hind III buffer, and a 95 bp Alu I fragment carrying lac UV5 promoter and operator region (illustrated schematically by the cross-hatched segment at 152 in FIG. 27) was purified by polyacrylamide gel electrophoresis. One microgram of the 95 bp Alu I fragment was mixed with 400 pmoles of phosphorylated Xba I linker (5'CTCTAGAG3'; obtained from Collaborative Research and phosphorylated in the same manner as described hereinabove), and blunt-end ligated with 5 units of T4 DNA ligase in 20 microliters of ligase buffer containing 0.6 mM ATP at 12.5° C. for 16 hours. The ligated mixture was diluted to 300 microliters with Bam HI buffer and heated at 60° C. for 10 minutes. The mixture was then treated with 100 units of Xba I restriction enzyme at 37° C. for one hour to create Xba I cohesive termini. The mixture was extracted with phenol, ethanol precipitated and lyophilized. The DNA fragments were then dissolved in 10 microliters of water, and 0.3 micrograms of the lac fragment thus obtained were mixed with 0.5 micrograms of pKEN037 plasmid DNA, which had previously been digested with Xba I restriction enzyme. The mixture was treated with 0.4 units of T4 DNA ligase in 20 microliters of ligase buffer containing 0.4 mM ATP at 12.5° C. for 16 hours to anneal the Xba I cohesive termini, thereby re-circularizing the plasmid. Ten microliters of the ligated mixture were used to transform *E. coli* JA221/F-'lacIq, NRRL B-15015, which was constructed by transferring the F' factor from χ90/F'lacIq lac+ pro+ (obtained from Dr. Beckwith, Dept. of Biochemistry and Molecular Biology, Harvard University) into *E. coli* strain JA221, NRRL B-15014. *E. coli* strain JA221/F-'lacIq is available to the public from the permanent collection of the Northern Regional Research Laboratory, U.S. Department of Agriculture, Peoria, Ill., U.S.A. Upon restriction enzyme analysis of the plasmid DNAs isolated from ampicillin-resistant transformants by the rapid alkaline denaturation method, one of them was found to contain one copy of the 95 bp Alu I fragment inserted at the Xba I site of pKEN037 in the correct orientation, as shown at 153 in FIG. 27, and this plasmid was designated pKEN038.

In order to simplify the construction of inducible plasmids containing the B and C insertion sites, it was first necessary to remove one of the two Xba I cleavage sites in pKEN038 surrounding the lac promoter-operator fragment. The Xba I cleavage site located upstream of the lac promoter-operator fragment was eliminated as shown schematically at 154 in FIG. 27. This was carried out utilizing the fact that attachment of the Xba I linker to the 95 bp lac promoter-operator fragment, as described in the preceding paragraph, resulted in the creation of a new Sst I cleavage site only at the upstream end of the lac promoter, but not at the downstream end. As shown at 155 in FIG. 27, the recognition sequence of the Sst I restriction enzyme overlaps with that of the Xba I enzyme. Thus, the deletion of the 4-base "sticky end" of the Sst I cleavage site using S1 nuclease should result in the deletion of part of the Xba I recognition sequence as well, effectively eliminating the Xba I cleavage site.

In order to accomplish this result, five micrograms of pKEN038 plasmid DNA were digested with 10 units of Sst I restriction endonuclease in 50 microliters of Bam HI buffer, and treated with 500 units of S1 nuclease in 200 microliters of S1 buffer at 20° C. for one hour. Blunt ends were joined by treatment of 0.5 micrograms of the S1 treated DNA with 5 units of T4 DNA ligase in 10 microliters of ligase buffer containing 0.6 mM ATP at 12.5° C. for 16 hours. Five microliters of the ligated mixtures were used to transform *E. coli* strain JA221/F-'lacIq, NRRL B15015. A plasmid having the structure shown schematically at 156 in FIG. 27 was isolated after restriction enzyme analysis of plasmid DNAs obtained from ampicillin-resistant transformants by the rapid alkaline denaturation method, and that plasmid was designated pKEN045 (pIN-II, A-1).

There are several methods available with which to construct pIN-II plasmids corresponding to the A-2 and A-3 reading frames. Assuming the availability of the pIN-I A-2 and A-3 plasmids, one method would involve inserting the lac promoter-operator fragment into plasmids pKEN039 and pKEN040 in the same manner as shown in FIG. 27 and described hereinabove in connection with plasmid pKEN037. An alternative and preferable method merely requires transferring the smaller Xba I-Eco RI fragments of pKEN039 and pKEN040 into the Xba I-Eco RI site of pKEN045, in a manner analogous to that described hereinabove in connection with FIG. 15, to yield plasmids pKEN049 (pIN-II, A-2) and pKEN050 (pIN-II, A-3).

On the other hand, assuming that the corresponding constitutive plasmids are not already constructed, inducible plasmids pKEN049 (A-2) and pKEN050 (A-3) can be derived directly from plasmid pKEN045 (A-1). Specifically, the DNA sequence in the vicinity of the Eco RI cleavage site of pKEN045 can itself be modified according to the scheme shown in FIG. 13, lines b and c, or the scheme illustrated in FIG. 14, lines b and c, to yield directly the structure of plasmids pKEN049 (A-2) or pKEN050 (A-3), respectively. This is the most preferred method of constructing these plasmids, since it does not require as a condition precedent the construction of the corresponding constitutive plasmids.

There are also several options available in constructing pIN-II plasmids incorporating the B and C insertion sites. Assuming again that the corresponding pIN-I plasmids have already been constructed, each could be modified to insert the lac promoter-operator fragment, according to the procedure of FIG. 27, or more preferably, the smaller Xba I-Eco RI fragment of pKEN045 (pIN-II, A-1) could be replaced successively with the smaller Xba I-Eco RI fragments from each of the constitutive B site and C site plasmids, yielding, in either case, pIN-II plasmids according to Table I.

TABLE I

| Insertion Site | Reading Frame | pIN-I Plasmids | pIN-II Plasmids |
|---|---|---|---|
| B | 1 | pKEN041 | pKEN051 |
|   | 2 | pKEN047 | pKEN052 |
|   | 3 | pKEN048 | pKEN053 |
| C | 1 | pKEN042 | pKEN054 |
|   | 2 | pKEN043 | pKEN055 |

TABLE I-continued

| Insertion Site | Reading Frame | pIN-I Plasmids | pIN-II Plasmids |
|---|---|---|---|
| | 3 | pKEN044 | pKEN056 |

Most preferably, however, the pIN-II expression plasmids are constructed without first making the corresponding pIN-I plasmids. In the case of the B insertion site, plasmid pKEN051 (pIN-II, B-1) can be derived from plasmid pKEN221 by first digesting pKEN221 plasmid DNA with Fnu4H-I restriction enzyme and then attaching Eco RI cohesive termini to the ends of the resulting fragment, according to the procedure described hereinabove and illustrated schematically at 138 in FIG. 17. The Eco RI fragment thus obtained can then be digested by Xba I restriction enzyme, splitting the fragment in two at the Xba I cleavage site located within the 5'-untranslated region. By purifying the smaller Xba I-Eco RI fragment thus obtained, and substituting it for the smaller Xba I-Eco RI fragment of pKEN045 (pIN-II, A-1), the B-1 inducible cloning vehicle can be obtained. The resulting plasmid, pKEN051 (pIN-II, B-1), can then be further modified according to the scheme illustrated schematically at 141 in FIG. 18 and in FIG. 19, or according to the scheme shown schematically at 142 in FIG. 18 and in FIG. 20, to yield the pIN-II plasmids corresponding to the B-2 and B-3 reading frames, pKEN052 and pKEN053, respectively.

An analogous course can be followed to obtain the pIN-II C site plasmids directly, without first constructing the corresponding pIN-I plasmids. Specifically, after digestion of pKEN111 plasmid DNA with Sau 3A restriction enzyme and attachment of Eco RI cohesive termini to the ends of the resulting fragment (according to the procedure described hereinabove and illustrated at 145 in FIG. 22), the Eco RI fragment thus obtained can then be digested with Xba I restriction enzyme, splitting the fragment in two at the Xba I cleavage site (located within the 5'-untranslated region). The Xba I-Eco RI fragment carrying the signal peptide region can then be inserted into the Xba I-Eco RI site of pKEN045, resulting in the plasmid pKEN054 (pIN-II, C-1). Further modification of the pKEN054 DNA according to the procedure shown schematically at 148 in FIG. 23 and in FIG. 24, or according to the procedure illustrated schematically at 149 in FIG. 23 and in FIG. 25, yields the pIN-II plasmids corresponding to the C-2 and C-3 reading frames, pKEN055 and pKEN056, respectively.

A structural gene coding for a human hormone or other desired polypeptide can be expressed in transformed bacterial hosts using a recombinant plasmid cloning vehicle constructed in accordance with the present invention, and significant quantities of the desired polypeptide can be produced thereby. However, it will be apparent to those skilled in the art that the embodiments described herein are by way of illustration and not of limitation, and that other recombinant plasmid cloning vehicles with which exogeneous genes may be expressed may be utilized without departing from the spirit and scope of the present invention, as set forth in the appended claims.

We claim:

1. A recombinant plasmid suited for use as a cloning vehicle for expression of at least one polypeptide in a transformed bacterial host, said plasmid comprising a first DNA sequence coding for at least one functional fragment derived from an outer membrane lipoprotein gene of *Escherichia coli* and selected from the group consisting of (a) the constitutive promoter, (b) the 5'-untranslated region, (c) the 3'-untranslated region and (d) the transcription termination signal of said outer membrane lipoprotein gene, said first DNA sequence including at least the constitutive promoter of said outer membrane lipoprotein gene and linked in reading phase with (a) a second DNA sequence located downstream of said constitutive promoter and coding for an inducible promoter comprising the lac promoter-operator of *Escherichia coli*, and (b) a third DNA sequence positioned downstream of said promoters for transcription therefrom and coding for the amino acid sequence of said at least one polypeptide.

2. A transformant derived from *Escherichia coli* comprising a plasmid comprised of a first DNA sequence coding for at least one functional fragment derived from an outer membrane lipoprotein gene of *Escherichia coli* and selected from the group consisting of (i) the promoter, (ii) the 5'-untranslated region, (iii) the 3'-untranslated region and (iv) the transcription termination signal of said lipoprotein gene, said first DNA sequence including at least the promoter of said lipoprotein gene and linked in reading phase with (a) a second DNA sequence located downstream of said lipoprotein promoter and coding for the lac promoter-operator of *Escherichia coli*, and (b) a third DNA sequence coding for the amino acid sequence of a polypeptide, said transformant being capable of producing the polypeptide upon fermentation in an aqueous nutrient medium containing assimilable sources of carbon, nitrogen and inorganic substances.

3. A plasmid in accordance with claim 1 wherein said third DNA sequence lies downstream of the constitutive promoter and downstream of the inducible promoter and downstream of the 5'-untranslated region and upstream of the 3'-untranslated region and upstream of the transcription termination signals.

4. A plasmid in accordance with claim 3 wherein said first DNA sequence further codes for a peptide extension capable of directing translocation of said at least one polypeptide across the cytoplasmic membrane of the bacterial host.

5. A plasmid in accordance with claim 4 wherein said third DNA sequence lies within the DNA sequence coding for the peptide extension.

6. A plasmid in accordance with claim 4 wherein said third DNA sequence lies at the 3' terminus of the DNA sequence coding for the peptide extension.

7. A plasmid in accordance with claim 4 wherein said first DNA sequence further codes for at most the entire amino acid sequence of an outer membrane lipoprotein of *Escherichia coli*.

8. A plasmid in accordance with claim 7 wherein said third DNA sequence lies within the DNA sequence coding for at most the entire amino acid sequence of an outer membrane lipoprotein of *Escherichia coli*.

9. A plasmid selected from the group consisting of pKEN045, pKEN049, pKEN050, pKEN051, pKEN052, pKEN053, pKEN054, pKEN055 and pKEN056.

10. The plasmid of claim 9 which is pKEN045.
11. The plasmid of claim 9 which is pKEN049.
12. The plasmid of claim 9 which is pKEN050.
13. The plasmid of claim 9 which is pKEN051.
14. The plasmid of claim 9 which is pKen052.
15. The plasmid of claim 9 which is pKEN053.

16. The plasmid of claim 9 which is pKEN054.

17. The plasmid of claim 9 which is pKEN055.

18. The plasmid of claim 9 which is pKEN056.

19. The transformant chosen from the group consisting of E. coli JA221/F'lacIq/pKEN045, E. coli JA221/F'lacIq/pKen049, E. coli JA221/F'lacIq/pKEN050, E. coli JA221/F'lacIq/pKen051, E. coli JA221/F'lacIq/pKEN052, E. coli JA221/F'lacIq/pKEN053, E. coli JA221/F'lacIq/pKEN054, E. coli JA221/F'lacIq/pKEN055 and E. coli JA221/F'lacIq/pKEN056.

20. The transformant of claim 19 which is E. coli JA221/F'lacIq/pKEN045.

21. The transformant of claim 19 which is E. coli JA221/F'lacIq/pKEN049.

22. The transformant of claim 19 which is E. coli JA221/F'lacIq/pKEN050.

23. The transformant of claim 19 which is E. coli JA221/F'lacIq/pKEN051.

24. The transformant of claim 19 which is E. coli JA221/F'lacIq/pKEN052.

25. The transformant of claim 19 which is E. coli JA221/F'lacIq/pKEN053.

26. The transformant of claim 19 which is E. coli JA221/F'lacIq/pKEN054.

27. The transformant of claim 19 which is E. coli JA221/F'lacIq/pKEN055.

28. The transformant of claim 19 which is E. coli JA221/F'lacIq/pKEN056.

29. A recombinant plasmid suited for use as a cloning vehicle for expression of at least one polypeptide in a transformed bacterial host, said plasmid comprising a first DNA sequence derived form an outer membrane lipoprotein gene of Escherichia coli and coding for at least one functional fragment selected from the group consisting of (a) the promoter, (b) the 5'-untranslated region, (c) the 3'-untranslated region and (d) the transcription termination signal of said lipoprotein gene, said first DNA sequence including at least the promoter of said lipoprotein gene and linked in reading phase with (a) a second DNA sequence located downstream of said lipoprotein promoter signal and coding for the lac promoter-operator of Escherichia coli, and (b) a third DNA sequence positioned downstream of said promoters for transcription therefrom and coding for the amino acid sequence of said at least one polypeptide.

30. A plasmid in accordance with claim 29 wherein said first DNA sequence further codes for a peptide extension capable of directing translocation of said at least one polypeptide across the cytoplasmic membrane of the bacterial host.

31. A plasmid in accordance with claim 30 wherein said third DNA sequence is located within the DNA coding for the peptide extension.

32. A plasmid in accordance with claim 30 wherein said third DNA sequence is located at the 3' terminus of the DNA coding for the peptide extension.

33. A plasmid in accordance with claim 30 wherein said first DNA sequence further codes for at most the entire amino acid sequence of an outer membrane lipoprotein of Escherichia coli.

34. A plasmid in accordance with claim 33 wherein said third DNA sequence is located within the DNA coding for at most the entire amino acid sequence of said lipoprotein.

35. A plasmid in accordance with claim 29 wherein said at least one polypeptide comprises a mammalian hormone.

36. A recombinant plasmid suited for use as a cloning vehicle for expression of at least one polypeptide in a transformed bacterial host, said plasmid comprising a first DNA sequence derived from an outer membrane lipoprotein gene of Escherichia coli and coding for at least one functional fragment selected from the group consisting of (a) the promoter, (b) the 5'-untranslated region, (c) the 3'-untranslated region and (d) the transcription termination signal of said lipoprotein gene, said first DNA sequence including at least the promoter of said lipoprotein gene and linked in reading phase with (a) a second DNA sequence located downstream of said lipoprotein promoter and coding for the lac promoter-operator of Escherichia coli, and (b) a third DNA sequence coding for a translation initiation codon adjacent the recognition sequence of at least one restriction endonuclease for incorporation in said plasmid of the DNA sequence coding for the amino acid sequence of said at least one polypeptide.

37. A plasmid in accordance with claim 36 wherein said first DNA sequence further codes for a peptide extension capable of directing translocation of said at least one polypeptide across the cytoplasmic membrane of the bacterial host.

38. A plasmid in accordance with claim 37 wherein said third DNA sequence is positioned within the DNA sequence coding for the peptide extension.

39. A plasmid in accordance with claim 37 wherein said third DNA sequence is positioned at the 3' terminus of the DNA sequence coding for the peptide extension.

40. A plasmid in accordance with claim 37 wherein said first DNA sequence further codes for at most the entire amino acid sequence of an outer membrane lipoprotein of Escherichia coli.

41. A plasmid in accordance with claim 40 wherein said third DNA sequence is positioned within the DNA sequence coding for at most the entire amino acid sequence of said lipoprotein.

42. A plasmid in accordance with claim 36 wherein said third DNA sequence comprises a DNA sequence containing the recognition sequences for the Eco RI, Hind III and Bam HI restriction endonucleases.

43. A plasmid in accordance with claim 42 wherein said at least one polypeptide comprises a mammalian hormone.

44. A method for producing a polypeptide in a transformed bacterial host comprising the steps of (a) selecting a recombinant plasmid including a first DNA sequence derived from an outer membrane lipoprotein gene of Escherichia coli and coding for at least one functional fragment selected from the group consisting of (a) the promoter, (b) the 5'-untranslated region, (c) the 3'-untranslated region and (d) the transcription termination signal of said lipoprotein gene, said first DNA sequence including at least the promoter of said lipoprotein gene and linked in reading phase with (i) a second DNA sequence located downstream of said lipoprotein promoter and coding for the lac promoter-operator of Escherichia coli, and (ii) a third DNA sequence positioned downstream of said promoters for transcription therefrom and coding for the amino acid sequence of said polypeptide, (b) inserting the plasmid in said bacterial host by transformation, (c) isolating and culturing said bacterial host to produce a large population of said bacterial host, and (d) adding a lactose inducer to said population to produce said polypeptide from said population.

45. A method for producing a polypeptide in a transformed bacterial host comprising the steps of (a) selecting a recombinant plasmid including a first DNA sequence derived from an outer membrane lipoprotein gene of *Escherichia coli* and coding for at least one functional fragment selected from the group consisting of (a) the promoter, (b) the 5'-untranslated region, (c) the 3'-untranslated region and (d) transcription termination signal of said lipoprotein gene, said first DNA sequence including at least the promoter of said lipoprotein gene and linked in reading phase with (i) a second DNA sequence located downstream of said lipoprotein promoter and coding for the lac promoter-operator of *Escherichia coli*, and (ii) a third DNA sequence coding for a translation initiation codon adjacent the recognition sequence of at least one restriction endonuclease for incorporation in said plasmid of the DNA sequence coding for the amino acid sequence of said polypeptide, (b) inserting within said third DNA sequence a fourth DNA sequence coding for the amino acid sequence of said polypeptide, (c) inserting the plasmid in said bacterial host by transformation, (d) isolating and culturing said bacterial host to produce a large population of said bacterial host, and (e) adding a lactose inducer to said population to produce said polypeptide from said population.

46. A transformant derived from *Escherichia coli* comprising a plasmid comprised of a first DNA sequence coding for at least one functional fragment derived from an outer membrane lipoprotein gene of *Escherichia coli* and selected from the group consisting of (a) the promoter, (b) the 5'-untranslated region, (c) the 3'-untranslated region and (d) the transcription termination signal of said lipoprotein gene, said first DNA sequence including at least the promoter of said lipoprotein gene and linked in reading phase with (a) a second DNA sequence located downsteam of said lipoprotein promoter and coding for the lac promoter-operator of *Escherichia coli* and (b) a third DNA sequence coding for a translation initiation codon adjacent the recognition sequence of at least one restriction endonuclease for incorporation in said plasmid of the DNA sequence coding for the amino acid sequence of a polypeptide, said transformant being capable of producing the polypeptide upon fermentation in an aqueous nutrient medium containing assimilable sources of carbon nitrogen and inorganic substances.

* * * * *